United States Patent [19]
Drukier et al.

[11] Patent Number: 5,866,907
[45] Date of Patent: Feb. 2, 1999

[54] ULTRALOW BACKGROUND MULTIPLE PHOTON DETECTOR

[75] Inventors: Andrzej J. Drukier, Burke; Igor R. Sagdejev, Fairfax, both of Va.

[73] Assignee: BioTraces, Inc., Herndon, Va.

[21] Appl. No.: 669,970

[22] Filed: Jun. 25, 1996

Related U.S. Application Data

[63] Continuation-in-part of Ser. No. 133,919, Oct. 12, 1993, Pat. No. 5,532,122.

[60] Provisional application No. 60/007,108, Oct. 31, 1995.

[51] Int. Cl.⁶ .............................. G01T 1/167; G01T 1/172
[52] U.S. Cl. ......................... 250/366; 250/328; 250/393; 250/394; 250/395; 250/515.1
[58] Field of Search ..................................... 250/328, 366, 250/393, 394, 395, 515.1

[56] References Cited

U.S. PATENT DOCUMENTS

| | | |
|---|---|---|
| 3,924,125 | 12/1975 | Murray . |
| 3,974,088 | 8/1976 | Coffey . |
| 3,979,593 | 9/1976 | Spragg et al. . |
| 4,005,292 | 1/1977 | Oesterlin et al. . |
| 4,016,418 | 4/1977 | Horrocks et al. . |
| 4,145,917 | 3/1979 | Brazhnikov et al. . |
| 4,284,895 | 8/1981 | Morgan et al. . |
| 4,395,634 | 7/1983 | Bohme . |
| 4,418,282 | 11/1983 | Horrocks . |
| 4,444,744 | 4/1984 | Goldenberg . |
| 4,495,420 | 1/1985 | Chudy et al. . |
| 4,563,419 | 1/1986 | Ranki et al. . |
| 4,651,006 | 3/1987 | Valenta . |
| 4,682,604 | 7/1987 | Fymat et al. . |
| 4,683,195 | 7/1987 | Mullis et al. . |
| 4,701,745 | 10/1987 | Waterworth . |
| 4,833,326 | 5/1989 | Valenta et al. . |
| 4,864,140 | 9/1989 | Rogers et al. . |
| 4,931,646 | 6/1990 | Koechner . |

(List continued on next page.)

FOREIGN PATENT DOCUMENTS

| | | |
|---|---|---|
| 0 334 528 | 9/1989 | European Pat. Off. . |
| 2 584 863 | 1/1987 | France .............................. 250/515.1 |
| 2 225 479 | 5/1990 | United Kingdom ................ 250/515.1 |

OTHER PUBLICATIONS

Yu. S. Belle and V. I. Korovin, "A Shape Discriminator for Pulses from a Combined CsI(T1)–NaI(T1) Scintillation Detector" Translated from *Pribory i Tekhnika Éksperimenta*, No. 5 (Sep.–Oct. 1974) pp. 62–65 [250/366].

E. G. Shapiro and A. L. Anderson, "Dual Energy Analysis Using Phoswich Scintillation Detectors for Low–Level In–Vivo Counting" (Place of publication unknown) (Date of publication unknown) pp. 201–209.

J. Kostamovaara et al., "A Dual Parameter (S Versus τ) Positron Annihilation Spectrometer Utilizing the $\beta^+$ –γ–γ Coincidence Applied to the Study of Defects in Al," Nuclear Instruments & Methods in Physics Research, Section B (2107B), (1984), vol. 233, No. 1, pp. 80–87.

(List continued on next page.)

*Primary Examiner*—Constantine Hannaher
*Attorney, Agent, or Firm*—Venable; Michael A. Gollin

[57] ABSTRACT

An ultralow background multiphoton detectors device for radioisotopes has a background of about one count per day. Two opposed gamma and X-ray photon detectors each preferably include a scintillation crystal and a photomultiplier tube. Sandwiched between the detectors are a separator and a sample holder for a sample labelled with a radioisotope such as $I^{125}$. The detectors convert emissions from the radioisotope into electric output pulses which are then subjected to signal processing for pulse shape analysis, discrimination of coincident from non-coincident events, and quantification of the radioisotope. Detector materials and components are selected to minimize background, and are shielded from external radiation. The device may further be constructed to resolve and provide images of two dimensional sample arrays.

132 Claims, 18 Drawing Sheets

U.S. PATENT DOCUMENTS

| | | |
|---|---|---|
| 4,933,554 | 6/1990 | Lehtinen et al. .................. 250/328 |
| 4,967,084 | 10/1990 | Rich et al. . |
| 4,983,841 | 1/1991 | Stewart et al. . |
| 4,990,785 | 2/1991 | Logan . |
| 5,016,009 | 5/1991 | Whiting et al. . |
| 5,083,026 | 1/1992 | Elbaum . |
| 5,146,093 | 9/1992 | Valenta et al. . |
| 5,285,073 | 2/1994 | Schelten et al. . |
| 5,324,952 | 6/1994 | Cummings ...................... 250/515.1 |
| 5,331,163 | 7/1994 | Leahey et al. . |
| 5,357,114 | 10/1994 | Kaihola et al. ................... 250/364 |
| 5,371,672 | 12/1994 | Motomura et al. . |
| 5,418,830 | 5/1995 | Florent . |
| 5,483,070 | 1/1996 | Valenta ............................. 250/366 |
| 5,569,844 | 10/1996 | Sowerby . |

OTHER PUBLICATIONS

Warner, G.T. et al., "A New Design for a Liquid Scintillation Counter for Micro Samples using a Flat–Bed Geometry" *Int. J. Appl. Radiat. Isot.* Oct. 1985, vol. 36, No. 10, pp. 819–821.

Yu A. Surkov, et al. "A Low–Background Gamma Spectrometer" *Sov. At. Energy,* Feb. 1973, vol. 34, No. 2, pp. 162–164.

Christman, D.R. "Measuring Radiosotopes in Organic Compounds" *Nucleonics* Dec. 1965, vol. 23, No. 12, pp. 39–45.

G. Farachi, et al., "Simultaneous Counting of True and Random Events in a Four–Fold Coincidence System Using Two Time–To–Pulse–Height Converters," Nuclear Instruments & Methods in Physics Research, vol. 164, No. 1, pp. 157–162 (1979) Aug.

Yu A. Novikov, "Universal Coincidence Circuit," Instruments and Experimental Techniques, vol. 25, No. 6, pp. 1386–1389 (1982) Nov.–Dec.

Avignone, et al., "Search for the double–$\beta$ decay of germanium–76", The American Physical Society, vol. 34, No. 2 (1986), pp. 666–677. Aug.

ULTRALOW BACKGROUND MULTIPLE PHOTON DETECTOR

This application is a continuation-in-part of patent application Ser. No. 08/133,919, entitled *Quantitation of Gamma and X-ray Emitting Isotopes*, U.S. Pat. No. 5,532,122, and is entitled to the benefit of provisional patent application Ser. No. 60/007,108, entitled *Improved Methods for the Quantitation of Low Activity Radioisotopes*, the disclosures of both of which are hereby incorporated by reference.

BACKGROUND OF THE INVENTION

1. Field

This invention relates to multiphoton radioisotope detectors with ultralow background. These detectors can quantify coincident gamma and X-ray emissions from electron capture (EC) isotopes, combining coincident counting and other background rejection measures to achieve extraordinary sensitivity.

2. Background Information

One basis of classifying detectors is according to the nature of the read-out process. In one class of detectors (photographic emulsions, phosphor imagers) the signal is integrated over a long time period (typically much longer than minutes) and only subsequently quantitated. In a second class of detectors, events are registered and analyzed on a particle-by-particle basis. This class of detectors includes gas detectors, liquid noble gas detectors, scintillators, and semiconducting detectors.

Another basis for detector classification relates to operating conditions; for biomedical applications, detectors operating at low temperature (e.g., liquid noble gas detectors, germanium detectors) and detectors requiring high pressure (pressurized gas detectors) are not as popular as detectors which operate at room temperature and ambient pressure.

A third classification approach relates to background and detector sensitivity. Detectors may be classified as (a) ultralow background detectors (ULBD) with radioactive background of less than 0.1 count per hour (<0.1 cph); (b) very low background detectors with radioactive background of less than 1 cph (<1 cph); and (c) low background detectors with radioactive background less than 1 count per minute (<1 cpm). F. T. Avignone et al., Phys. Rev. C34 (1986) 666; R. L. Brodzinski et al., NIM A254 (1987) 472; R. L. Brodzinski et al., J. of Radioanalytical and Nuclear Chemistry, 124 (1988) 513.

There are few operational ULBDs, which are typically located in large underground laboratories, and use large (multikilogram) high purity Germanium (Ge) detectors. Such detectors reduce radioactive background to about one count per day at hard X-ray energies (20–50 keV), thus allowing the detection of a solitary radioactive atom. These facilities, however, are very expensive; they are remote, and their underground location is incompatible with analytical use.

Conventional very low radioactive background detectors are very heavy, typically using over a ton of lead shielding. Conventional low background systems are used for research, and biomedical and environmental diagnostic applications. They typically use a semiconducting Ge detector with a scintillator anti-coincidence shield. However, Ge detectors have to be operated in liquid nitrogen, which severely limits their usefulness particularly when portability is desired, and they are expensive, particularly for detectors of higher energy gammas, which require 2 kg Ge detectors.

Other conventional radiation detectors have background larger than one count per minute. Gas detectors typically have an energy resolution of 10% for hard-X-rays, at 30 keV. X-ray gas detectors with heavy passive shields typically have 20–30 cpm background. They have low stopping power and require large size gas purification systems, and so have been replaced by scintillation counters in many applications. Conventional large gas detectors such as multiwire proportional chamber (MWPC) type detectors provide high spatial resolution, but require expensive multichannel electronics and have high background. Conventional drift gas chambers with fewer wires are preferred in ultralow background applications, but have poor spatial resolution in both directions for low energy deposition, e.g., when X-rays are stopped.

Scintillators are the most popular detectors for quantitation of hard X-rays and gamma-rays. There are three classes of scintillators, namely: liquid scintillators, plastic scintillators, and inorganic crystal scintillators, e.g., NaI(Tl), CsI(Tl), $CaF_2$(Eu). Good energy resolution is a goal in low background detectors achieved by selected scintillator/photosensor combinations. Among the scintillators NaI(Tl) and CsI(Tl) produce the best light yield, while among photosensors, photomultiplier tubes (PMT's) permit counting of single photoelectrons. The NaI(Tl)/PMT combination has been very popular in biomedical instrumentation.

Conventional particle/radiation detectors based on scintillator/PMT combinations can detect radioisotopes with characteristic gamma photons from about 30 keV ($I^{125}$) to about 1 MeV. These detectors usually optimize detection efficiency rather then minimize radioactive background. Multichannel analyzers (MCAs) are used to perform pulse height analysis. In detectors dedicated to high count-rate studies, the MCA is often replaced by hardware implemented upper/lower level thresholds and counters to diminish detector dead time.

In scintillation counting, liquid or solid scintillators are used to convert the beta or gamma decay energy into a pulse of visible photons, and the total photon number, which is proportional to the original particle energy, is analyzed. Disadvantages of such systems include: weight and bulk due to necessary shielding; mediocre energy resolution which limits the number of co-resident labels that can distinguished; and background levels on the order of twenty counts per minute (20 cpm). Also, some scintillators, e.g., NaI(Tl), are highly hydroscopic and thus require an appropriate housing.

Typically, a well scintillation detector (a single crystal with a hole for a sample) is used to detect and quantify low energy isotopes. To maximize the detection efficiency (DE) for higher energies, it usually has a rather large volume with typical energy resolutions of dE/E(FWHM) of 30% and 9% at 30 keV and 511 keV, respectively. Even with thick (3–4 inches of lead) shielding, the background count rate at low energies is on the order of 20–40 of counts per minute. The background is produced by cosmic rays entering the large detector volume, ambient radiation and internal contamination, for example. The cosmic rays produce low-energy background counts in two major ways: through direct excitation of atoms in the detector which then emit characteristic X-rays, and by saturating the electronics which produces spurious pulses. High-energy gamma photons from the environment (mostly $K^{40}$, $Tl^{208}$, $Bi^{2O4}$, a radon daughter in the air, and man-made contaminants) penetrate the shielding and produce secondary low-energy gamma/X-rays. Scintillators typically have radioactive contamination from $K^{40}$ actinides. Even with their high detection efficiency of 70–90%, the high background results in a minimum required input radioactivity of tens of nanoCuries (nCi) per sample.

In a typical single sample detector which uses a "well" geometry, a relatively small sample, say 1 ml or less, is placed into a cylindrical "well" NaI(Tl) scintillator. Typically, the crystal is large, >100 cm$^3$, and a single PMT is used to collect the light. This geometry is used when high DE (>80%) is required, and has an additional advantage that the DE is largely independent of the sample shape and the precision with which it is placed in the detector. A significant disadvantage of the well geometry is that only a fraction of the total scintillation light is collected, which degrades the energy resolution. Thus, large well detectors are excellent for quantitation of high energy photons (E>100 keV), but their performance deteriorates for low energies (E<50 keV).

Another frequently used geometry is a flat scintillator coupled to a single PMT. Unfortunately, this geometry leads to serious problems with calibration and requires very high precision in sample placement. Also, absorption artifacts are typically difficult to account for in this geometry, and detection efficiency is reduced due to geometric considerations.

Iodine isotope labels are extensively employed in immunoassays utilized in clinical medicine and in basic research in biochemistry, nuclear medicine, and molecular and cellular biology. Iodine is readily adducted at double covalent bonds of organic molecules, including nucleic acids, carbohydrates and proteins. Conventional detectors with backgrounds in the 10–40 counts per minute (cpm) range require use of isotopes with relatively large activity. Competitive radioassays such as radioimmunoassay (RIA) have many advantages (very high sensitivity, large number of well-understood/calibrated kits, and generally years of accumulated know-how) and are widely used in biomedical applications. However, RIA is increasingly being replaced by radioisotope-free techniques such as fluoroimmunoassay and enzymatic immunoassay, due to significant hazardous material handling and disposal problems.

Detectors for counting single gamma photons are designed for broad applicability to permit measurements of large families of gamma emitters with energies ranging from a few tens of keV to a few MeV. In these devices, multichannel analyzer (MCA) electronic systems distinguishing energy pulse heights generally serve to discriminate the energies of emissions for the plurality of source isotopes. Counting efficiency is maximized to provide the highest sample throughput. The potential of lower efficiency techniques has been generally overlooked.

Hardware implemented coincidence counting is used in a detector for positron-gamma (pg) emitters disclosed in U.S. Pat. No. 5,083,026. Within 10 nanoseconds after the coincident emission of a positron and a gamma, the positron annihilates the electron producing two back-to-back gamma photons with energies of 511 keV. Multiple scintillation detectors are used to register the three coincident high energy (E≧250 keV) gammas, and events lacking this triple gamma signature are rejected. These instruments have serious limitations, in particular the type of isotopes that may be used and the large mass and high cost of the scintillator crystals.

Some gamma photon emitting isotopes (coincident gamma and x-ray emitters, or "CGX" emitters) acquire their excited nuclear state through an electron capture (EC) from the S shell (lowest energy state). An unstable S shell vacancy and an unstable excited nuclear state result. In some cases, there is a prompt gamma photon emission from the nucleus (within less than a microsecond). Such prompt emissions may be referred to as proceeding through the "CGX" channel. The S shell vacancy may be filled by the dropping of an outer shell electron with concomitant emission of an X-ray photon or through a cascade of low energy transitions (typically below 10 keV) which progressively restructures the electron shells. However, these special characteristics of CGX emitters have not previously been employed in radioisotope detectors.

Simultaneous counting of individual and coincident gamma and x-rays is taught in Oesterlin et al., U.S. Pat. No. 4,005,292, Horrocks et al., U.S. Pat. No. 4,016,418, and Coffey, U.S. Pat. No. 3,974,088. However, these are all limited to high radioactivity applications.

Fymat et al. (U.S. Pat. No. 4,682,604) describes a tomographic probe for the detection of isotopes incorporated into selected human organs, using an array of unshielded detectors. An isotope source emitting two photons of different energy is used to remove uncertainty in the tissue attenuation coefficient due to Compton scattering and photoelectric scattering. By comparing the attenuation at two different energies, one can calculate the difference in path length traversed by the two photons. However, coincidence is not used to reject background in low activity sources, as the detected activity ranges from 2,000 to 10,000 cps, and the isotope activity is greater than a microCurie.

SUMMARY OF THE INVENTION

This invention is a break through in the crowded and mature art of radiation detectors. It succeeds where previous efforts have failed. It solves problems that were previously unrecognized or thought to be insoluble, using approaches that are contrary to the teachings of the conventional wisdom. It satisfies a long felt need for a simple, inexpensive ultralow background radiation detector with high sensitivity.

It is an object of the invention to provide an ultralow background detector. In particular, a ULBD which is specially targeted for low levels of coincident gamma/X-ray emitting isotopes (CGX isotopes). It is a further object to use the coincident photons originating from distinct nuclear and electron shell excitations of CGX isotopes as a means to selectively quantify CGX events and achieve background rejection.

A further object of the invention is to reduce background to less than one count per hour by eliminating all significant sources of background. It is a further objective of the invention to overcome the inherently lower detection efficiency of the selective CGX counting mode as compared to single gamma counters, to provide a sensitivity to sub-pico Curie samples, and an ability to detect less than $5 \times 10^{-21}$ mole of labeled molecules, a zeptomole/ml, or even a single large labelled biomolecule, with detection efficiency greater than 10% and reproducibility of about 1%.

It is another object to provide an instrument that can operate either in a non-coincident (single photon) mode or a coincident gamma-x-ray emissions (CGX events) counting mode, with enormous dynamic range and linearity of better than 5% over nine orders of magnitude.

Detectors according to the invention satisfy these objects. They have multicolor ability in that several isotopes can be measured and distinguished in the same sample. They can measure many separate samples and yield very reproducible results. They incorporate sellf-calibration and self-diagnostics. They can provide spatial resolution of 100 micrometers or lower. All these advantages are accomplished in transportable, inexpensive devices much smaller than conventional devices. Because of the increased sensitivity of instruments according to the invention, isotope concentrations may be reduced, thus lowering isotope acquisition costs, exposure of personnel, and radioactive waste disposal problems.

Further objectives and advantages will become apparent from a consideration of the detailed description and drawings.

An apparatus for detecting a radioisotope (coincident gamma/X-ray (CGX) emitter) in a sample comprises means for detecting coincident (e.g., gamma and X-ray) radiation from the CGX emitter as output pulses in separate radiation detectors, means for analyzing the shape and height of the pulses on-line to identify pulses characteristic of single photon emissions, means for discriminating and rejecting (e.g., non-coincident gamma and X-ray radiation) spurious pulses, means for suppressing background radiation, preferably a composite radiation shield and a separator that absorbs X-rays, and means for quantifying the presence of the (e.g., CGX) emitter in the sample in an amount of less than about 100 picoCurie.

At least one of the detectors preferably comprises a scintillator, preferably an inorganic scintillator with good energy resolution, and a photosensor, with the scintillator being an appropriately doped NaI or $CaF_2$ crystal with a thickness less than about 0.5 inch, and using a photomultiplier to amplify the signal from the scintillator. A large surface photodiode avalanche photodiode or photomultiplier is preferably used to amplify the signal from the scintillator. A low radioactive background quartz window can be placed between the scintillator and photosensor.

At least one of the detectors may be a Ge-semiconducting detector optimized for detection of X-rays, preferably less than 0.5 inch thick and using a cryostat with thin beryllium or aluminum windows. In an alternative embodiment, at least one of the detectors is a spatially resolving gas detector, preferably a thin self-limiting streamer chamber, and the spatial resolution is obtained by imaging, using a CCD camera.

Preferably, the detector is shielded in a low radioactive background housing covering the surface of the scintillator, of less than about 0.1 $g/cm^2$ in thickness and made of very low atomic number elements (Z less than about 13) having low radioactive background. The housing preferably comprises beryllium, aluminum, or plastic. Preferably, the detector is shielded within a shield comprising a very high atomic number metal (Z>61), such as lead, tungsten, or mercury. Most preferably, the detector is shielded within a shield comprising subsequent layers of materials with low atomic number (Z less than about 30), medium atomic number (Z between about 30 and about 60), and high atomic number (Z greater than about 61), with the high atomic number layer being the most external, wherein the materials with low and medium atomic number are highly purified copper (Cu) and tin (Sn), respectively.

Preferably, the majority of X-rays and gamma rays which are external to the source are absorbed by placing a separator between the separate radiation detectors. The separator preferably comprises a layer of a high atomic number material (Z>61) with a thickness larger than 2 mm. The separator may be cladded on both surfaces with thin layers of materials with low atomic number and medium atomic number. The low and medium atomic number materials can be highly purified copper (Cu) and tin (Sn), respectively.

There is preferably a conical hole in the separator, and the sample is placed in the hole. The sample may be placed in a sample holder comprising a narrow microcapillary ended with a spherical, hollow tip containing up to 0.1 $cm^3$ of liquid, and then placed in the separator. The sample holder may consist essentially of material with both very low atomic number (Z less than about 10) and low radioactive background, such as beryllium, aluminum, or plastic.

The separator may have a plurality of conical holes ordered into an easily distinguished pattern, and samples to be studied can be placed into the holes. The samples may be blotted upon an appropriate thin film with patterns substantially identical to the hole pattern in the separator, and the blotted film aligned with the separator between the detectors. The separator may consist of two parts, each with identical hole patterns, and the blotted film can be placed between these two parts.

The system of the invention preferably amplifies the pulse from the scintillator with low noise preamplifiers, shaping the pulse into a characteristic triangular pulse with rise time shorter than about 200 nsec and fall time between about 0.5 and about 5 microseconds, and matches the pulse shapes and amplitudes in both crystals to better than about 10%. The preamplifiers are preferably two stage preamplifiers.

The detector system preferably comprises means for analyzing each pulse for amplitude by appropriate single channel analyzers (SCA), and using the SCA outputs in a coincidence circuit (COINC) with a well defined time window, further comprising analyzing the shape of each pulse in an analog-to-digital converter (ADC) or digital storage oscilloscope (DSO) sampling at a rate of at least about 10 MHz per channel, using the signal from the coincidence circuit as trigger.

The detector preferably comprises means for storing pulse shape records from the ADC or DSO in the fast memory of a computer for further data analysis, analyzing each pulse shape record by at least one software module having acceptance criteria, rejecting a pulse on-line if it does not satisfy the acceptance criteria of all the software modules, and counting the pulse if it satisfies the acceptance criteria of all the software modules.

In an exemplary embodiment, the software modules include:

a) analyzer of pulse amplitude;
b) analyzer of the total pulse width;
c) analyzer of the shape of the rising part of the pulse;
d) analyzer of the shape of the falling part of the pulse;
e) analyzer of the delay between the pulses from the two detectors;
f) analyzer of pulse multiplicity;
g) analyzer of the pre-pulse trace; and
h) comparator of the pulse shape with a standard high energy photon pulse shape using a least squares technique;

individually or in combination.

In a spatially resolving MPD, the device of the invention may comprise means for coupling at least one of the scintillators with a spatially resolving photomultiplier tube, amplifying the output pulses from the photomultiplier tubes by at least two matched low noise amplifiers, and using the outputs as inputs to multichannel analog-to-digital converters or digital storage oscilloscope modules. Four matched low noise amplifiers are preferably used.

The device of the invention may further comprise means for analytically comparing the amplified pulses from the spatially resolving photomultiplier tube with predetermined standard shape pulses, and using only events satisfying the standard shape condition in at least two and preferably all four photomultiplier tube outputs to build 1D or 2D images. Coincident pulses may be selected to build a three dimensional scatter plot matrix, using the matrix to further optimize background rejection in off-line mode.

At least one of the detectors may be a (phosphor sandwich) module comprising a gamma detector having two optically coupled scintillators with different characteristic response times. The (phosphor sandwich) preferably comprises a very thin scintillator with high energy resolution, disposed relatively closer to the sample, and a thick, high stopping power scintillator, the two scintillators being separated by a few millimeters of optically transparent material with low radioactive background emission. Preferably, the scintillator with high energy resolution comprises NaI(Tl) or $CaF_2(Eu)$, the thick, high stopping power scintillator comprises CsI or BGO, and the optically transparent material comprises acrylic plastic or quartz. The signal from the (phosphor sandwich) is preferably amplified by a fast, low noise shaping amplifier and then analyzed by data analysis modules as described above, and the pulse shape analysis is then used to localize the scintillator element inside the phoswitch within which the photon is absorbed.

BRIEF DESCRIPTION OF THE FIGURES

The invention is better understood by reading the following detailed description with reference to the accompanying figures, in which:

FIG. 3A shows a PMT base; FIG. 3B shows a negative high voltage power supply; and FIG. 3C shows an amplifier and shaper.

DETAILED DESCRIPTION OF THE INVENTION

A general overview of an MPD device will now be presented with reference to the figures.

Figure 1:
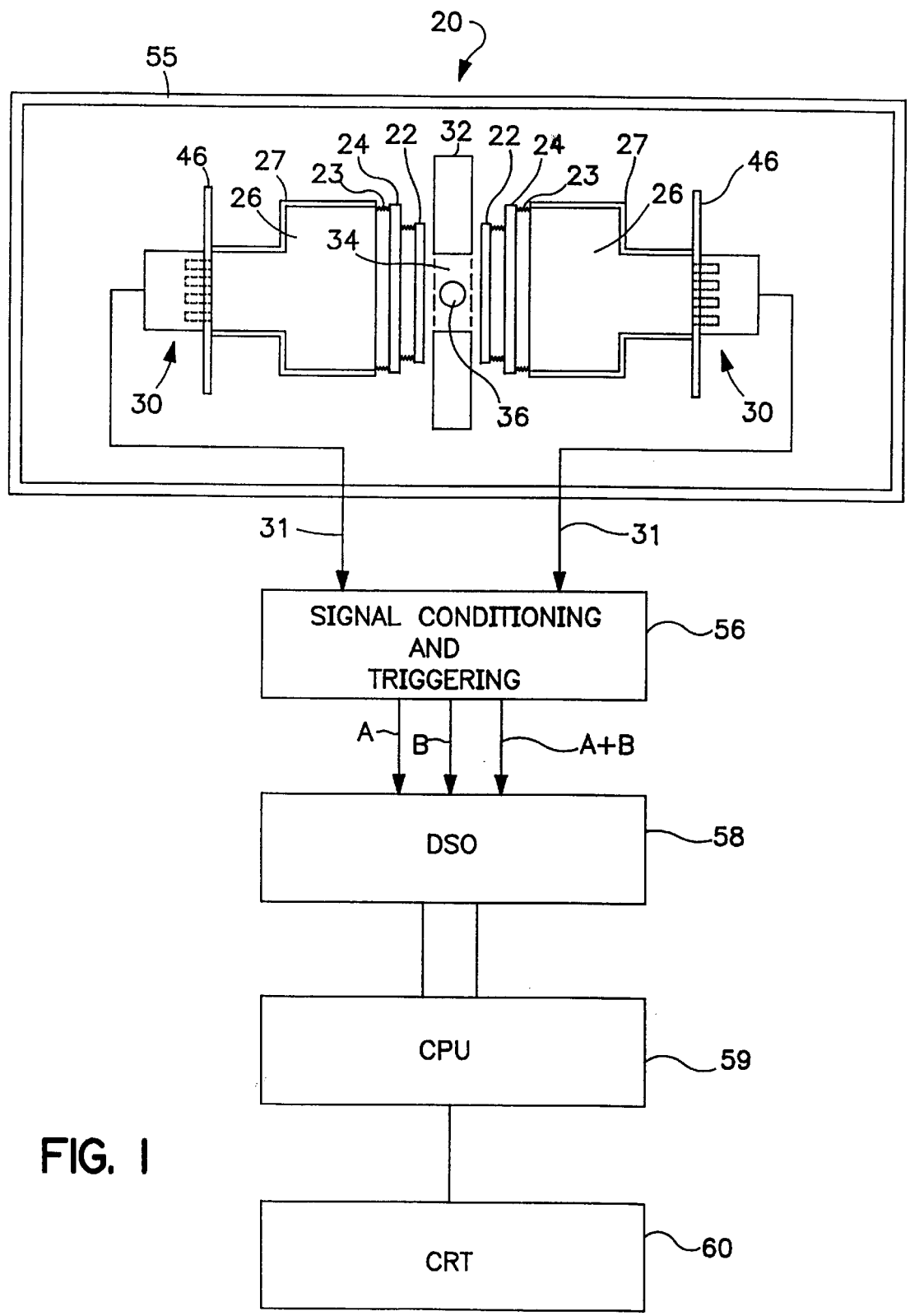
FIG. 1 shows a block diagram of multiphoton detector.

A typical embodiment of an MPD device system according to the invention is shown in FIG. 1. This exemplary system as illustrated has five major components, including:

1. two photon detectors, e.g., scintillator/photosensor modules;
2. shielding components including a separator;
3. a sample holder sandwiched between the photon detectors;
4. detection electronics including voltage supplies; and
5. signal processing for data acquisition, pulse shape/height analysis, and display.

All of the components of the exemplary embodiment are selected and arranged to minimize radioactive background.

In detector sub-assembly 20, two scintillation crystals 22 with appropriate photosensors 26, e.g., PMT's, face each other. They are separated by an appropriate separator 32, preferably less than 8 mm thick with a centered biconical hole 34 allowing sample 36 held therein to irradiate both crystals 22. The dimensions of hole 34 are chosen so that the solid angle of the opening just encompasses the faces of crystals 22. Separator 32 optimally limits cross-talk between crystals 22 and the thickness is selected to limit certain background events. The detectors are placed in composite shield 55 to diminish background due to ambient radioactivity. This shield, depending on applications, can be from 0.5 to 20 kg in weight. Each photosensor 26 is also provided with shielding 27.

A preferred isotope according to the invention is $I^{125}$, which emits a 35 keV gamma photon; in 25–35% of the decays there is coincidence between this gamma photon and one of a few characteristic X-ray photons with energies of 27 to 31 keV. The energy differences between the energy of the gamma and X-rays are small enough that a single thin scintillator/PMT system has a reasonable detection efficiency and energy resolution for both radiation types. For economic reasons scintillation counters with a few inch diameter NaI(Tl) or $CaF_2(Eu)$ crystals coupled to PMT's can be used. Crystals with 2 inch and 3 inch diameters show optimal performance. These high atomic number/high density inorganic scintillators feature superior stopping power, reasonable energy resolution, and the possibility of fast timing (<10 nsec.). Samples are placed between the faces of the opposed scintillators on essentially a common axis to produce a "sandwich geometry." To optimize the detection efficiency the isotope samples are held on the center line between the faces of the minimally separated detectors.

In operation, energy deposited within scintillation crystals 22 is converted into charge pulses by photosensors 26 and then into voltage pulses in integrated base 30. The pulses are shaped by fast low-noise preamplifiers 52, as shown in detail in FIGS. 3A–3C. The base electronics also include high-voltage power supply 50 for the photosensors 26, and high-gain amplifiers 54. Special "triangular shape" shaping preamplifiers 52 are used to permit both fast coincidence and good energy resolution. The signals A and B from both detectors 26, as well as the coincidence trigger A+B, are inputs to a PC-based digital storage oscilloscope (DSO) card 58, which is used for fast real-time pulse-shape/pulse-height analysis under software control.

The software supporting the DSO card-based pulse-shape analysis on the PC is preferably coded in Borland Turbo Pascal and C++, which helps make the code highly modular, transparent, and easy to customize. Through changes in the software, the same device can be adapted for a variety of applications without hardware changes. The most time-critical procedures are preferably coded in IBM PC assembly language to maximize efficiency of acquiring and analyzing signals.

DSO card 58 has two inputs with at least 8-bit analog-to-digital convertors (ADC's) and an additional input, which is used as an acquisition trigger. It is able to monitor the two input channels simultaneously at a sampling rate of at least 10 MHz. The signals are acquired at a sampling rate of up to 100 megasamples/sec and are continuously stored in on-board memory until a trigger is detected, whereupon a pre-defined number of post-trigger data points are acquired. Once the acquisition is stopped, the contents of the on-board memory become available for the host computer CPU 59.

Any of the DSO channels can be used as the trigger, or triggering can be done through software and/or trigger electronics 56. The sampling rate, the number of post-trigger points, the gains on the channels, and the triggering conditions can be set through a PC I/O port, while the on-board memory can be accessed directly through a 4 Kbyte window, which allows fast retrieval using the CPU's string instructions or DMA transfer to other peripheral devices, for example.

The pulse shape analysis functions as a way to discriminate pulses due to radioactive decay from spurious pulses based on the following characteristics. When a photon is absorbed by a scintillator/PMT or scintillator/photodiode combination, it produces a pulse with a characteristic shape and a predictable amplitude proportional to the energy deposited by the photon in the scintillator. In contrast, the shapes of spurious pulses electromagnetically induced in the readout electronics are not so well defined. Spurious pulses include single narrow spikes, rapid successions of such spikes, random electronic noise and PMT dark pulses. In a pulse-height analyzing system spurious pulses may considerably contaminate the acquired spectra and diminish the system's overall signal-to-background ratio. Also, many "real" pulses caused by detection of photons could be distorted, e.g., when two separate events occur within a short interval of time (pile-up artifacts) or a photon-caused pulse is distorted by a coincident electromagnetic pick-up. Such events blur the acquired spectrum, and are either discarded or correctly interpreted based on shape analysis. High-frequency electronic noise in the front end electronics perturbs the spectrum, decreasing energy resolution. However, through pulse-shape analysis the spectrum can be enhanced to the actual resolution of the photosensor.

Further, when desirable, sample counting can first proceed without coincidence for samples with activity significantly above the single gamma background. Subsequently, samples of lower activity can be recounted in the coincidence mode to achieve valid quantitation with extreme background rejection. Using the pre-established frequency of the CGX channel for a particular EC isotope, the results of the two counting modes can be computationally combined. With a dynamic range about 1000-fold greater than single gamma counters, differential treatment of samples with low and high amounts of target materials is not necessary, decreasing assay costs and increasing reliability.

Some design considerations for reducing background will next be discussed. The following sources of background are significantly reduced in the exemplary embodiments according to the invention:

A1 radioactive contamination of scintillator crystals;

A2 radioactive contamination of photomultiplier tubes (PMT's);

A3 radioactive contamination of shields;

A4 high energy gammas from the environment;

B1 neutron induced gammas from the scintillators, PMT's and shields;

B2 cosmic ray induced gammas from the scintillators, PMT's and shields;

B3 direct hits due to cosmic rays;

C1 dark pulses of PMT's;

C2 cosmic ray induced dark currents of PMT's;

D1 electronic pick-up;

D2 vibrational pick-up.

The first group of background sources (A1–A4) produces background levels on the order of a few counts per second (cps). Conventional methods of diminishing this class of background involve use of ultrapure materials, often purified to over 99.999%. However, purification methods are too expensive to be used in low cost instruments for biomedical applications. Statistical methods of background subtraction are limited by statistical artifacts and can be used only if the signal to background ratio (S/B) is large, say >10.

The second group of background sources (B1–B3) is responsible for backgrounds at the 0.1–1 counts per minute (cpm) level. Active shielding and sophisticated pulse shape analysis can be used to reject this background, but the use of active shields tends to be very expensive. Furthermore, the use of active shields often leads to complications in the detector geometry and limitations on the space available for samples, thus decreasing the utility of the device.

The third group of background sources (C1–C2) produces a few counts per hour (cph). These sources are extremely difficult to reject by hardware means. A synergistic combination of coincidence, hardware means and sophisticated pulse shape analysis permits rejection of about 90% of the background in this class. However, this requires heavy use of on-line pulse shape analysis based on a digital storage oscilloscope.

The fourth group of background sources (D1–D2), electronic and vibrational pick-up noise, is very much system and site dependent. Conventional NIM based electronics show typical noise of 0.1 cpm per unit, depending on the total number of modules used. Even when using well grounded coaxial cables, with 10 to 20 cables used to connect a typical NIM system, the observed electromagnetic noise is about 1 cpm. Also, the use of external high voltage sources negatively influences the level of pick-up noise.

To reach the level of less than one spurious count per hour, special low noise electronics are used. There is a trade-off between the on-line computing demands of a system in accordance with the invention necessary to suppress the sources B1–B3 and C1–C2, and the resulting increase in the electronic pick-up noise.

The effects of background rejection measures are summarized below in Table 1. Rejection by coincidence alone leads to about a 50-fold background rejection. The use of pulse shape analysis leads to about a 10–20 fold background rejection. Use of a special separator between the detectors permits about a factor of ten rejection of background. However, when all of these techniques are used together, a synergistic up to 50,000-fold improvement in background rejection has been achieved according to the present invention. This improved rejection of background permits an increase in sensitivity by a factor of about 10,000. Detectors according to the invention feature a dynamic range of about nine logs, i.e., they can reliably measure count rates as low as 1 cph and as high as 1,000,000 cps.

TABLE 1

Effects of radioactive background reduction factors.

Coincident Gamma-ray/X-ray Detector With Opposed Detectors

| | | |
|---|---|---|
| 2 × NaI(Tl) | without coincidence | 40 cpm |
| 2 × NaI(Tl) | MCA implemented coincidence | 1 cpm |
| 2 × NaI(Tl) | ibidem + thin composite shield | 5 cph |
| 2 × NaI(Tl) | ibidem + separator between scintillators | 1 cph |
| 2 × NaI(Tl) | ibidem + DSO pulse shape analysis | 1 cpd |

Conventional detectors with well crystal geometries:

| | | |
|---|---|---|
| NaI(Tl) | thin lead shield | 40 cpm |
| NaI(Tl) | composite passive shield | 20 cpm |
| NaI(Tl) | active shield [CsI] | 5 cpm |
| Ge | composite passive shield | 1 cpm |
| Ge | active shield [NaI(Tl)] | 20 cph | cpm = counts per minute
cph = counts per hour
cpd = counts per day
Systematic and statistical uncertainties in the background measurements are both less than 5%.

Coincidence as a background rejection measure is now discussed. In coincident gamma and X-ray (CGX) emitters, gamma emission coincides with low energy photons (UV, visible and even near infrared) from electron shell cascades, in addition to X-rays, but problems of background discrimination increase substantially for such photons. Therefore, in an optimal system for counting CGX isotopes, e.g., $I^{125}$, according to the invention, the penalty of ignoring low energy photon coincident events has been accepted to achieve exceptional background rejection.

Even with only coincidence rejection measures implemented in accordance with the invention, the background is dramatically reduced. This improvement alone provides better performance than the best conventional commercial detector type: the germanium well detector with an active external shield. It should be remembered, however, that the use of coincidence leads also to a decrease in detection efficiency. With two detector sandwich geometry and counters with 80% efficiency, the total probability of detecting coincident $I^{125}$ gamma and X-ray emission is about 15%. Thus, a CGX detector in which only coincidence is used achieves a signal/background ratio only about ten times better than conventional detectors.

Passive shielding in accordance with an other aspect of the invention provides for further background rejection. Together with coincidence, an external composite shield reduces the background from 10 to 5 cph. The shield does not influence detection efficiency but limits portability. A composite shield includes layers of materials with high, medium and low atomic number is about twice as effective as a simple lead shield. The composite shield can be about a factor of two lighter than the equivalent lead shield.

A separator in accordance with the present invention reduces "crosstalk" between the scintillation crystals by physically isolating them from each other with a gamma/X-ray absorbing material. It was expected from experiments with one counter and high activity $I^{125}$ sources that a 1 mm lead foil would be sufficient to absorb 99% of single photons. Surprisingly, the 1 mm foil was not adequate to optimally block the residual background when placed between two detectors. Rather, in the absence of a sample, a lead separator thickness of 2–5 mm was necessary to achieve a significant decrease in background counts. The thicker separator apparently blocks more complicated events than single photons. For example, some events may be initiated by cosmic rays striking the separator plate, and scattering radiation into both crystals. Radioisotopic contamination of the lead may be another source which can shed/scatter coincident radiation into the opposed crystals. With a thicker separator plate, the probability of multiple emissions reaching both detectors is diminished. When placed between the two scintillation crystals, the thick separator reduces background by a further factor of four, down to about 1 cph, while decreasing the detection efficiency by no more than 10%.

A thick separator with a biconical hole whose solid angle just exposes the crystal faces according to another aspect of the invention permits a compromise between shielding and detection efficiency requirements. A sample mount which allows optimal exposure of the crystals is both sample shape and size dependent. Different separators according to the invention having different variable hole sizes can be optimized for samples of various volumes.

Further gains are obtained through pulse shape analysis in accordance with another aspect of the invention. This analysis is performed on the output of each scintillation crystal to determine whether each constituent of the decay event is compatible with isotopic decay properties, e.g., a 35 keV gamma and one of a few X-rays in the 27–31 keV range for the case of $I^{125}$. Both events should be substantially coincident to within nanoseconds and have a pulse shape characteristic of that produced by single photons. This analysis allows discrimination from many other background events originating from charged particles, pile-up of lower energy photons, electronics saturation phenomena, electromagnetic pick-up noise and cosmic ray induced dark pulses in the PMT's for example.

Figure 6:
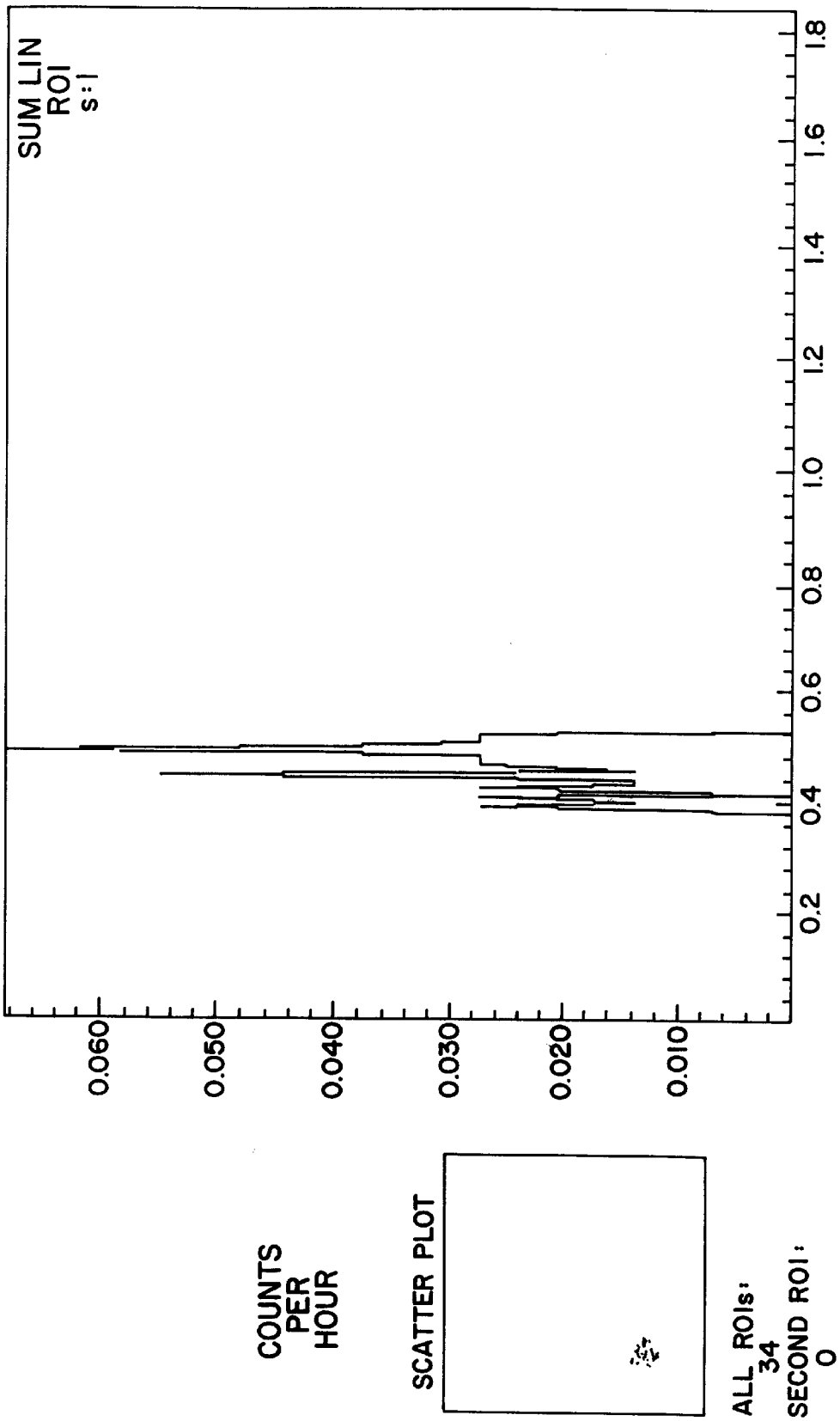
FIG. 6 illustrates the spectrum of a 1 picoCurie $I^{125}$ source obtained using a digital storage oscilloscope based spectrum analyzer, with an excellent signal to background ratio (S/B>50). For the acquisition period of 73 h, total counts were 53510, of which 1742 were not rejected. The sampling rate of the digital sampling oscilloscope was 20 MHz. The region of interest is indicated by ROI.
Figure 7:
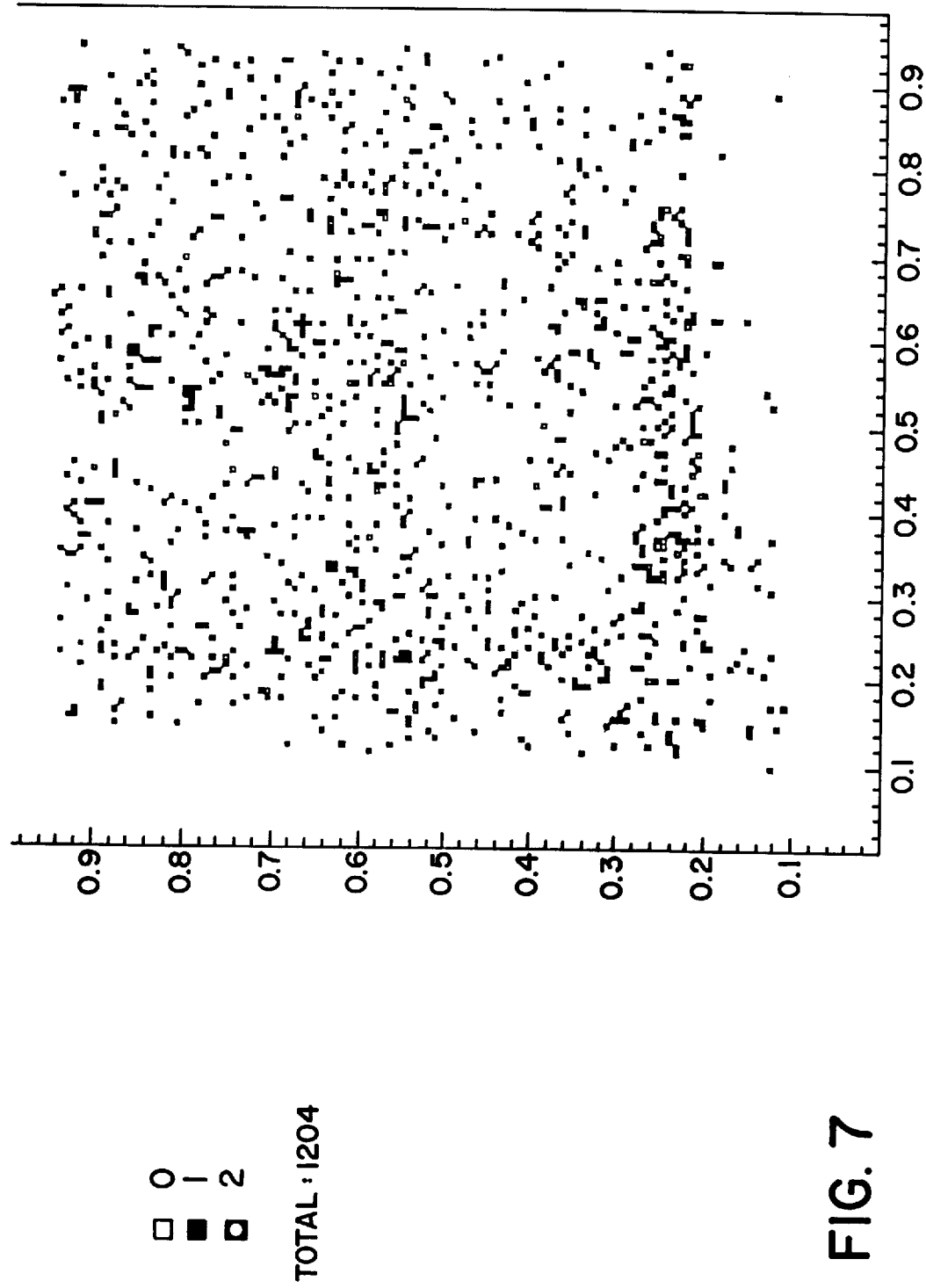
FIG. 7 illustrates the radioactive background (without sample) in a coincident gamma/x-ray detector as in FIG. 6, for 48 hours acquisition time. The total number of triggers was 57073, of which 1204 were not rejected by coincidence and pulse shape analysis. At the energy window where $I^{125}$ is expected (small cross) the count rate is about one count per day.

Knowledge of the electromagnetic pick-up noise is also used to adjust for DC offset distortions, impose coincidence checks, and enhance energy resolution according to further aspects of the invention. The implementation of real time pulse analysis normally increases the signal-to-background ratio by more than an order of magnitude, e.g., reduces background from a few cph to about 1 count per day (cpd). The analysis of a 1 picoCurie $I^{125}$ sample is shown in FIG. 6.

In the past, pulse shape analysis has been performed off-line and with very expensive electronics. According to the invention, an on-line pulse-shape analysis is preferably done using PC based Digital Storage Oscilloscopes (DSO's).

Comparisons of background rejection by multiple single channel analyzers and computers; threshold/coincidence units and multichannel analyzers (MCA's) combined; and on-line pulse shape analysis with DSO's were conducted. MCA implementations led to a background of a few counts per hour due primarily to electromagnetic pulse pick-up. However, in the same detector/shield system using DSO-based on-line pulse-shape analysis, background was about one count per day. Thus, pulse shape analysis as implemented in the present invention leads to significant improvement in background rejection.

Advantageously, DSO's permit reliable measurements by checking many parameters not available to MCA-based systems, e.g., bias level. Without any hardware overhead, DSO-based signals permit auto-diagnostics and self-calibration, e.g.,real-time monitoring of the performance of high voltage supplies, the gain of PMT's, and the linearity of the data acquisition chain.

It is desirable to keep the computational burden within the capacities of a low cost PC type computer. Background reductions due to coincidence detection, passive shielding, and the thick separator according to the present invention considerably relieve the computational burden of the DSO/computer system. This is particularly important when the CGX device is used to discriminate and quantitate multiple co-resident isotopes. Computational burdens are then much heavier, as the profiles of a decay event must be compared against the allowed profiles for each co-resident isotope.

The background reduction measures combined according to the invention result in synergistic advantages. Systems which omit one or more of the above said synergistic background rejection features will have reduced background rejection capabilities. For example, devices in which only coincidence and pulse shape analysis is used have an observed background larger than 10 cph. Devices using coincidence, a separator, and pulse shape analysis, but no composite shielding, have background of about 1 cph. Devices using coincidence, a composite shield, and pulse shape analysis, but no separator, have similar background. Thus, the background is dominated by radioactive background. However, electromagnetic and vibrational pick-up are also important at the 10 cph level. Eliminating any of the background rejection measures decreases the effectiveness of the CGX system according to the invention, so it is therefore preferable to use them all.

Isotope selection is now discussed. EC emitters typically have two coincident photons, of which one is always a rather low energy X-ray emitted due to atomic shell rearrangement. Also, some Auger electrons can be present which can be used advantageously to obtain very high spatial resolution. For the preferred radioemitter $I^{125}$, the second photon also has a low energy; the spectrum has three peaks at 27, 31 and 35 keV, respectively. Designing a MPD detector involves trade-offs between detection efficiency (DE), energy resolution (dE) and temporal response. Photon energies considerably influence the choice of detector elements. In the case of high energy emitters with at least one gamma photon with energy higher than 100 keV, heavy inorganic scintillators may be practical and economical, whereas for detection of EC isotopes a large class of detectors is available including scintillators, semiconducting detectors and gas detectors.

The EC isotopes that are preferred according to the invention are the following CGX emitters, with those having half-lives between five hours and one year being most preferred.

The 71 lighter EC isotopes are: $Be^{7}$ (53.6 d), $Na^{22}$ (2.58 y), $Ar^{37}$ (34.3 d), $V^{49}$ (330.0 d), $Cr^{48}$ (23.0 h), $Cr^{51}$ (27.8 d), $Mn^{52}$ (5.6 d), $Mn^{54}$ (291.0 d), $Fe^{52}$ (8.0 h), $Fe^{55}$ (2.7 y), $Co^{55}$ (18.0 h), $Co^{56}$ (77.3 d), $Co^{57}$ (270.0 d), $Co^{58}$ (71.0 d), $Ni^{56}$ (6.4 d), $Ni^{57}$ (1.5 d), $Cu^{64}$ (12.8 h), $Zn^{62}$ (9.3 h), $Zn^{65}$ (245.0 d), $Ga^{66}$ (9.5 h), $Ga^{67}$ (78.0 h), $As^{71}$ (62.0 h), $As^{72}$ (26.0 h), $As^{73}$ (76.0 d), $As^{74}$ (18.0 d), $Se^{72}$ (8.4 d), $Se^{75}$ (120.0 d), $Br^{76}$ (16.5 h), $Br^{77}$ (2.6 d), $Kr^{76}$ (10.0 h), $Kr^{79}$ (1.6 d), $Rb^{82m}$ (6.3 h), $Rb^{83}$ (83.0 d), $Rb^{84}$ (33.0 d), $Sr^{82}$ (25.5 d), $Sr^{83}$ (1.6 d), $Sr^{85}$ (64.0 d), $Y^{83}$ (108.0 d), $Y^{86}$ (14.6 h), $Y^{87}$ (3.33 d), $Zr^{88}$ (85.0 d), $Zr^{89}$ (3.29 d), $Nb^{92}$ (10.1 d), $Tc^{93m}$ (60. d), $Tc^{96}$ (4.3 d), $Tc^{99m}$ (6.0 d), $Ru^{97}$ (2.9 d), $Rh^{99}$ (16. d), $Rh^{100}$ (21. h), $Rh^{102}$ (206 d), $Pd^{100}$ (4.0 d), $Pd^{101}$ (8.5 h), $Pd^{103}$ (17 d), $Ag^{105}$ (40 d), $Ag^{106m}$ (8.3 d), $Ag^{108m}$ (>5 y), $Cd^{107}$ (6.7 h), $Cd^{109}$ (470 d), $In^{111}$ (2.81 d), $In^{113}$ (118 d), $Sn^{113}$ (118 d), $Sb^{119}$ (158 d), $Sb^{122}$ (2.8 d), $Te^{118}$ (60 d), $Te^{119}$ (45 d), $Te^{121}$ (17 d), $I^{123}$ (4.2 d), $I^{125}$ (60 d), $I^{126}$ (13.2 d), $Cs^{132}$ (6.5 d), $Ba^{128}$ (2.4 d), $Ba^{131}$ (11.6 d).

The 54 EC isotopes of lanthanides are: $La^{135}$ (19.8 h), $Ce^{133}$ (6.3 h), $Ce^{134}$ (3.0 d), $Ce^{135}$ (22.0 h), $Ce^{137}$ (9.0 h), $Ce^{139}$ (140 d), $Nd^{140}$ (3.3 d), $Pm^{143}$ (265 d), $Pm^{144}$ (440 d), $Pm^{145}$ (18 y), $Pm^{146}$ (710 d), $Pm^{158m}$ (40.6 d), $Sm^{145}$ (340 d), $Eu^{145}$ (5.6 d), $Eu^{146m}$ (1.58 d), $Eu^{146}$ (4.6 d), $Eu^{147}$ (24 d), $Eu^{148}$ (54 d), $Eu^{149}$ (120 d), $Eu^{150m}$ (14 h), $Eu^{150}$ (5 y), $Eu^{152}$ (13 y), $Gd^{146}$ (48 d), $Gd^{147}$ (35 h), $Gd^{149}$ (9 d), $Gd^{151}$ (120 d), $Gd^{153}$ (200 d), $Tb^{151}$ (19 h), $Tb^{152}$ (18 h), $Tb^{153}$ (2.58 d), $Tb^{154m}$ (8 h), $Tb^{154}$ (21 h), $Tb^{165}$ (5.4 d), $Tb^{160}$ (73 d), $Dy^{155}$ (10 h), $Dy^{157}$ (8.2 h), $Tm^{165}$ (1.21d), $Tm^{167}$ (9.6 d), $Tm^{168}$ (85 d), $Yb^{169}$ (32 d), $Lu^{169}$ (1.5 d), $Lu^{170}$ (2.0 d), $Lu^{171}$ (8.3 d), $Lu^{172}$ (6.7 d), $Lu^{173}$ (1.3 y), $Lu^{174m}$ (165 d), $Hf^{173}$ (24 h), $Hf^{175}$ (70 d), $Ta^{175}$ (11 h), $Ta^{176}$ (8.0 h), $Ta^{177}$ (2.21 d), $Ta^{179}$ (1.6 y), $Ta^{180m}$ (8.1 h).

The 40 EC isotopes of very heavy metals are: $W^{181}$ (130 d), $Re^{181}$ (20 h), $Re^{182m}$ (13 h), $Re^{182}$ (64 h), $Re^{183}$ (71 d), $Re^{184m}$ (2.2 d), $Re^{184}$ (50 d), $Re^{186}$ (90 h), $Os^{183m}$ (10 h), $Os^{183}$ (12 h), $Os^{185}$ (94 d), $Ir^{185}$ (15 h), $Ir^{187}$ (12 h), $Ir^{188}$ (1.71 d), $Ir^{189}$ (11 d), $Ir^{190}$ (11 d), $Ir^{192}$ (74 d), $Pt^{191}$ (3.0 d), $Au^{193}$ (15.8 h), $Au^{194}$ (39 h), $Au^{195}$ (200 d), $Au^{196}$ (5.55 d), $Hg^{193m}$ (1.1 d), $Hg^{193}$ (6 h), $Hg^{194}$ (130 d), $Hg^{195}$ (1.66 d), $Hg^{195}$ (9.5 h), $Hg^{197m}$ (24 h), $Hg^{197}$ (2.71 d), $Tl^{200}$ (1.08 d), $Tl^{201}$ (3.04 d), $Tl^{202}$ (12 d), $Tl^{204}$ (3.9 y), $Pb^{200}$ (21 h), $Pb^{201}$ (9.4 h), $Pb^{202}$ (2.17 d), $Bi^{203}$ (12.3 h), $Bi^{204}$ (11.6 h), $Bi^{206m}$ (15.3 d), $Bi^{206}$ (6.3 d), $Bi^{207}$ (30 y).

The 15 EC isotopes of actinides are: $Po^{206}$ (8.8 d), $At^{210}$ (8.3 h), $At^{211}$ (7.2 h), $Rn^{211}$ (16 h), $Ac^{226}$ (29 h), $Pa^{228}$ (22 h), $Pa^{229}$ (1.5 d), $U^{231}$ (4.2 d), $Np^{234}$ (4.4 d), $Pu^{234}$ (9 h), $Pu^{237}$ (45.6 d), $Am^{239}$ (12 h), $Cm^{241}$ (35 d), $Bk^{245}$ (4.95 d), $Bk^{246}$ (1.8 d).

Preferably, the CGX emitter is an isotope of an element that forms covalent bonds, or one that can be chelated to an organic compound. More preferably the isotope is $I^{123}$, $I^{125}$, $I^{126}$, $Br^{76}$, or $Br^{77}$, and most preferably is $I^{125}$.

The EC isotope $I^{125}$, with a half life of 60 days, is particularly preferred. According to results obtained with older instrumentation and recorded in nuclear data tables, coincident emission of a 35 keV nuclear gamma and one of several possible X-rays in the 27–31 keV range occurs in 7% of the $I^{125}$ decays. However, with the improved system of the invention, experiments revealed in actuality a coincidence in 25–35% of the decays.

The CGX emitter is preferably an isotope of the family of CGX lanthanide isotopes. This family includes 54 isotopes with identical chemical properties which are distinguishable based on their different decay photon energies. CGX lanthanide isotopes can be introduced as labels to biomolecules through the use of chelating groups which capture metallic ions. The chemistry for adducting chelating groups to DNA subunits and their polymers is well known.

Material selection for an ultralow background CGX system for $I^{125}$ will now be discussed. The detection of gamma rays from $I^{125}$ requires scintillator detectors with good energy resolution. Generally, the best energy resolution is achieved with a NaI(Tl) crystal/PMT combination. However, use of NaI(Tl) leads to an additional hard X-ray background due to the characteristic iodine absorption edge. This is beneficially eliminated by implementing the preferred $CaF_2$/PMT combination according to the invention.

All materials used in the CGXD system in more than 1 mg quantity are screened for radioactive impurities. Glass which contains $K^{40}$ is preferably replaced by quartz or special low background pyrex. Ferric materials are excluded because of radioactive cobalt contamination. Fortunately some types of plastic, e.g., TEFLON and acrylic, are acceptable, as well as ultrapure copper, tin and lead.

Ultrapure scintillators are used in ultralow background detectors for double beta decays and cold dark matter. They have about three orders of magnitude lower radioactive background than previously available scintillators. At this level, most of the background comes from $K^{40}$ in the glass of the PMT's. Quartz PMT's can be used but are quite expensive. Furthermore, even if the radioactive contamination due to $K^{40}$ is eliminated, there is a non-negligible radioactive background due to the photocathodes. In the past few years, large area (larger than one $cm^2$) photodiodes (PD's) and avalanche photodiodes (APD's) have become commercially available. In contrast with PMT's, PD's/APD's are smaller, more robust physically, require only a low voltage power supply (typically <100 V for PD's) and have much lower total energy consumption. They are also less sensitive to temperature changes and stray magnetic fields. Thus, the replacement of PMT's with ultrapure Si-based devices is conducive to lower overall background and higher sensitivity.

MPD devices for particular uses are now described. Use of phoswich for isotopes with high energy gammas: The case of $I^{125}$ is not typical of CGX isotopes because the X-ray energy (27–31 keV) is very close to the gamma ray energy (35 keV). For many CGX sources, however, the gamma ray is in the 200–2,000 keV range.

In theory, energy resolution is limited by the statistics of the scintillation photon emission. In practice, the energy resolution is also limited by the choice of PMT, the bias voltage, and the noise of the front-end electronics. System optimization according to the invention is often different at high and low energies. At low energies, somewhat better energy resolution is possible when the gains of the PMT are low, on the order of a hundred thousand rather than a few million.

When the X-ray and gamma energies from the CGX channel differ by factors of a few or more, at least one crystal must be thick enough to absorb all the energy deposited by the gamma. When used to discriminate multiple isotopes, the crystal thickness of a CGX device is determined by the requirement to absorb all of the energy from the most energetic gamma emitted by members of the isotope collection being quantitated. This results in some increase in background for the X-ray detection, as more cosmic rays and high energy gammas, e.g., from $K^{40}$, deposit energy in the greater volume of scintillator.

With CGX emitters with higher energy gammas, the separator and the shield are preferably thicker and the fraction of the high atomic number component increases. Also, changes in software are preferred. Different parameters are used in acceptance criteria, especially concerning the pulse width and pulse rise time. These parameters are determined empirically at setup by using a high activity test source of the appropriate radioisotope. The method of determining these parameters is described in further detail in the section describing the instrument calibration software.

To minimize problems caused by the increased X-ray background described above, the sample is preferably placed between paired phoswich (phosphor sandwich) detectors. A phoswich is a combination of two scintillators with very different response times, both optically coupled to a single PMT or other photosensor. It allows for more efficient detection of low and high energy photons, such as soft X-rays and gammas.

One implementation is a thin NaI(Tl) crystal with a thick CsI crystal behind it, followed by the common PMT. For example a 0.1 inch NaI(Tl) scintillator serves as a high energy resolution, low energy gamma/X-ray detector which is substantially transparent to hard gammas. The backing CsI scintillator serves as the high energy hard gamma photon detector. Due to the different response times of the fast and slow scintillators, the pulse shape permits a determination of whether a photon was absorbed in the slow or the fast scintillator. The energy of the more energetic photon can be calculated from the knowledge of the X-ray/gamma-ray absorption position and the pulse height. Coincidence events can thus be scored, whether the gamma and X-ray are absorbed in a single phoswich or in both opposed phoswich.

Conventional phoswich detectors use complicated hardware electronics to measure scintillator light pulse duration. These are appropriate for high energy gamma-rays, say E>200 keV and for high count rate experiments, but lead to artifacts when used for soft X-rays and in low count rate applications.

Preferably, a 4" bismuth germanate (BGO) crystal is used as an active (anticioncidence) shield around the phoswitch. This provides an increase in sensitivity of about five to ten times as compared to passively shielded CGX systems, and four orders of magnitude greater than unshielded or passively shielded devices currently used in hospitals.

Portable CGX system using photodiodes: Photodiodes or avalanche photodiodes may be used to replace the PMT because of their greater robustness, better stability under temperature variations and lower power requirements. With background rejection by coincidence and pulse shape analysis implemented, less than two kilograms of passive composite shielding is adequate. Such light devices are highly portable. Software management can be implemented on a laptop computer. Either the opposed detector sandwich configuration or the phoswitch format described above can be used.

Multisample system using spatially resolving PMT's: Spatially and temporally resolving X-ray/gamma detectors according to the invention may be built by coupling a single scintillation crystal to a spatially resolving PMT. For example, the Hamamatsu R2486 PMT has four outputs. Measurement of the pulse heights in all four channels allows calculation of the spatial position of the absorbed gamma. Quantitative imaging of 2D sources in contact with the crystal is thus achieved. Good spatial resolution is best achieved only for rather high-intensity sources (1 cps or higher) because of electronic interference noise. This considerable capacitive noise is inherent in these multielectrode devices, and is complicated by the fact that charge division leads to lower amplitude signals. Thus, artifacts due to EMI influence a spatially resolving PMT more than a simple PMT.

An embodiment of the invention may be used for CGX isotopes arrayed or distributed on a two dimensional membrane support. The 2D specimen is placed between a non-imaging "hard" detector optimized for the gamma emission on one side, and the imaging PMT on the other. The X-ray is efficiently stopped in the planar scintillator of the imaging scintillator/PMT. An event analysis is triggered by coincident signals from the hard and imaging detectors. Multiple DSO cards are used, and DSO pulse shape analysis is performed on each of the four PMT outputs (or on the sum of the four outputs) as well as that of the hard detector. This analysis helps avoid mistakenly attributing decays at one site to another, which may arise because the signals for a large fraction of events are very small and susceptible to electromagnetic and electronic noise. The result is an increase in spatial resolution, particularly for low activity sources. Thus, sharper images can be obtained, and samples may be placed closer on the support membrane.

Gamma and cascade photon coincidence detection: This implementation is designed to capture events in which multiple low energy, cascade photons are emitted during the restructuring of electron shells following electron capture, in coincidence with the gamma from the excited nucleus. The sample is placed between two distinct detector assemblies.

A PMT-NaI(Tl)-CCD-sample-NaI(Tl)-PMT configuration is suggested. In contrast to the prior described implementations, there are considerable complications in data analysis. The totality of events should be analyzed to decide if the event in the CCD is just a UV/visible photon from a cascade or if it results from an X-ray. This preferably involves a very low noise single-photon CCD and a cooled device.

Figure 12:
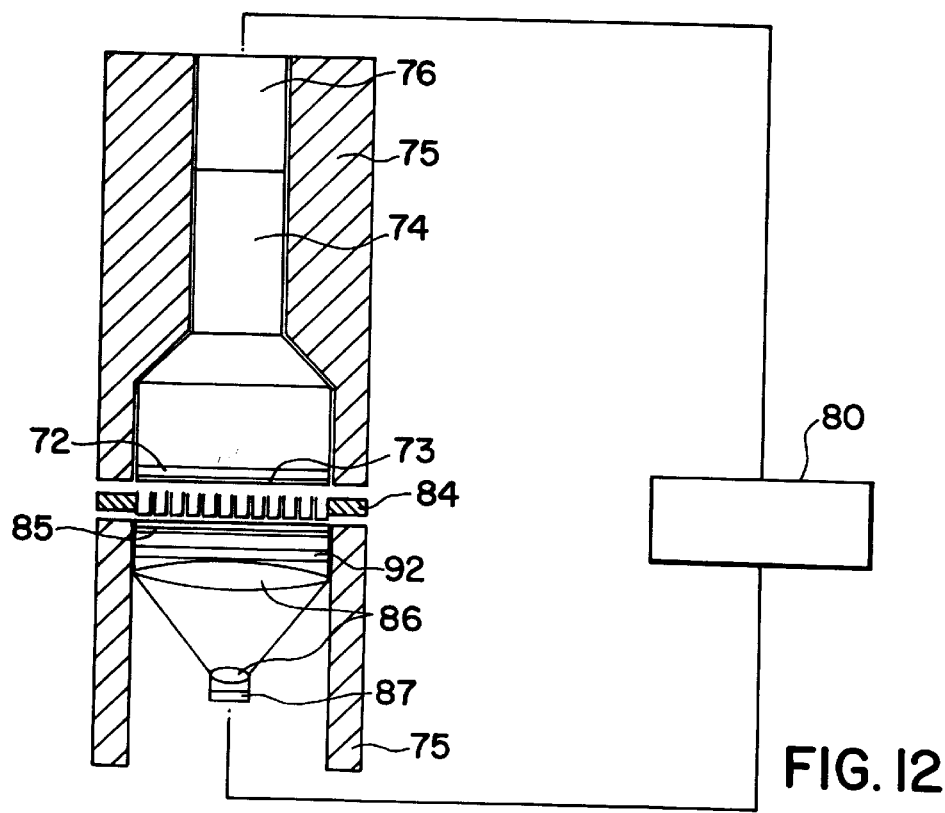
FIG. 12 shows an apparatus using a gas detector and CCD.

Alternatively, the following configuration may be used: as shown in FIG. 12 for a typical configuration having a scintillation detector above, comprising scintillator crystal 73, quartz window 72, photomultiplier tube 74, and base electronics 76 in lead shield 75, and connected to readout electronics 80, with sample holder cassette 84 between the two detectorsCCD-gas detector-sample-NaI(Tl)-PMT. The gas detector 85 is operated in the self-limited streamer mode. Thus, at the applied high voltage (typically 1000 Volts) a single photon absorption leads to discharge. The gas composition is selected so that the breakdown is not total, leading to spark creation that is limited to lead to about 0.2 mm long streamers. The resulting 100,000 amplification in the number of electrons leads to emission of many visible photons. The location of this light pulse is detected by a low noise CCD (charge coupled device) 87. It takes a part of a microsecond to develop the streamer, so the gas detector operated in self-limiting mode has a built-in delay, which facilitates its application in coincident systems, e.g., in CGX detector 85 systems according to the invention.

The experimental difficulty is that the gas detector may be much larger than the size of the CCD 87. Thus, large focal length optics should be used. To increase the light yield an array of lenslets 86 is placed between the gas detector 85 and CCD 87. Each of these lenses collimates the divergent light pulse into a flat front or convergent beam.

To improve the photon signal/noise and diminish the detector size, one can use an enhanced CCD, i.e., a combination of a microchannel plate 92 and a CCD. Microchannel plates are available with 10 inch diameter, i.e., about a factor of five larger than the CCD. Thus, the image from the gas chamber is projected upon the microchannel plate and the output image is then collimated by an appropriate array of lenses onto the CCD.

The use of a microchannel plate has two further advantages. First, it is an easily gated device and it can be triggered by the high energy photon detected in the NaI(Tl)/PMT part of the apparatus. Second, it can be used to match the spectrum between the gas emitter and the CCD detector. More specifically, the input phosphor of the microchannel plate can be optimized to absorb the photons emitted by the gas discharge, whereas the output phosphor will be chosen to match the absorption spectrum of silicon.

Uses for MPD devices will now be discussed. The coincident gamma/x-ray detectors of the invention have applications in medicine and biochemistry, such as diagnostics, immunoassay, DNA sequencing, chromatography, and medical imaging. In addition, these techniques can be applied to such fields as pollution monitoring and detection, waste management, food quality testing, materials fabrication, chemical technology, and forensics.

Labelling: Preferred CGX isotopes have lifetimes between a few hours to a few years. Isotopes with half lives longer than two days are most preferred.

The CGX isotopes are chemically diverse, including many multivalent metals. Some form covalent bonds. Radioisotopes forming covalent bonds have been utilized for years in organic and biochemical analyses. In recent years multivalent metals have also entered service as labels. They are captured in chelating complexes which are constituents of, or can be adducted to, molecules or macromolecules to be quantitated. In addition the metal scavenging protein metallothionine can capture 20–40 atoms of multivalent metals. Metallothionine has recently been used as a constituent of genetically engineered fusion proteins. Its high carrying capacity is thus coupled, for example, with the targeting specificity of antibodies. A highly selective delivery of label to particular antigenic targets within complex cellular mixtures can thus be achieved. Thus, labelling strategies known to the practitioner may be employed with CGX isotopes according to the invention.

With an MPD optimized for rejection of events lacking the $I^{125}$ coincident CGX signature, the background uncertainty is only one count per day (1 cpd). Consequently, a picoCurie (pCi) input of $I^{125}$ will suffice for each sample in a typical assay protocol, three orders of magnitude (a thousand fold) less radioactivity than in prior devices. These pCi activities are much below the ambient radioactivity.

The CGX emitter may be coupled to an organic molecule, such as an organic precursor for the synthesis of a macromolecule, a steroid compound (e.g., estrogen), a protein, or a precursor of nucleic acids, biologically or synthetically produced. The CGX emitter may be incorporated in a primer for nucleic chain elongation, and used in an in vitro nucleic acid amplification protocol, or in the polymerase chain reaction (PCR) process, wherein the polymerase chain reaction can be stopped while the amplification is still exponential, after less then about ten amplification cycles. The primer may also be used in a linear polymerase reaction.

The CGX emitter may also be coupled to a monoclonal or polyclonal antibody or an antigen, and the antibody or antigen can be used in a competitive assay. For example, an antibody can be used to detect cancerous cells in a physiological sample. The level of estrogen and other steroids may be used to diagnose breast cancer.

The CGX emitter may be coupled to a unicellular organism such as a virus, a bacterial cell, an algae cell, a fungal cell, or a protozoa. The virus may be an agent of sexually or blood transfusion transmitted disease, and the bacteria may be tubercular bacillus or bacteria which are precursors of sexually transmitted diseases.

The competitive assay may be used to detect contamination of human physiological fluids such as blood, urine, sputum, tear drops, sweat, amniotic fluid or spinal fluid, or animal physiological fluids.

The competitive assay may be used to detect contamination of food and agricultural products, such as the presence of microorganisms and their toxic byproducts, e.g., aflatoxins or mycotoxins. The competitive assay may also be used to detect contamination of samples of water, soil or air from the environment, and chemical contamination such as pesticides, herbicides, PCBs, dioxin, and heavy metals.

The competitive assay can be performed upon airborne substances in a clean room environment, and data used to estimate the number and size distribution of micron sized dust and other particulates suspended in the air.

Diagnostics: Diagnostic applications of the invention include DNA sequencing, DNA fingerprinting and diverse forms of competitive and/or binding assays, e.g., radioimmunoassay (RIA). Using pCi levels of $I^{125}$ isotope inputs exposure to toxins and pathogens which may be resident in assay samples or reagents are a far greater safety concern than the minute amount of $I^{125}$ used.

This system can be used to quantitate sub-attomole ($<10^{-18}$M) amounts of biomolecules in diagnostic tests such as IAs, immuno-PCR and DNA probes, and IRMAs. To obtain an appropriate signal to background ratio (S/B) in the face of 1 cps background levels, previous IRMAs have required the use of hazardous quantities of radioisotope. Due to the absence of approved disposal sites, radioactive waste must be stored at the sites that generate the waste (i.e., hospitals, universities and industries), creating potential radiation and bio-hazards. According to the invention, solid assay residuals can be discarded subject only to biohazard regulations, as they are less radioactive than the environmental background. Liquid residuals will contain most of the radioactivity, but at lower activity than those from current biomedical procedures, e.g., radioimmunoassays (RIA) and typically much below the radioactive level of ground water. Thus, immediate disposal will probably be allowed in many cases.

Polymerase chain reaction: In the polymerase chain reaction (PCR), pre-existing knowledge of nucleic acid sequence is utilized to ascertain whether a target sequence is resident in a complex nucleic acid mixture, for example, a single HIV virus in a population of human cells. A cyclic replication reaction selectively amplifies the target sequence, until the amplified nucleic acids can be quantitated by some end point analytical technique. A practical problem is that artifactual products are unavoidably generated. Some of these artifacts are amplified faster than the target sequence. The more amplification cycles, the greater the probability the sought target signal will be swamped. Thus, minimizing the number of PCR cycles increases the signal/noise ratio of target/artifact nucleic acids.

The PCR reaction is compatible with CGX labeling. For example the primers for each reaction cycle could carry $I^{125}$ labels. Many fewer amplification cycles, with concomitant limitation in PCR artifact accumulation, would then suffice when MPD technology is used in the endpoint quantitation. These same advantages can be conferred to a number of other amplification strategies which are becoming competitive with PCR.

Multicolor application: An MPD device retains the capacity of simpler multichannel analyzer-based single gamma counters to discriminate co-resident isotopes when the known gamma energies of the sources are distinguishable. In addition, the separate characterization of the X-ray provides a further criteria for discriminating source isotopes in mixtures. Thus the MPD supports the simultaneous quantitation of more complex isotopic mixtures than simpler counters. Only menu driven changes in the software described below are needed to select for the known isotopes in a mixture. For brevity, this simultaneous quantitation capacity will be hereafter referred to as "imulticolor" capacity.

Imaging application: The invention may be applied in a spatially resolving radiation detector with imaging capability. Unlike X-ray film, spatially resolving CGX detectors must report the arrival time of radiation and thereby support background suppression by coincidence counting. These applications employ spatially resolving semiconducting detectors and spatially resolving gas detectors.

One can also use scintillators with appropriately coupled spatially resolving photon detectors, e.g., imaging photomultiplier tubes (PMT's) and CCD's. For example, imaging PMT's are designed to locate absorption sites on a single planar scintillator by providing the output of four channels within a single PMT. The burst of low energy photons resulting from stoppage of an energetic particle in the scintillator is distributed among the separate parts of the PMT. The appropriately analyzed outputs of the four channels provides for location of the absorption site on the scintillator. The quantitative imaging of a two-dimensional (2D) isotope source is thus supported. A regular array of samples spotted on a thin support membrane can represent hundreds of assay samples to be simultaneously quantitated. Imaging PMT's are compatible with the selective CGX counting strategy as further described below. Thus a low count rate of individual, low activity CGX samples can be compensated for by quantitating numerous samples in parallel. Even higher spatial resolution can be achieved when CCD's are coupled to the scintillator.

A spatially resolving MPD can be used where autoradiography has traditionally been employed, with the added advantage of multicolor capability. With conventional label detection techniques such as chemiluminescence or conventional autoradiography, any superimposed target distributions must be read out through sequential interrogation cycles. In many applications, the 2D target pattern is transferred to a durable membrane, producing a tough 2D blotted representative of the original 2D specimen, the blot. In other protocols, dot blots are produced by spotting nucleic acid or protein samples onto a membrane, and stably fixing them thereupon. Commonly, different analytical reagents must be used to display/quantitate various targets of a 2D pattern. Sequential interrogations are employed. This process is tedious and the frequent handling of the specimen or its blot membrane image limits its usable life span. With MPD probes for the distinct targets can carry distinguishing labels. The co-resident target distributions can thus be measured individually but simultaneously.

When the 2D specimen holds antigens (Ag), several antibodies (Ab) with distinguishing CGX labels can be separately prepared and then pooled for simultaneous interrogation of the blot. Conversely, antibodies can be bound on the 2D specimen and the positions displayed with a number of antigens carrying distinguishing CGX labels. These two formats together support a variety of immunoassays.

When the 2D specimen has bound nucleic acids (DNA or RNA), nucleic acid probes complementary to particular target sequences can be separately CGX-labeled and then pooled for simultaneous interrogation. These formats support protocols of sequencing by hybridization (SBH) with short oligomer probes, and both multiplex sequencing and genomic sequencing in which multiple fractionated products of DNA sequencing reactions are superimposed.

The sensitivity of these immunological techniques will be further enhanced by the use of CGXD, which can reach sensitivity levels previously achieved only with more difficult techniques such as PCR. This extra sensitivity is very useful in biomedical applications requiring sensitivity to a few hundred molecules. These applications include searches for the most potent toxins and some microorganisms. The sensitivity of CGXD may permit detection of a single virus or bacterium in a few milliliters of physiological fluid. It can considerably facilitate the detection of metastasis of diverse cancers, e.g., breast cancer. The improved sensitivity to toxins, e.g., aflatoxins and mycotoxins, will permit better quality monitoring during food processing, including storage of grains and other agricultural products.

Tracer diagnostics: A new family of applications made possible by the ultralow background capabilities of the invention is the deliberate introduction of radioisotopes or ionizing radiation into the human body. Previously, such introduction has been considered hazardous and is performed for tumor destruction, or when the value of diagnostic information obtained from the radiation is considered to far outweigh the dangers of the radiation itself. The human body, however, carries a natural background radiation level. For example, physiological fluids include $K^{40}$, and there are absorbed radon gas and its decay daughters, penetrating cosmic rays and traces of heavy radioactive elements.

With the MPD systems according to the invention, selected EC isotopes can be accurately quantitated at such low activities that they do not constitute a significant increment to the "natural" burden of ionizing events and cause no concern of inducing damage above the normal level. This opens a whole family of diagnostics for routine use, which could before only be justified for use with severely compromised patients.

Environmental applications: CGX isotopes or CGX labeled compounds could be released in the external environment as tracers, when the added radioactivity is far less than of the "natural" sources. For a particular example, the CGX tracers could be added to containers or piping to assess leakage. The unreactive noble gas $Ar^{37}$ is ideal for this purpose. Chemical tank farms, railway and highway tank cars and production plants with toxic chemicals are obvious markets. Other soluble tracers could be used where the surrounding ground/waters have already been so badly contaminated that the continuing slow leaks from tanks or pipelines are difficult to locate. The family of CGX isotopes includes several relatively short lived isotopes, so that even its small added radiation burden would very quickly disappear from the environment.

Quantitative measurement of the distribution of target substances in the environment, such as toxins or residual pesticides on crops can be achieved through immunoassay techniques. Greatest sensitivity is achieved by radioimmune assays, commonly using $I^{125}$ as a label on either antibody or antigen reagents. The CGX labeling of reagents and CGXD readout will extend the sensitivity of such assays, where they have in the past been limited by the radiation background. Antibodies have now been raised against many carcinogens, herbicides and pesticides.

In environmental monitoring, thousands of samples are studied to assess whether or not the contamination by a given pollutant is above the permissible level. These levels are typically around a picomole/ml, i.e., about three orders of magnitude higher than the limit of sensitivity of good immunoassays. Thus, one can pool hundreds of samples together and by testing the resulting "cocktail" check if any of the samples is contaminated. In the rare cases of cocktails showing positive, statistical techniques based on "Boltzano division" permits one to define which samples are actually contaminated in a relatively small number of steps. Thus, instead of measuring thousands of samples, typically a few dozen appropriate cocktails are measured, diminishing the cost by a factor of at least twenty. This technique is reliable only if the sensitivity of the assay is a factor of a thousand greater than the permissible contamination levels. The superior sensitivity of the MPD supports this methodology.

In natural environments, local patterns of water flow and soil inhomogeneities can lead to concentrations of contaminants in a few "hot spots" which are often only a few meters in diameter. Thus the range of the contamination levels is as high as a few thousand fold. On the other hand, within a square kilometer very few hot spots may exist, resulting in only one per thousand or fewer samples testing positive for the contamination. Current techniques, especially mass spectroscopy (MS) and high performance liquid chromatography (HPLC), test one sample at a time. The compatibility of CGX isotopes with 2D imaging permits measurement of hundreds of samples concurrently while maintaining extreme background rejection and hence the required high dynamic range to be sensitive both to hot spots and clean spots.

Clean room monitoring: The superior sensitivity of the coincident gamma X-ray detection technique and the specificity of competitive assay technology permits considerable improvements when used in "clean room" applications. The development of very high density VLSI chips requires increasing levels of purity in clean rooms used in semiconductor fabrication. The problem of defects due to contamination in the clean room environment is one of the crucial limits to high yields in the production of next generation chips. New monitoring methods to assess the air/chemical purity have to be developed to achieve the goals of next generation semiconductor fabrication. The majority of contaminants are biological in origin, e.g., parts of human skin, hairs, strands of material from clothing, bacteria, pollen etc. for which very specific monoclonal and polyclonal antibodies either already exist or can be developed.

Using the instruments of the invention, contamination by a few sub-micron sized particles per cubic meter can be detected. For example, when using a single monoclonal antibody, parts of human skin can be detected at $10^{-15}$ mole. The limitations are due to the specificity of currently used immunoassays. Various typical contaminants can be quantitated in parallel, using "multicolor" assays. The utility of immunoassays in clean room diagnostics can be considerably improved by using a plurality of monoclonal antibodies concurrently. The invention provides an analytical technique able to quantitate low levels with high throughput.

Advantages of a "sandwich" detector geometry are now discussed. One element of devices according to the invention is "sandwich" geometry, in which a single sample is placed between two independent scintillator detectors, each read-out by a separate PMT or equivalent. Sandwich geometry is counterintuitive because it leads to twice the number of elements, including PMT's, which are a major source of background. Furthermore, passive shielding is considerably more costly and the overall shape of the detector assembly is somewhat awkward, clearly diminishing user friendliness. Finally, sandwich geometry diminishes detection efficiency as compared to well geometry.

However, the use of sandwich geometry represents an optimal trade-off among several requirements:
  the ability to operate both in OR (non-coincident) and AND (coincident) modes;
  geometry permitting an asymmetric detector configuration;
  minimization and/or calibration of absorbtion artifacts; and A major source of background counts in scintillator-based gamma counters is radioactive contamination of the components of the detector itself. To reduce the actual radioactive component of the background the volume of the scintillator may be optimized. The low energy gamma and X-rays associated with $I^{125}$ decays are effectively stopped in less than 1 mm of NaI(Tl) or 1.5 mm of $CaF_2$(Eu) scintillator. However, producing a well detector with such thin walls is impractical, especially given the need to couple a PMT to the scintillator. Instead, a flat scintillator geometry is preferred even though it has somewhat lower detection efficiency. In practice, the detection efficiency of 2" diameter flat detectors is about 40% for a small (few mm diameter) source placed in the middle of the detector. The overall detection efficiency of the system is improved and made less dependent on geometry by using two identical flat round detectors with the source placed between them.

Segmentation of the detector has other benefits as well. It provides the ability in half the cases to distinguish 2-photon events from single photon events with double the photon energy. It also provides the ability to discriminate background by using anticoincidence rejection techniques. However, each detector module has a separate PMT, which increases the non-radioactive background component due to PMT dark pulses and various electronic artifacts. Therefore, effective discrimination of such non-radioactive events by pulse shape analysis in accordance with the invention is preferred. The sandwich detector geometry permits better performance than either well detector or flat detector geometries. The qualitative properties of scintillator detectors built with these three different geometries are shown in Table 2.

TABLE 2

| Detector | Detection efficiency | Energy resolution | Background |
| --- | --- | --- | --- |
| Well type detectors | very good ($\geq 50\%$) | fair | poor |
| Flat type detectors | poor ($\leq 40\%$) | good | good |
| Sandwich type detectors | good ($\geq 50\%$) | good | excellent |

Reproducibility and reliability are important features for biomedical instruments. In many detectors, typical sources of uncertainty are self-absorption and errors due to variations in the sample positioning inside/in front of the detector. These errors are easier to minimize when the sample is a liquid, and in this case the use of a well geometry has considerable advantages. Unfortunately, use of liquids leads to non trivial sample handling problems. Modern diagnostic methods often use formats in which the biological samples are attached to a solid surface or are products of a separation process which are adsorbed onto appropriate filters. For example, electrophoresis products are trapped in the gel or transferred to membranes. Detectors with flat geometry are advantageous when samples with a large surface/volume ratio are used, especially when biological samples are distributed inhomogeneously inside of, or attached upon, the surface of a solid state filter, support, or membrane with a non-negligible thickness.

Quantitation artifacts can be considerably diminished when using two essentially identical flat detectors, each with independent read-out electronics in accordance with the invention. When self-absorption is negligible and the placement of the sample is correct, both detectors give essentially the same count rate. However, even when the count rate is different in both detectors, the sandwich geometry permits the use of highly efficient differentiation/compensation schemes.

There are other advantages to using a sandwich geometry in accordance with the invention, especially for efficient background rejection. Many background events are due to electromagnetic pick-up and dark pulses in PMT's. With two well-separated detectors a significant part of the electromagnetic pick-up can be detected by comparing the pulses in both detectors. Thus, a pair of detectors with separate but identical electronics can be operated in an anti-coincidence mode to reject electronic and vibrational pick-up.

Background due to $K^{40}$ contamination within the PMT's is an important component of the total background in a single detector configuration. When two flat detectors are used, the energy deposited in one detector is often very different from the energy deposited in the second detector, which permits rejection of the background due to beta emitters contaminating scintillators, PMT's and shields. The use of appropriate separators permits further elimination of background due to high energy photons penetrating from outside the device. It is also useful in rejecting cosmic rays.

Another important advantage of the sandwich geometry according to the present invention is its versatility. A preferred implementation of the invention uses two essentially identical detectors for the detection of the isotope $I^{125}$. The case of $I^{125}$ is somewhat an exception, i.e., multiple photons are emitted in coincidence, but their energies are very close, namely E=27, 31 and 35 keV. Thus, for $I^{125}$, two identical thin scintillators can be used. However, many other important sources emit multiple photons of quite different energies; often one photon is a soft X-ray (E<50 keV) while the second photon is a nuclear gamma-ray, e.g., E>100 keV. For example, this is the case for $^{123}I$, which has three lines at 27 keV, 31 keV and 150 keV respectively. In this case, a sandwich detector according to an embodiment of the invention having two scintillators with different crystal thickness would be optimal. Further, photoswitch elements can be used for detection of photons of significantly different energies.

When using scintillator detectors, it is appropriate to physically isolate the scintillators as much as possible to reduce induced X-ray crosstalk between them. If the volume of the samples is relatively small (a few hundred microliters) this can be achieved by incorporating a 1–5 mm thick sheet of lead or copper into the sample holder. Isolation of the detectors effectively reduces the background in the single-photon $I^{125}$ energy region of interest (ROI) twofold. Detector isolation has much less effect on the background in $CaF_2(Eu)$-based systems because these detectors do not produce secondary X-rays in the $I^{125}$ ROI. The use of $CaF_2(Eu)$ facilitates construction of MPD detectors in accordance with the invention for samples with large volume. NaI(Tl) or CsI(Tl) based detectors show considerable sensitivity to the geometry and diameter of opening in the separator.

Comparisons of a device according to the invention with the detectors at Memorial Sloan Kettering Cancer Center (MSKCC) and elsewhere were performed using binary dilutions of commercially available radio-iodinated TSH antibodies. The molecular weight of this antibody is about 40,000 daltons. Most of the tests were performed using a calibration sample set. Additional calibration runs used water dilutions of $NaI^{125}$ and $I^{125}$-dCTP. For radioactive standards, ethidium bromide was iodinated with $I^{125}$ to a specific activity of about 0.1 mCi/mL. It was subsequently sequentially diluted by factors of four with isopropyl alcohol. The calibration set includes ten samples, covering the range from a few thousand dpm to about 0.1 dpm. Hundred microliter volumes of each dilution were placed in 200 microliter Eppendorf vials made of a thin plastic.

Results of these comparisons confirmed that the MPD permits measurement of lower amounts of radioactivity than other gamma detectors. The detection efficiency and energy resolution of two different MPD detectors was also compared. In non-coincident mode, MPD devices according to different embodiments of the invention had comparable detection efficiency and about 50 times lower radioactive background as compared to conventional devices. Also, the conventional systems are calibrated to about ±5% wherein our MPD is calibrated to within ±1%.

Table 3 shows some of the most important parameters, namely detection efficiency and background, for a plurality of commercial gamma counters and two MPD detectors according to the invention based on NaI(Tl) and $CaF_2$ (Eu), respectively. Table 3 also shows that for an MPD device in an AND mode, when coincidence between two photons emitted by an EC source is used, the background is further diminished as compared to an OR (non-coincident) mode, which leads to considerable increased sensitivity. However, some reduction of detection efficiency is observed in the coincident mode.

TABLE 3

| Detector | Detector Efficiency | Background for $I^{125}$ (cpm) |
| --- | --- | --- |
| Gamma-counter (1) | 70% | 200 |
| Gamma-counter (2) | 80% | 150 |
| Gamma-counter (3) | 50% | 60 |
| Gamma-counter (4) | 50% | 60 |
| MPD1[NaI(Tl)] (5) | 60% (10%) | 2 (0.1 cpd) |
| MPD2[CaF$_2$(Eu)] (6) | 50% (5%) | 1.5 (0.3 cph) |

(1) Beckman 5500 at American Red Cross, Gaithersburg, Md.;
(2) Beckman 5500 Gamma Counter at Lehigh University, Bethelheim, Pa.;
(3) Gammascope LKB 1272 at Georgetown University, Washington D.C.;
(4) Gammascope LKB 1292 at MSKCC, New York, NY;
(5) MPD based on two 2" NaI(Tl) scintillators;
(6) MPD based on two 2" CaF$_2$(Eu) scintillators.

For the MPD detectors, performance is given in both OR and AND counting modes (values in parentheses are the AND mode values).

Optimization of MPD systems permitting both OR and AND modes of operation according to the present invention will now be discussed. Sandwich detectors allow a coincident (AND) mode of operation, thus dramatically reducing the background by orders of magnitude. However, the detection efficiency for this acquisition mode is relatively low (5 to 15% for $I^{125}$ sources and 2" to 3" diameter detectors in a sandwich geometry) which considerably extends counting times for low-activity sources. However, sandwich detectors according to the invention can also operate in a non-coincident mode, which is referred to as an OR mode. In this OR mode, an event registered in either of the detectors is counted. Thus, the whole system works as one detector, similar in this respect to a well detector or any non-segmented detector. In the OR mode, the detection efficiency is higher (typically, 50% for $I^{125}$ sources and 2" diameter detectors in a sandwich geometry), but the additional benefits of better background rejection through coincidence are lost.

An MPD in accordance with the invention operated in the OR mode achieves considerable background reduction through the use of: optimal scintillator thickness; correct interpretation of a fraction of two-photon events (50% for a two-detector system) which allows reducing the counting region of interest to the single-photon peak; anticoincidence; and pulse shape analysis.

In a 2" diameter CaF$_2$(Eu) crystal MPD the background in the OR mode is 1.5 to 2 cpm and the detection efficiency is 50%. During the OR mode acquisition, coincident events are identified and counted, thus avoiding the need for separate AND mode counting. Upon completion of the acquisition, the MPD outputs both OR and AND counting data. The OR data should be used if the activity of the source is above the OR background equivalent activity (about 5 picoCurie, or 2 attomole of $I^{125}$ label). These data have a lower statistical uncertainty due to the higher detection efficiency of OR counting. If the OR counts are close to the OR mode background, the AND mode counting data is used, due to its much lower background.

As a rule of thumb, the OR mode of operation is better for sources larger than 10 dpm, i.e., about 5 picoCurie. However, in the activity range of 1–20 dpm both OR and AND counting modes are beneficially used. For this range of sensitivity, software is used combines the OR and AND data to obtain the best estimators of the true count rate. This permits minimizing the artifacts due to statistical uncertainty (AND data) and high background (OR data). Below 1 dpm, the AND mode gives a reasonably better signal to background ratio.

One of the important software functions according to the invention is to properly estimate the dead-time and pile-up corrections to the counting rate. The DSO-based acquisition of pulses involves a relatively large amount of dead time, which has to be compensated for, in particular, for high count rates. In MPD devices according to the present invention, this is done using an additional counter/timer card.

The counter/timer card preferably has at least two pulse counters and a timer. One counter should count all hardware triggers formed by the signal conditioning/triggering card, and the other should count coincident triggers only. The timer should keep track of the exposed time with good precision. In the preferred implementation, model PCL-720, distributed by JDR Microdevices, is used. This card has 3 counters, one of which can be converted into a timer by internal wiring. The counters are 16-bit, so they should be read out at least once a second to prevent loss of data. The third counter is wired to count time in intervals of $\frac{1}{2,500}$ of a second in this embodiment.

When counting is initiated, the MPD software arms the DSO card for acquisition of the first pulse and simultaneously initiates the counters and timer. Every time the PC hardware timer interrupt comes (e.g., every 55 milliseconds) the values of the counters and the timer are read out and added to the total counts/time elapsed. Upon completion of the counting, the count rate in the appropriate counter (total counts divided by the time read from the timer; the coincident trigger counter is used if the DSO is triggered by coincident triggers, the total counts counter otherwise) is used to adjust the count rates of all events, non-rejected events and events in all regions of interest (ROI's) using the formula:

$$Cpm_{i\ Adj} = Cpm_i * (Cpm_{Total\ Counters} / Cpm_{Total\ DSO}),$$

where $Cpm_{i\ Adj}$ is the count rate (per minute) for the ith ROI, adjusted for dead time losses, $Cpm_i$ is the raw DSO cpm for the ith ROI, $Cpm_{Total\ Counters}$ is the total cpm in the counter, and $Cpm_{Total\ DSO}$ is the total count rate before rejection in the DSO.

This adjustment allows full compensation for dead time losses, and effectively makes the linearity of count to be limited only by the pulse pile-up at high count rates. The self-calibration program permits concordance of the OR and AND counting rate data to, for example, within less than three percent.

Performance characteristics of CGX detectors will now be discussed. Detectors according to the invention have radically improved performance when compared to conventional devices. The improvements include sensitivity, reproduceability, and dynamic range.

Sensitivity: A direct indicator of the sensitivity (or limit of detection) of a radiation counter is its background equivalent activity (BEA), i.e., the activity of a source which would produce a count rate equal to the background in the detector. This figure of merit accounts for both the background and the detection efficiency of a counter.

The typical BEA for MPD detectors in accordance with the presen invention in an OR mode (non-coincident detection) is in the range of 3 to 4 decays per minute, which is equivalent to less than 2 picoCurie of $I^{125}$. This is based on a detection efficiency (DE) in the OR mode of approximately 50% and a background count rate in the $I^{125}$ energy region of interest of 1.5 to 2 cpm. Thus, a 5 picoCurie sample will have a S/B of about 3.

The typical BEA for MPD detectors according to the present invention in an AND mode (coincidence detection) is in the range of 1 decay per day, which is equivalent to a few femtoCurie. This is based on a DE in the AND mode of about 7% and a background count rate in the $I^{125}$ region of interest of 1 count per two weeks.

For a small activity source (10 picoCurie), commercially available detectors are either unable to quantitate the sample or provide marginal measurement with S/B close to one. However, a 10 picoCurie $I^{125}$ sample was repeatedly measured with a CGX detector according to the invention, 400 times over a few weeks period. The measured activities are compatible with the known half-life of $I^{125}$. These measurements were obtained using the OR mode of operation, in which coincidence is not employed.

In an enhanced performance mode, which is based on coincidence, and more stringent pulse shape analysis, the DE is somewhat lower (5–10% vs. 50%), while the background is lower by a few orders of magnitude. For this enhanced mode, the performance depends on the sample size. For standard 12 mm diameter sample tubes, the DE is 6.5% and the background is 0.25 cph, yielding a BEA of 4 dph. For small samples (4 mm in diameter or less), the DE is 5–7% and the background is 0.5–1 count per week which is equivalent to a BEA of 3 dpd (decays per day). In this enhanced sensitivity mode it is thus possible to detect $I^{125}$ sources with activities of about 10 dpd, i.e., containing less than a thousand $I^{125}$ atoms.

Reproducibility: Exceptional reproducibility of measurements with MPD devices according to the invention has been achieved by selecting electronic elements with very low temperature coefficients; partial compensation of scintillator [$CaF_2(Eu)$] temperature response; rejection of dark pulses due to cosmic rays, and rejection of electromagnetic interferences.

All these effects are known to be time-dependent. For example, the temperature dependence of the signal from scintillators leads to day/night effects on the level of 3–5% in conventional commercial gamma detectors. At low countrates the diurnal and annual modulation of the flux of cosmic rays leads to a few percent effects in well detectors. Finally, sensitivity to electromagnetic interference leads, at activities below 10 cpm, to noticeable day/night changes. The rejection/compensation of these effects in the MPD considerably improved measurement reproducibility and removed all diurnal effects.

The measurement reproducibility of MPD devices according to the invention is determined primarily by counting statistics, clock accuracy, and the reproducibility of placing the sample within the instrument. MPD devices according to the invention are reasonably stable over the long term. No variations in background have been observed, and the detection efficiency is stable. To test the measurement stability of an MPD device over a few weeks, the same sample (50 nanoCurie) was counted about 1,200 times, removing and replacing it in the holder before each measurement. For each measurement the sample was counted until 10,000 counts were accumulated (equivalent to a statistical uncertainty of ±1%).

Another advantage of the MPD according to the present invention is the possibility of reliable calibration. Improved calibration is possible due to use of the "sandwich" geometry which diminishes absorption and sample placement artifacts, and the use of $I^{125}$, permitting use of the Eldridge calibration procedure. For example, the same MPD device was calibrated 25 times with a 50 nanoCurie source. The average DE was determined to be 49.1% with a standard deviation of ±1.7%. In comparison, the typical commercially available detectors are nominally calibrated to within ±5% but in reality for sources with activity below 0.1 nanoCurie, the calibration uncertainty is closer to ±10%.

Dynamic range: Linearity over many orders of magnitude is a desirable feature for all analytical and biomedical applications. Often, the levels of primary biocompound should be compared with the level of metabolites, which can be many orders of magnitude lower. The majority of currently used conventional instruments have very limited dynamic range.

Photographic emulsions permit quantitative measurements only over 1.5 logs range. Typically, the response of the detectors is limited both at low levels and at high counting rates. Thus, instead of the desired linear response, the characteristic detector's response is an S-shaped curve. At low count rates, well detectors are seriously limited by the intrinsic background. Similarly, optical detectors, e.g., color spectrometers, are severely limited by photonic background. At high activity levels, pile-up or optical interference distorts the linearity of conventional detectors. Actually, gamma detectors are close to ideal for high count rates, up to about 1,000,000 cps. Thus, typical well counters show a linear response over about 4 logs dynamic range, from about 100 cps to 1,000,000 cps.

Figure 4:
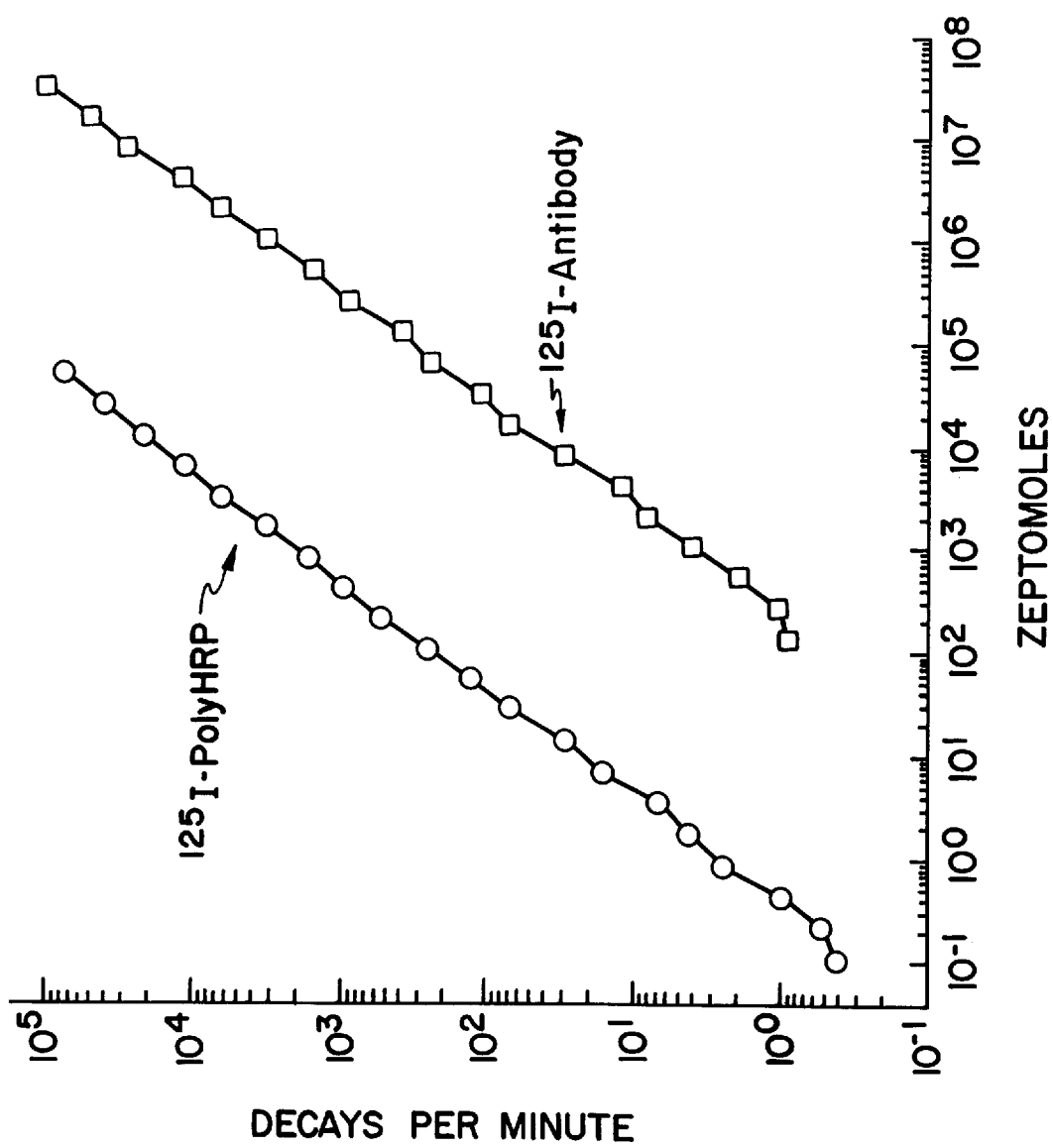
FIG. 4 graphs the dynamic range of an MPD according to the invention.

The background rejection techniques used in MPD devices according to the pressent invention permit reliable quantitation from 1 cpm to 1,000,000 cpm, i.e., over 6 logs dynamic range in the OR mode. When using the enhanced operation AND mode, for which the background is 1 cpd, the MPD detectors according to the present invention are linear over 9 logs dynamic range. At higher count rates (above 500,000 dpm), saturation may be caused by pulse pile-up in the scintillator. Although the response is no longer linear in this range, the dead time of the MPD is non-extendable, so that counting can be performed and the results corrected for pile-up. At low count rates, the linearity of response is limited by the background. The results of measurement using MPD are shown in FIG. 4. Dilutions of $I^{125}$-labeled reagents show perfect linearity of measured activity over 5 orders of magnitude down to the 0.1 zeptomole/sample level.

Figure 5:
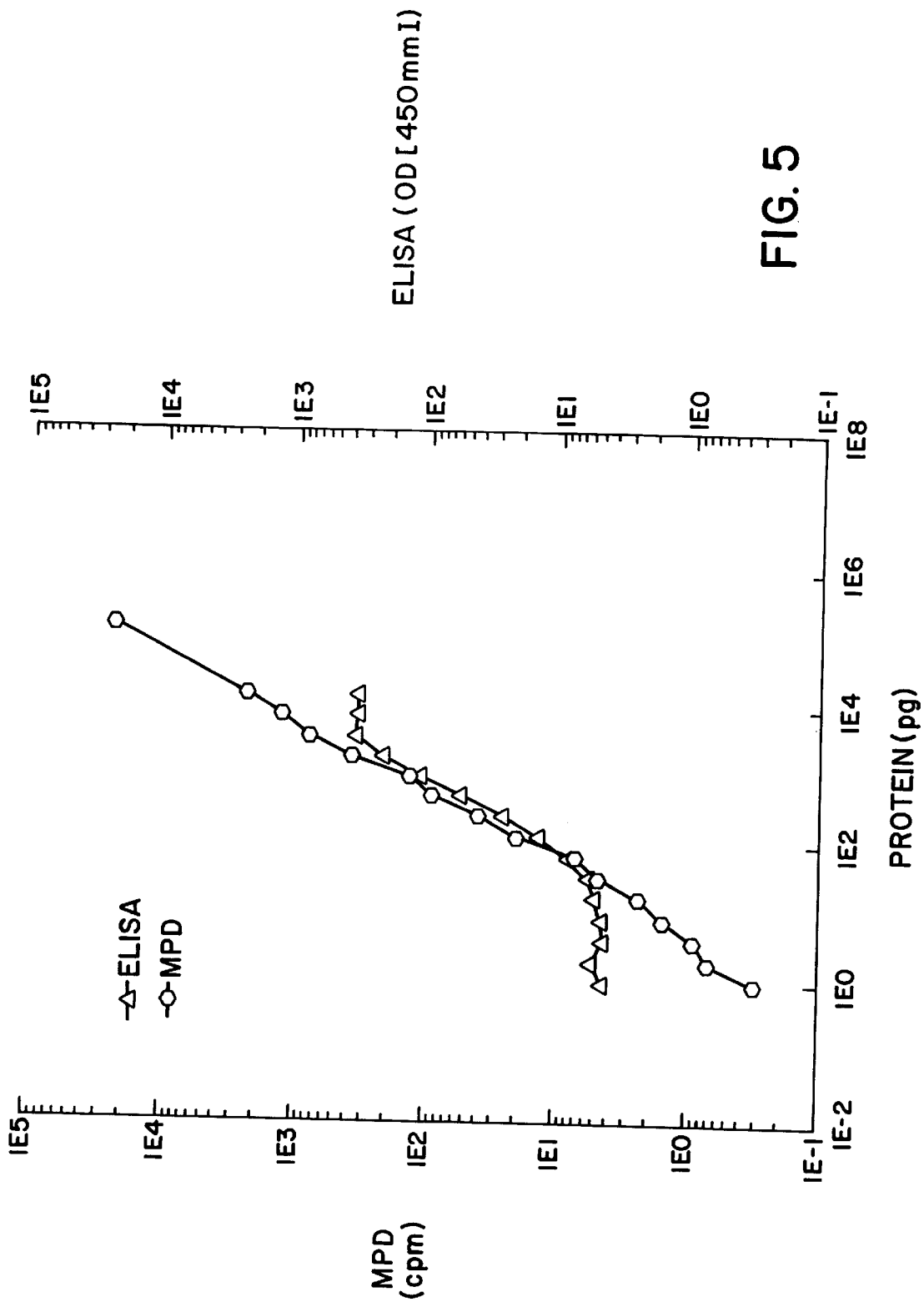
FIG. 5 shows the dynamic range of an MPD device compared to a color spectrometer.

The linearity of response of the MPD according to the present invention was compared with commercially available colorimetric detectors and the advantage of the MPD is evident. The dynamic range of the MPD detector is considerably better than for color spectrometers. To perform this study, streptavidin-HRP was iodinated and the same sample was measured using MPD and a commercial color spectrometer used for ELISA tests. The results are presented in FIG. 5. The sensitivity of the MPD is at least two orders of magnitude better than that of the color spectrometer, and its dynamic range is about five orders of magnitude better. In the range where the color spectrometers work reliably, identical results were obtained using the MPD according to the present invention and the color spectrometers.

Use of $CaF_2(Eu)$ scintillators is now discussed. NaI(Tl) scintillator crystals seem a natural choice for MPD instruments. In coincident mode, background rejection is inversely proportional to the square of the energy resolution, which for NaI(Tl) is about 50% better than for other scintillators. Furthermore, among scintillators with reasonable energy resolution (NaI(Tl), CsI(Tl) and $CaF_2(Eu)$), sodium iodide scintillators are fastest. According to standard practice, background rejection is proportional to the square of the timing resolution. Estimates suggest that the background in an MPD based on NaI(Tl) should be about four times lower than when using other scintillators, and such an MPD system for very small, say <10 microliter sources, achieved a background of about 0.5 count per week (0.5 cpw).

However, disadvantages of NaI(Tl) based devices include:

NaI(Tl) is mechanically fragile, e.g., it often cracks when submitted to temperature gradients and/or during transportation;

NaI(Tl) must be hermetically sealed, and the thin Al or Be foil covering the front surface of the scintillator is easy to rip off when samples are placed in its vicinity, e.g., when operating spatially resolving MPD devices;

When larger samples are used, the background in MPD systems based on NaI(Tl) significantly deteriorates due to X-ray cross-talk between the crystals.

Replacing NaI(Tl) with other scintillators, including $CaF_2$(Eu), leads to a small increase of background. However, by optimizing read-out electronics and data processing software, for small samples of $I^{125}$ or $I^{123}$, $CaF_2$(Eu) based MPD systems reach almost the same background as NaI(Tl) based systems. For large samples, the background in $CaF_2$(Eu) based MPD systems is about a factor of ten better.

$CaF_2$(Eu) has the above mentioned surprisingly low background for $I^{125}$ detection for several counterintuitive reasons. First, for MPD systems according to the invention, the main source of background in the AND mode is the detection of a soft X-ray emitted and absorbed in one crystal coincident with some source of energy detected in the second crystal. When NaI(Tl) is used, any absorption of an external photon with E>35 keV in the crystal leads to remission of 26 keV or 32 keV photons from rearrangement of atomic shells. Thus, characteristic iodine X-rays are emitted when the NaI(Tl) crystal is used. These cannot be distinguished from the 25 and 31 keV Te X-rays emitted by either $I^{123}$ or $I^{125}$ daughter nucleii. Actually, for CsI(Tl) this effect is even bigger because the characteristic X-rays of both Cs and I are virtually the same as X-rays emitted by radioiodine. Fortunately, $CaF_2$(Eu) on the other hand includes only low atomic number elements. Thus, its characteristic X-rays have less than 15 keV energy and can be differentiated from radioiodine X-rays. Thus, preferably NaI(Tl) or CsI(Eu) should be used for EC radioisotopes with atomic number of either less than 40 or larger than 70. For EC isotopes with atomic number between 40 and 70, $CaF_2$ (Eu) is a preferred scintillator.

A second advantage of $CaF_2$(Eu) is even more subtle and counterintuitive. $CaF_2$(Eu) is a very slow scintillator with characteristic light decay of about 5 microseconds, i.e., about a factor of 25 slower than NaI(Tl). Conventional detectors used the fastest possible detectors, with backgrounds of about 1 cps. When background is pushed to a few cpm, the dominating sources of background are due to cosmic rays and dark current pulses from the PMT's. Spurious signals due to energy deposited by cosmic rays in the crystal itself can be partially accounted for by analyzing the amount of energy deposited. Particularly for low energy X-rays, e.g., for $I^{125}$, this method permits rejection of over 95% of cosmic rays crossing scintillators. This includes efficient rejection of secondary particles in the cosmic ray showers.

However, in the case of an MPD system, the crystals themselves are very thin and the surface of the PMT cathodes is about fifty times larger than the surface of the crystals. A high energy cosmic ray striking one of the PMT anodes gives rise to an avalanche of electrons which are subsequently amplified. Such pulses lead to an apparent energy deposition much lower than the energy of the cosmic ray, i.e., there is a considerable overlap between the energy spectrum of cosmic ray induced dark current pulses in the PMT's and the energy from radioiodine. In detectors using scintillator-PMT combinations this source of background accounts for a few counts per minute in each PMT, or a few counts per hour in the coincidence mode. However, the energy deposited in the scintillator typically leads to pulses longer than the cosmic induced pulses in the PMT, which have a characteristic time constant of about 0.2 nsec.

In practice, the rejection capability is limited by several detector characteristics. These include the characteristic response time of the scintillators, the parameters of the shaping amplifier, and the performance of the on-line pulse shape analysis system. For example, in MPD systems there is a trade off between the need for low cost and the performance of the on-line digital storage oscilloscope (DSO) used in pulse shape analyses. Only about half of the pulses induced in PMT's by cosmic rays can be rejected versus pulses induced in NaI(Tl). The difference in pulse rise times between cosmic ray induced PMT pulses and those created in $CaF_2$(Eu) is large, i.e., 0.1 nsec and a few microseconds respectively. In a $CaF_2$(Eu) based MPD system, over 95% of cosmic ray induced PMT artifacts are rejected on-line.

Changes were obeserved in NaI(Tl) crystal properties occurred over a 2 year period in about 40 NaI(Tl) crystals. Some (about 10%) crack from thermal stresses while others (about 15%) turn yellow due to their hygroscopic property. In contrast, no significant variability in crystal properties was observed for twenty $CaF_2$(Eu) crystals over a one year period.

In summary, $CaF_2$ (Eu) scintillators in sandwich geometry permit achievement of excellent background rejection, especially when large diameter samples of radioiodine are measured. The excellent mechanical properties of $CaF_2$(Eu) provide another advantage over NaI(Tl).

Selection of scintillators and their dimensions will now be described. Conventional scintillators are optimized to maximize the detection efficiency. Thus, the typical thickness selected is about twice the stopping power at the energy of interest. Also for typical sample sizes, say 0.5 inch in diameter, the diameter of the selected crystal is 3 or even 4 inches. However, background is roughly proportional to crystal volume in a complicated nonlinear function of scintillator dimensions. For example, for 3" crystals conventional designs couple them to 3" PMT's. However, 3" inch PMT's are considerably more radioactive than 2" PMT'S. This radioactivity originates from naturally occurring isotopes in the PMT glass. The larger surface area and greater thickness of the glass walls in larger PMT's thus leads to significantly higher radioactive background. Thus, against the conventional assumptions, to optimize the performance of low background MPD devices, 2" diameter detectors and substantially thinner crystals are preferred in the present invention.

MPD detectors according to the invention have the advantage that they can be self-calibrated for $I^{125}$ using two photon coincident detection. However, to accomplish this, the pair of detectors should be well matched, i.e., should have similar properties. To facilitate the selection of well matched pairs, all crystals within a given MPD system are preferably cut from the same large diameter crystal. The crystals are mounted in low radioactive background copper tubes. The X-ray window/reflector is made of MgO and 50 micron thick Al film. Optionally, thin TEFLON film is used. The optical window is made of at least 2 mm thick quartz.

Optimization of diameter and thickness: For single-sample MPD devices, according to the invention the optimum scintillator size was found to be 2" diameter. For this size the S/B is highest for the standard sandwich geometry, i.e., when a sample is placed between detectors spaced about ½" apart. However, the optimization curves as a function of crystal size are rather flat. For example, (S/B)[3"]~1.2. When optimizing MPD detectors for $I^{125}$, the optimum thickness of the scintillator is 1.5 mm for $CaF_2(Eu)$; a change of crystal thickness from 1.0 to 3.0 mm changes the (S/B) by only about 50%.

Selection criteria: Preferably, each crystal is optically inspected; crystals which are cracked or not perfectly transparent are rejected. The crystals are then mounted on selected low radioactive background PMT's and are submitted to a series of acceptance tests. The first test checks for the energy resolution and the detection efficiency of the whole crystal. Unfortunately, PMT's are far from being uniform, and the performance of different zones of the PMT should be measured. To do this, the surface of the scintillator/PMT assembly is shielded by rings of lead of increasing diameter with a radioactive source placed in the center. The first lead mask has a 0.5 cm hole. The energy resolution in the center of the scintillator/PMT is then checked. Two other lead masks are also used to check the energy resolution, a one inch and a two inch lead ring. Only $CaF_2(Eu)$ crystals with $dE/E(FWHM) \leq 21\%$ for $I^{125}$ are accepted. Furthermore their radioactive background must preferably be $\leq 0.05$ dpm. Typically two to three crystals from each batch of ten are rejected and returned to the producer.

Selection of low background PMT's and optically transparent material between the PMT and scintillator crystal is now described. MPD devices according to the invention require considerable care in the selection of PMT's. Custom made quartz PMT's are preferred if the additional cost is tolerable. Off-the-shelf integral scintillator/PMT assemblies and commercially available PMT bases may be used instead, with appropriate modifications in accordance with the invention. A large part of the radioactive background is due to the use of stainless steel in these integral assemblies, and commercially available PMT bases are quite radioactive. PMT bases according to the invention have a composite shield between the base and the PMT to diminish the radioactive background. Also, the PMT's are optically coupled to the scintillators via an appropriate low radioactive background optical coupler (quartz).

To diminish radioactive background in MPD systems, PMT's are selected which are optimal for both 2" and 3" scintillation crystals. The following PMT parameters are of importance: radioactive background, detection efficiency, energy resolution, homogeneity over the photocathode surface, dark current, long term stability, and dependence of signal on temperature and magnetic field.

Testing procedure and results: Candidate photomultipliers from five different manufacturers were tested, with the best results obtained for Electron Tubes, Inc. (ETI) and Hamamatsu PMT's. About 40 PMT's from these two manufacturers were tested for their electronic properties and radioactive contamination. The Hamamatsu PMT's provide marginally better electronic performance. They feature both an excellent detection efficiency and good energy resolution. Also, their dark current is somewhat lower. However, for both 2" and 3" tubes, the best individual tubes were from ETI. These tubes have a somewhat larger distribution of electronic performance within the batch. Concerning the radioactive background, the ETI tubes are preferred; measured backgrounds were a factor of ten lower than for Hamamatsu tubes, for example.

The PMT's are subjected to a series of tests to determine whether they meet the selection criteria. The first test checks for energy resolution and detection efficiency on an open faced crystal. Next, the energy resolution for the different parts of the PMT is checked. This is done by using three different lead apertures, in which a radioactive sample is placed. The first mask has a 0.5 cm hole and the second mask is a one inch outer lead ring. Electronic parameters are strongly dependent on the energy of the isotope used. For example, there is no correlation found between the energy resolution at about 30 keV ($I^{125}$ source) and at about 88 keV ($Ga^{67}$ source).

The relative radioactive background in the PMT's is measured by placing a PMT next to a 2" diameter, 2 mm thick $CaF_2(Eu)$ detector coupled to a selected low-background 2" PMT. The whole test system is well shielded with lead, tin and copper. The background in the $CaF_2(Eu)$ detector is measured in the energy range of 20 to 40 keV (the energy region of interest for $I^{125}$) and compared with the background without the studied PMT. Pulse shape analysis is used to discriminate between events and electronic artifacts. During testing the background in the $CaF_2(Eu)$ detector in the absence of the test PMT was found to be 0.7 cpm. ETI PMT's normally increased the count rate only insignificantly, while the Hamamatsu PMT's generally created a large additional background.

The radioactive background found in the Hamamatsu PMT's is surprisingly large; the average background is 3.5 cpm but values as high as 4.2 cpm were observed. Thus, selected 2" ETI Model 9266KB PMT's coupled to a NaI(Tl) or CaF(Eu) scintillator are preferred. The average dE/E (FWHM)=17.4% and the minimum and maximum energy resolution is 16.2% and 20.7%, respectively. The average detection efficiency is 37.4% with minimum and maximum values of 31.1% and 40.3%, respectively. The radioactive background due to the EMI PMT's is rather low; the average background is 0.2 cpm with minimum and maximum values of 0.1 cpm and 0.55 cpm, respectively. About 20% of PMT's were observed to have backgrounds higher than 0.3 cpm. After these were rejected, the average background is 0.13 cpm with minimum and maximum values of 0.11 cpm and 0.28 cpm, respectively. Another preferred model is ETI model R-2486 PMT.

Packaging: Conventional PMT's are typically packaged in prefabricated aluminum or stainless steel tubings. These commercially mounted PMT's have increased radioactive background and so a modified mounting is preferred. PMT's shall be checked for cracks or flaws. The PMT is washed with isopropyl alcohol to remove any particles or contaminants. Next, the glass surface with the exception of the window area is covered with four layers of black electrical tape. After this is complete, one spiral of black electrical tape covers all the bands except for the first (next to the window). Subsequently, two layers of copper foil tape with conductive adhesive cover the whole PMT, including the plastic base. Another spiral layer of black electrical tape covers the copper. Next, a single layer of copper foil tape followed by a single spiral layer of black tape completes the wrapping process.

The crystal is coupled to the PMT with silicon optical grease. Care is taken not to introduce air bubbles between the crystal and PMT. Next, white TEFLON tape is wrapped around the PMT where the crystal and the PMT meet. The crystal is held in place with four to eight strips of very thin adhesive aluminum foil. A layer of adhesive copper tape is placed around the crystal and PMT to secure the PMT and crystal together, while providing protection against external X-rays. The three inch PMT's have adhesive lead tape securing the two together. Finally, to ensure against visible photon leaks, a spiral layer of black electrical tape covers the copper.

For low-background counting the scintillators should be shielded from radioactivity in the photomultipliers to which they are coupled. It is impossible to shield the detectors from high-energy gamma rays from the PMT's without degrading the optical properties of the scintillator/PMT system. It is possible, however, to shield the scintillators from beta particles and low energy photons by using a transparent window such as quartz between the PMT and the scintillator. This window 24 is shown in the exemplary embodiment of FIG. 1, with optical grease layer 23. Quartz was selected both for its excellent optical properties and its high purity. Quartz matches the optical density of $CaF_2(Eu)$ very well and is acceptable for NaI(Tl). 5 mm thick quartz windows are preferred. There is no observable radioactive contamination in quartz.

Improved shielding of the scintillators from gamma and X-rays can be achieved using materials with higher stopping power than quartz. High-purity $GeO_2$ and germanium-based glasses are preferred for this purpose, for they have very low intrinsic radioactive background. Their higher atomic number and density is an advantage over quartz windows. Such windows with a few millimeters thickness efficiently stop low energy photons, as well as beta particles, without degrading the optical qualities of the scintillator/PMT systems. The optical properties of gelica and germanium glass match NaI(Tl) better than does quartz.

Another alternative is to use high density glasses based on lead, particularly high density transparent crystals such as $PbF_2$ and bismuth germanite (BGO). In the case of BGO, undoped crystals should be used so as not to generate artifacts due to scintillation within the BGO. The optical density of these materials is higher than for $CaF_2(Eu)$ or NaI(Tl). Thus, it is preferred to use a thin layer of special optical greases, e.g., powdered $PbF_2$ in silicon grease, to match the optical properties of the scintillator and window, and the window and PMT. Optionally, a window consisting of a triple sandwich consisting of gelica/high density window/gelica can be used. The thickness of the gelica may be much smaller than the high density optical window.

Shield/Separator: External shielding of an MPD according to the invention is required to stop ambient radiation, as shown in the exemplary embodiment of FIG. 1 as shield 55. A 2" thick Pb shield is adequate for MPD detectors built around 1–1.5 mm thick scintillator crystals. Increasing the shield thickness further does not significantly reduce the background on the Earth's surface, most probably because the remaining background is predominantly due to cosmic rays. However, if the shielding is made of lead only, secondary lead X-rays are present in the background spectra due to excitations in the shield itself by radioactive particles. Composite shielding is thus preferred, with a 1–5 mm thick layer of tin inside the Pb shield to absorb the lead X-rays and a 1–5 mm thick copper layer inside the tin layer to absorb the tin X-rays. The X-rays of the copper itself are of a sufficiently low energy (8 to 9 keV) to be outside the $I^{125}$ region of interest. Both NaI(Tl) and $CaF_2(Eu)$ scintillators have sufficient energy resolution to reject these pulses with better than 90% probability. Commercially available Cu foils are sufficiently pure and do not introduce additional radioactive background. The external shield should enclose the detector assemblies, including the PMT's and bases, on all sides.

Sample holder/crosstalk eliminators are also made of copper, lead, or composite copper/lead plates 1–5 mm thick. This thickness is sufficient to stop iodine X-rays.

The materials for the shield should be tested for the absence of radioactivity, by measuring the background in a $CaF_2(Eu)$ detector selected for low radioactive background and placed in a selected, low background shield. A test performed for 2 hours yields a statistical uncertainty for each point of about ±10%. Each shield which has a radioactive background larger than 0.9 cpm may be remeasured for 4 hours. If the new value is still above 0.9 cpm the shield is rejected. Typically, 20% of shields have to be rejected.

Integral PMT base assembly for high stability MPD devices is now described. Accurate counting of low activity sources requires a high stability detector system. The observed drifts are predominantly due to changes in ambient temperature, which cause drifts in the yield of the scintillators as well as the gains of the PMT's and the electronic readout. Improved electronics and high voltage power supply are preferred for stabilizing the PMT's.

The high voltage power supplies (HVPS) for the PMT's should be stabilized by introducing a high gain negative feedback, using as a reference chips (e.g., Max 580) with low temperature coefficient (1–2 ppm/degree Celsius), and using 1% metal film resistors with a low temperature coefficient. The voltage divider for the PMT is based on the same type of resistors. The temperature dependence of the preamplifiers is minimized by using highly stable op-amps and distributing the gain so that each amplifier cascade has a gain lower than 5.

The problem of long-term and temperature-induced drifts in the PMT's and scintillators can be compensated for by adjusting the gains of the amplifier, so that the acquired spectra are unchanged. Electronics permits digitally controlling these gains. When coupled with temperature readout devices placed in the detector system this allows continuously adjusting the gains to compensate for temperature induced drifts. The temperature-to-gain calibration for each detector can be efficiently obtained by a series of measurements in non-coincident (OR) mode and used for both OR and AND mode acquisition. The entire calibration procedure can be automated and performed periodically to compensate for long-term drifts.

PMT Bases: Commercially available HVPS and PMT bases are not adequate for low background detectors for biomedical applications due to dependence of HVPS and voltage divider (VD), performance/risk of high voltage cable, radioactive background of elements and electromagnetic pick-up noise between the PMT and preamplifier. Thus, an integral PMT base is preferred, containing a HVPS/VD/preamp/shaping amplifier assembly.

Conventional PMT bases use much less integrated designs. Classically, only a voltage divider is placed in the PMT base. This leads to considerable electronic pick-up noise that is undesirable in the MPD. Several commercial devices feature PMT bases with integral voltage divider and preamplifier. For maximal integration of the PMT base, it is preferred to include the HVPS, voltage divider and preamplifier because the use of high voltage cables leads to problems with ground loops and electromagnetic pickup and may pose the risk of electrocution, especially with portable devices when used in high humidity environments.

The radioactive background of PMT bases was measured by placing the PMT next to a 2" diameter, 2 mm thick $CaF_2(Eu)$ detector coupled to a selected low-background 2" PMT. The whole system was well shielded with lead, tin and copper. Then the background in the $CaF_2(Eu)$ detector was measured in the energy range of 20 to 40 keV (the region of interest for $I^{125}$), and compared with the background without the studied PMT base. Pulse-shape analysis was performed to discriminate between events and electronic artifacts. The background due to PMT bases was measured with bases 2 mm and 5 cm from the surface of the $CaF_2(Eu)$ crystal. The first positioning permits measurement of the background while the measurement at the second position indicates how much this influences the MPD performance (length of used PMT's is about 5 cm). The background in the $CaF_2(Eu)$ detector in the absence of test PMT bases was found to be 0.7 cpm.

When placed 5 cm from the scintillator, the background due to the PMT base assembly does not influence overall background of the MPD. However, it is surprisingly large when placed close to the scintillator. Thus, several PMT bases were disassembled and the radioactive background of individual components, was tested, namely:

plastic HV connector;

divider chain resistors and capacitors;

Pb/Sn/Cu composite shield;

Aluminum holder and housing of PMT base;

HVPS module and preamplifier module.

Surprisingly, it was found that the largest radioactive background is from the plastic high voltage connector, mostly due to beta particles. This background can be very efficiently attenuated by a thin plastic guard ring. After this modification, the PMT base radioactive background accounts for less than 10% of radioactive background of PMT's.

Quantitative measurement of low activity sources, say $\leq 0.1$ picoCurie, may require measurement times of up to several hours. Any slow drift of electronics can therefore influence these long term (1 hour) measurements. The main source of this drift is the PMT's. The strong dependence of the amplitude gain on the high voltage from the HVPS leads to temperature-dependent signal drifts.

High voltage power supply: The voltage divider supplies the negative voltage from the HVPS to the PMT dynods (pins 1–11) and to the cathode C via an RC circuit. This is shown in FIGS. 3A, 3B, and 3C in PMT base assembly 30. The voltage divider resistors represented as R7 and R8 have a low temperature coefficient ($\leq 100$ ppm/° C.) and thus stabilize the PMT output signal. Negative HVPS 50 preferably includes a regulated DC to DC convertor 64 from Matsusada Co., voltage regulator 66 and a feedback circuit with precision reference 68 (temperature coefficient about 3 ppm/° C.) and comparator amplifier 70. Elements with low temperature coefficient are preferred because of the importance of diminished temperature dependence of HVPS output.

Ten-fold better performance can be achieved than when using commercially available NIM modules such as are available from Ortec, Canberra or Tennelec. This diminished the diurnal variability of the MPD considerably.

A preferred HVPS has the following characteristics:

Input voltage: −15 to −18 VDC

Input current: $\leq 120$ mA

Output voltage range: 300–1,100 V [DC]

Noise: $\leq 50$ mV peak-to-peak

Temperature stability: ~20 mV/° C. at nominal output voltage (1,000. V)

Figure 3:
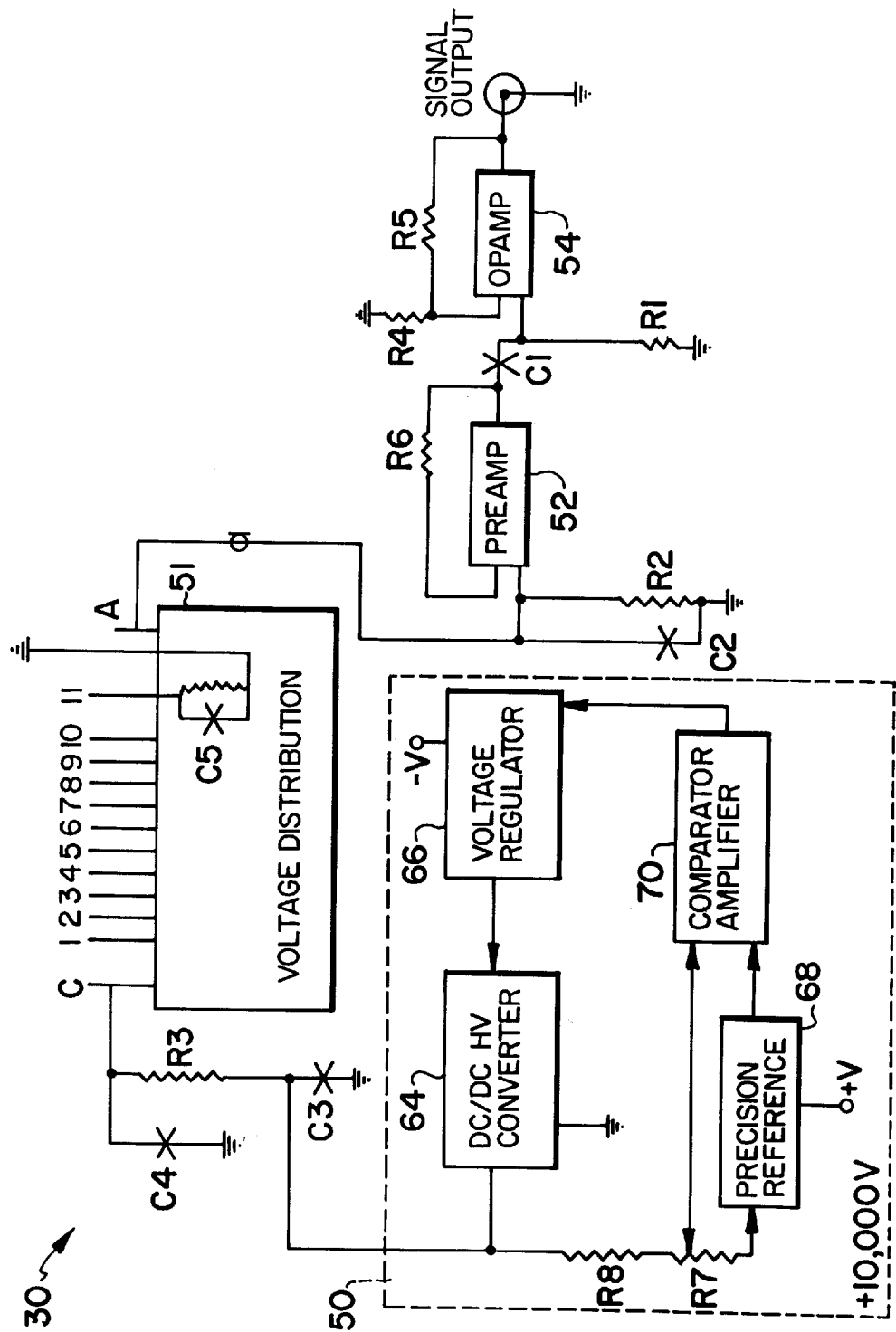
FIG. 3 is a block diagram of an integrated photomultiplier base including amplifier and high voltage power supply.
Figure 3A:
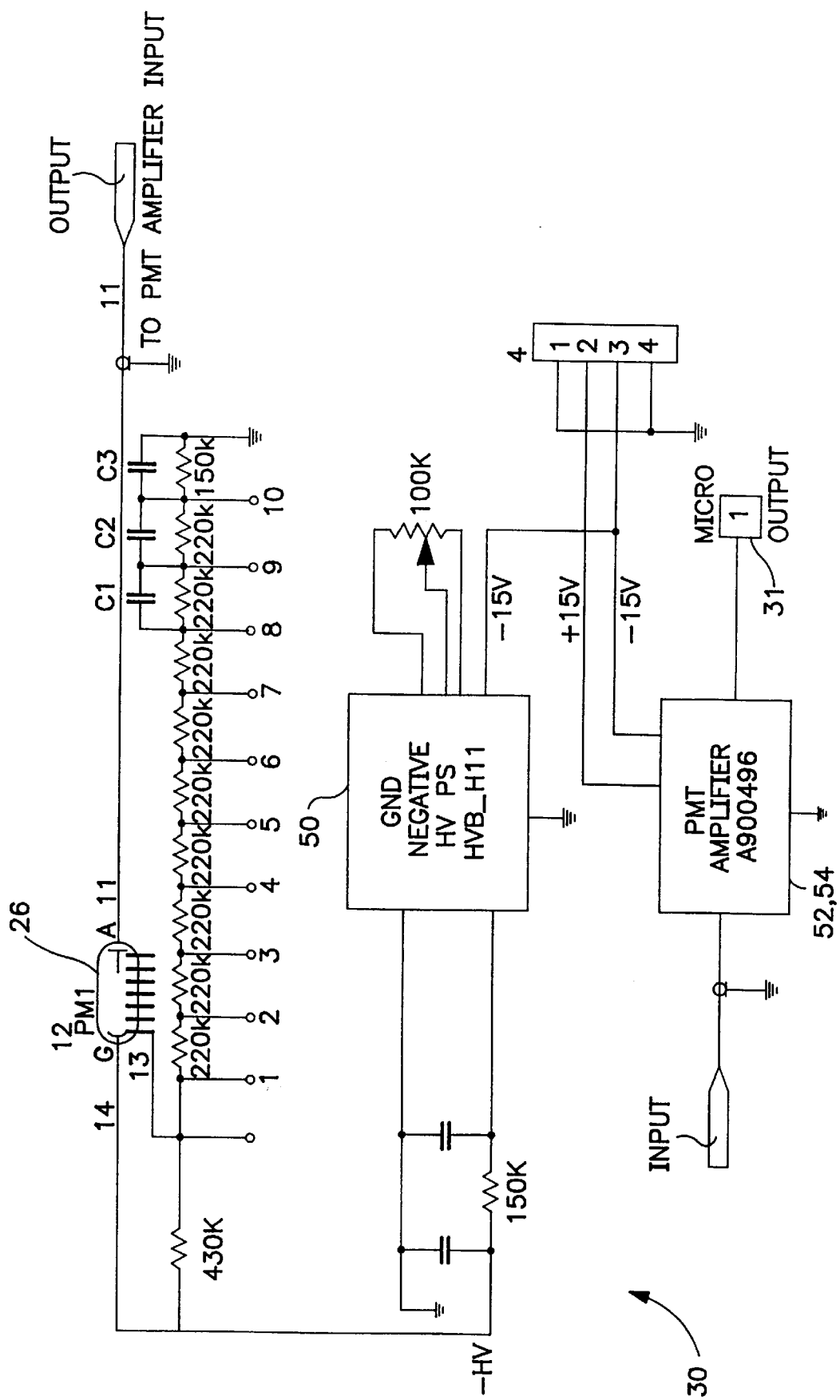
FIGS. 3A to 3C show exemplary embodiments of the component parts in more detail.
Figure 3B:
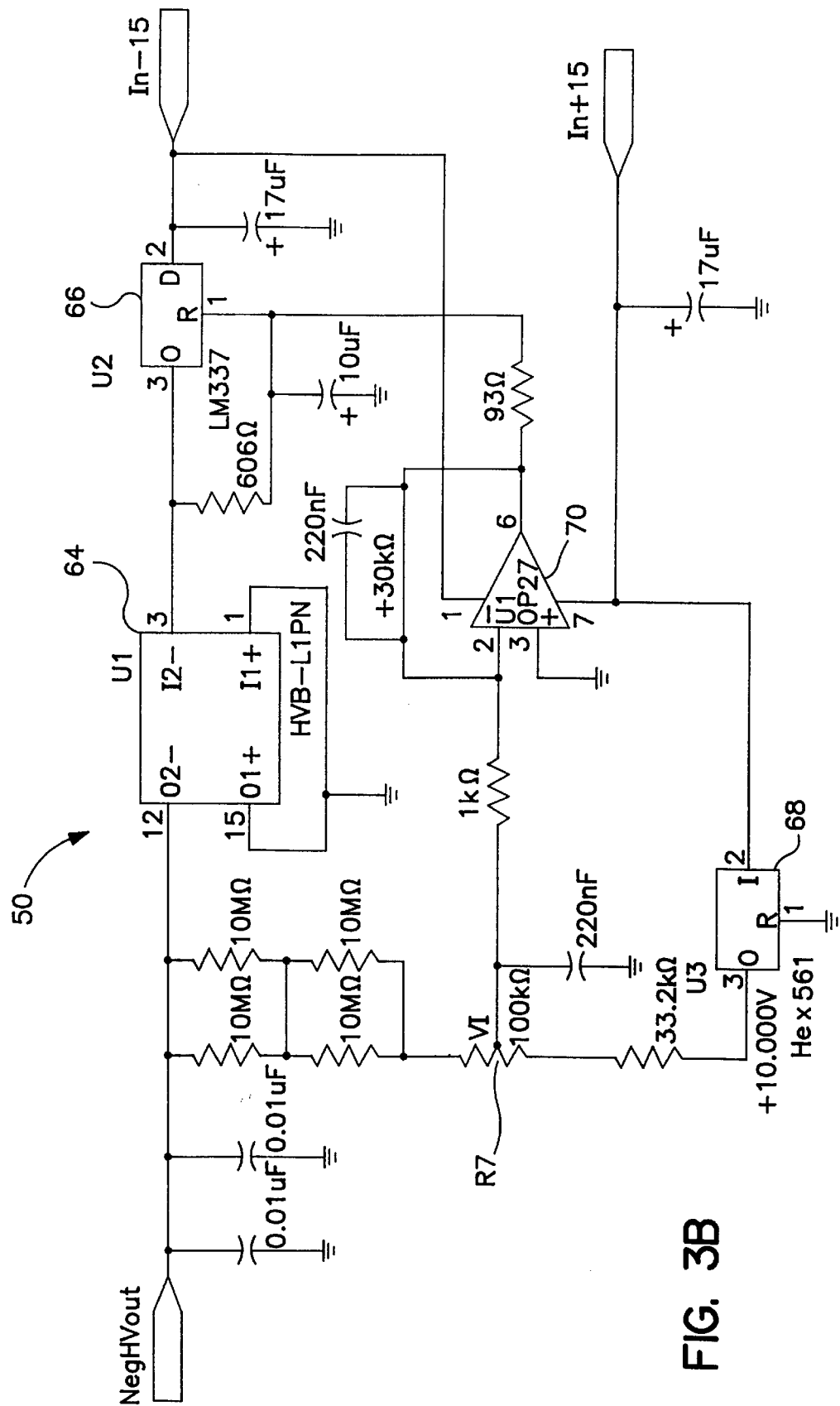
Figure 3C:
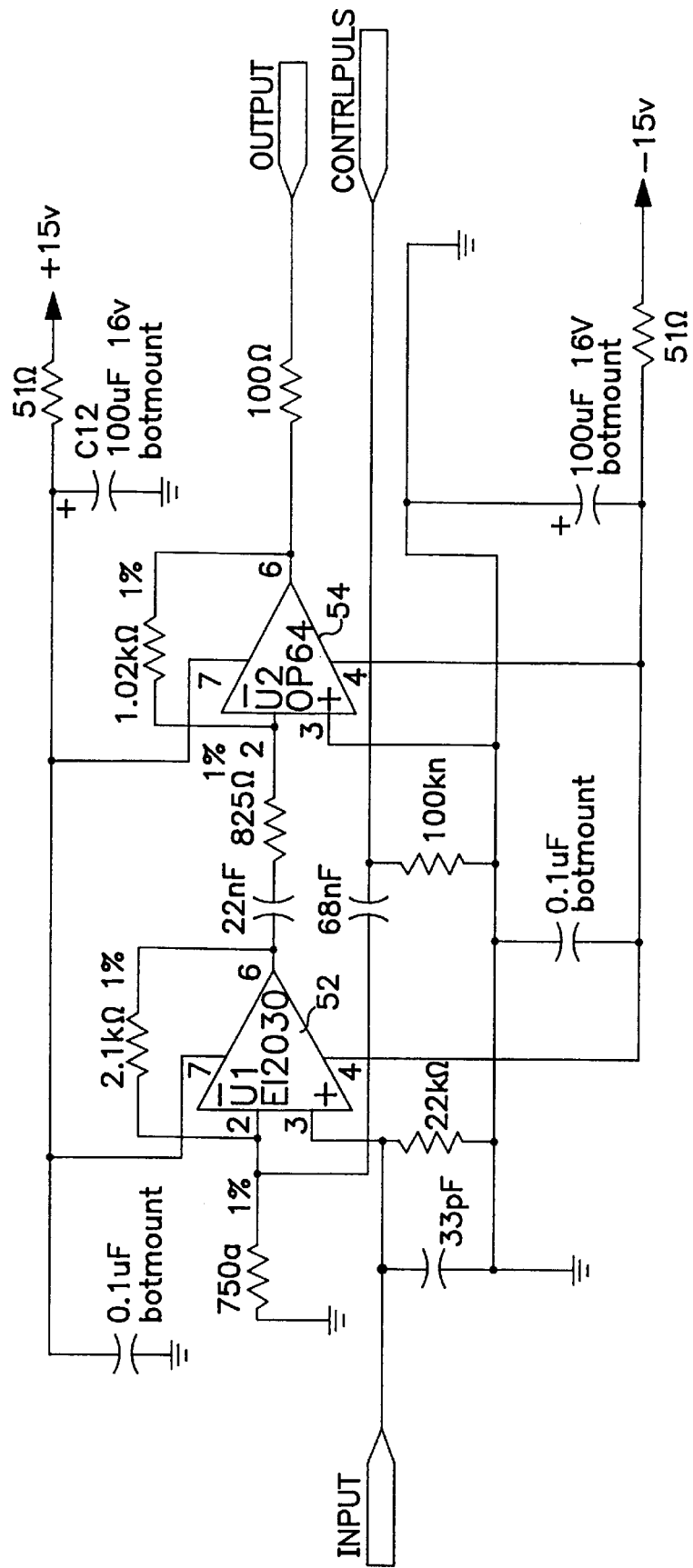

Another important element of the PMT base is optimized preamplifier/shaper 52 shown in FIGS. 3 and 3C. A triangular pulse shape is optimal when using pulse shape analysis to reject background, e.g., due to dark current pulses in PMT'S. In contrast, the majority of commercial devices use Gaussian pulse shaping, which optimizes the energy resolution for low energy X-rays and is preferred when pulse height analysis is performed, e.g., using multichannel analyzers. The amplifier/shaper preferably includes a preamplifier 52 based on an EL 2030 low-noise current feedback amplifier and an output amplifier 54 based on a model OP64 amplifier with high gain and dynamic range. Output amplifier 54 does not need correction and tuning during performance. The pulse differentiation chain C1, R1 and integration chain C2, R2, as shown in FIG. 3, define the parameters of the output pulse:

Rise time $t_r$~400 ns [800 ns]

Pulse width at 0.1 FWHM t=3 ms [4 ms].

The first numbers correspond to the use of NaI(Tl) scintillators while the numbers in parentheses correspond to $CaF_2(Eu)$ scintillators. The resistor chain R4, R5 defines amplifier 54 gain. The gain was chosen in the interval 20–50 and is adjusted by potentiometers. This value depends on the properties of the given PMT and scintillator crystal and provides an output amplitude of about 2 V for 30 keV photons.

The resulting PMT base/operational amplifier assembly according to the invention has the following properties:

Noise $\leq 50$ mV peak-to-peak

Gain 20–50

Dynamic range 50,000

Offset $\leq 2$ mV

Input signal $t_r$=200 ns, t=100 ms, [negative polarity pulses]

Output signal $t_r$=400 ns, t=3 ms, [positive polarity pulse]

Max. output signal 10 V

Nonlinearity $\leq 2\%$ over the full dynamic range

Power source DC current $\leq 20$ mA, Voltage from $\pm 12$ V DC up to $\pm 18$ V DC PMT base size 2.2" diameter, 3.75" length Weight 1 lb (this includes 0.5 lb of internal Pb/Cu shield)

These electronics have high temperature stability and do not require adjustment during operation. The device is also easy to produce and tune. When compared with NIM modules, they are 10 times more stable and considerably cheaper to produce.

Noise and temperature stability: The high sensitivity and low background requirements of the MPD drive the specifications for the electronics. Conditions which cause a decrease of spectral sensitivity and S/B ratio can be separated into short-term noise (electronic noise, dark pulses) and long-term drift of electronic parameters (gain, high voltage, temperature drift).

The energy resolution dE/E(FWHM) at 30 keV for preferred detectors according to the invention is about 16% for NaI(Tl) and about 35% for $CaF_2(Eu)$. If electronics are to contribute less than 10% degradation to the energy resolution, this leads to a noise to signal ratio (N/S) of $\leq 0.016$. The amplifier, high voltage power supply (HVPS) and electromagnetic shielding allow obtaining N/S $\leq 0.005$. The majority of electronic noise sources are filtered by the electronics, while the rest of the noise is rejected by on-line software shape analysis.

When using commercially available HVPS, the temperature dependence leads to easily measurable drifts of pulse amplitude for $I^{125}$. With preferred HVPS according to the invention, the temperature dependence of the gain upon ambient temperature is below measurable accuracy. To decrease the influence of HVPS temperature variation, the voltage divider for the PMT's can be implemented using metalloceramic 1% resistors with a low temperature coefficient. Furthermore, current feedback and the use of a super stable source of baseline voltage allow for a small size HVPS (see FIG. 3) with the following parameters:

DC voltage input: −12 to −18 V output: −300 to −1,100 V

DC current input: ≦120 mA output: ≦1 mA

Output noise ≦100 mV

Pulse noise ≦150 mV peak-to-peak with 100 kHz frequency

For example, the pulse noise is a factor of 2–3 better than for commercially available HVPS.

The temperature dependence of HVPS output voltage between 25° C. and 70° C. was compared for commercial HVPS and the HVPS according to the present invention. The baseline/noise shows a better than 1% stability of the baseline during a 24 hour period (measured in winter with heating switched off, i.e., leading to a day/night variation of about 15° C.). The performance of the negative HVPS according to the invention was compared to HVPS PS1800 series (Electron Tubes, Inc.). Both HVPS's were switched on at the same initial temperature (25° C.) and then were heated simultaneously up to 60° C. The commercial HVPS showed a few percent drift of voltage, but the output of the HVPS according to the invention demonstrated no discernable variation due to heating.

Single Sample MPD: A preferred implementation is now described. Existing gamma counter designs typically optimize detection efficiency. According to the invention, the goal is to minimize background while keeping detection efficiency reasonably high. To reach this goal it is necessary to eliminate sources of radioactive background, employ optimal counter geometry (including of shields and separator), carefully select components, use stable electronics, and use on-line software for background signal rejection.

The MPD therefore includes the following sub-systems:

photon detectors, e.g., scintillators with PMT read-out;

a separator/shield subsystem;

read-out electronics; and a data acquisition/analysis subsystem.

$CaF_2(Eu)$ scintillators are preferred for their good stopping power and reasonable energy resolution as previously described. Such systems achieve exceptional background rejection resulting in an improved capacity to quantitate minute traces of target isotope. The device can be operated in two modes as previously described. In the OR mode we achieved high DE (>50% for $I^{125}$) is achieved with a radioactive background of about 1 count per minute (1 cpm). In the coincident (AND) mode, the DE for $I^{125}$ is below 20%, but achieves an ultra-low radioactive background of 1 count per day (1 cpd). These results were achieved at the earth's surface with a relatively small shield (about 20 kg of lead). The system is designed around low cost commercially obtainable components and well established technologies.

Figure 2:
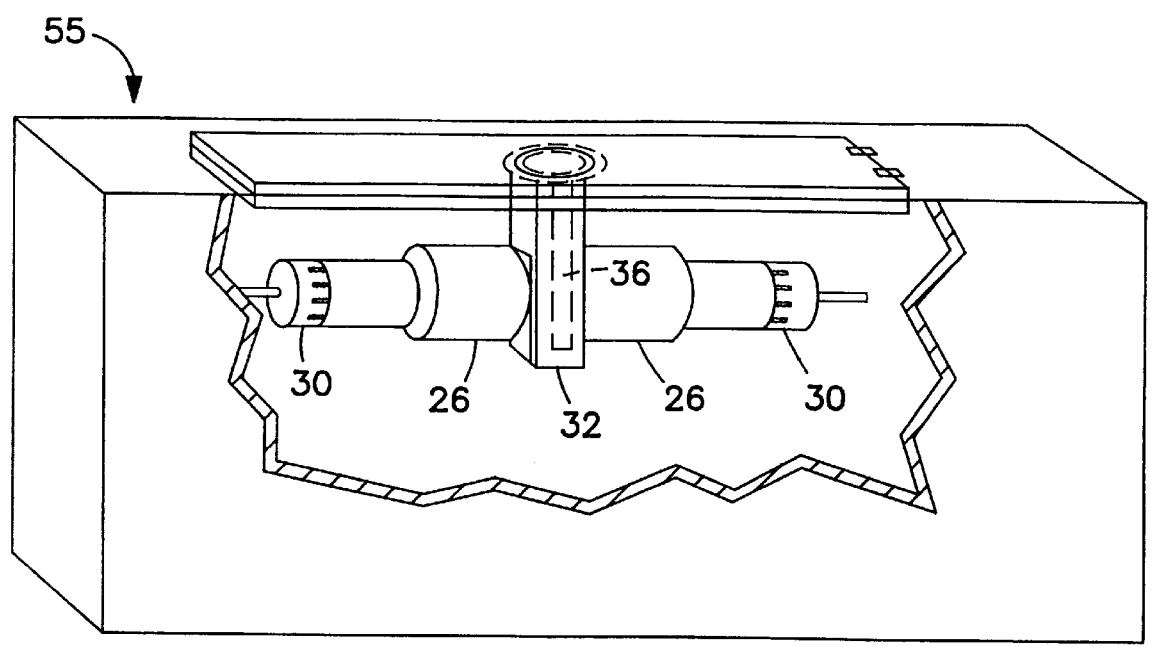
FIG. 2 shows a detector subassembly.

A preferred implementation of the MPD detector optimized for detection of $I^{125}$ is now described. A block diagram of the MPD detector is shown in FIG. 1 and an elevation is shown in FIG. 2, including "sandwich" geometry, multiphoton coincidence and pulse shape analysis subsystems. Detector 20 includes two modules separated by low radioactive background separator 32 consisting of heavy metals, typically a sandwich consisting of a few millimeters of Cu/Sn/Pb. Inside separator 32, a hole 34 is disposed into which sample 36 is to be placed.

The assembly of the two detector modules 20 is enclosed in a heavy metal composite passive shield 55, built of radioactively pure materials, typically lead, tin and copper as previously described. The highest atomic number material, e.g., lead, is most external and at least 1 inch thick. It is followed by a lower intermediary atomic number material, e.g., tin, with a few millimeters, e.g., 1–2 mm, thickness. Finally, a few mm (typically 2 mm) layer of very pure copper is used.

Each of the detector modules includes the following elements:

inorganic scintillator crystal 22, with thickness optimized for a given emitter;

high purity optical window 24, placed between scintillator and PMT;

selected, low radioactive background PMT 26;

graded passive shield 46 between the PMT 26 and PMT base assembly 30;

PMT base assembly 30 with of high voltage power supply 50, voltage divider 51 and preamplifier 52 (shown in FIG. 3).

$CaF_2(Eu)$ crystals less than 3 mm thick are preferred as scintillators. Optical window 24 is at least 4 mm thick ultrapure quartz, optically polished and provided with optical coupler 23, a low radioactive background silicon grease.

Selected PMT's 26 are made of glass with low contamination by $K^{40}$, preferably 2" PMT's preferably selected to present less than 0.1 cps background. It is preferable to decouple the PMT base 30 from the PMT 26 by means of graded shield 46 having three layers of metal with very different atomic numbers. Typically, such a graded shield includes about 0.2" of Pb, 0.15" of Sn and about 0.1" of Cu.

PMT bases 30 are preferably fabricated from selected materials with low radioactive background, e.g., using pure copper or aluminum for the supporting frame. The use of resistors and capacitors selected for low radioactive background is disclosed, as well as the use of In-free solder, e.g., made of pure Sn or Sn/Pb alloy. All passive and active elements of the PMT base 30 are selected to have a very low temperature drift, and active compensation techniques to eliminate temperature dependent gain drift are disclosed.

Both an OR and an AND mode are used for data acquisition and analysis, with a multichannel DSO 52 for on-line background rejection. Triangular shaping and software rejection of fast pulses due to signals induced by cosmic rays in the PMT's 26 is employed. A pulse rise time of about 0.75 microseconds and a slow fall time of about 5–10 microseconds are preferred.

Self-diagnostic and self-calibration is used for reliably matching the count rates in the OR and AND modes, more specifically, on-line baseline restoration and pile-up rejection techniques. In the coincident mode, it is crucial to use the DSO 58 for matching the shape and temporal coincidence of pulses from the two detector modules. There is a trade-off between the need to estimate the pulse coincidence to within better than 100 nsec and the need for a triangularly shaped, long duration pulse permitting rejection of dark currents from the PMT's. On-line software based pulse fitting procedures however overcome these conflicting requirements.

Pulse shape analysis: Data acquisition in a twin scintillator system is based on amplifying and shaping the signals from the PMT of each detector and building a combined energy spectrum for subsequent analysis. The counts in an appropriate energy region of interest (ROI) for the desired isotope are then integrated to determine the count rate. For a sandwich detector consisting of 2" diameter NaI(Tl) or CaF$_2$(Eu) scintillators, the detection efficiency is typically about 50% when only events in the single-photon energy ROI are counted. For I$^{125}$, counting both 30 and 60 keV events increases the detection efficiency to about 70%, but effectively doubles the integration energy range and therefore the background.

Conversion of the count rate (counts per minute, or cpm) into the actual activity in the sample (decays per minute, or dpm) requires knowledge of the detection efficiency (DE) of the counter. For I$^{125}$, the DE can be determined from the spectrum itself using the known Eldridge formula. The DE is determined for each detector separately, which allows improvements in the calibration and accuracy, and testing the system integrity and correcting for the sample placement by comparing the two estimates of the actual activity of the calibration sample. The spectrum of coincident events can be used to enhance DE evaluation and for diagnostic purposes.

The predominant component of the non-radioactive background in low-energy gamma/X-ray detectors is due to dark pulses in the PMT's. In the I$^{125}$ ROI, these typically produce a few cpm for a two-PMT system. However, the shape of these pulses is different than those produced by scintillation in the detectors, making pulse-shape based discrimination possible. Pulse shape(s) for each event are acquired using a PC-based dual input plug-in DSO card 58 and fast pulse shape analysis is performed. This allows rejection of PMT dark pulses as well as other electromagnetic and vibrational artifacts. After pulse-shape based rejection, the background in the system is almost flat for energies in the 15–100 keV range and is remarkably stable, independent of the activities in the vicinity of the detector.

Detectors: Flat 2" diameter detectors (1 mm thick NaI(Tl) or 1.5 mm thick CaF$_2$(Eu)) are preferred. Smaller scintillators decrease the DE of the system while for larger crystals the signal to background ratio diminishes. The scintillators are coupled through quartz windows 3–5 mm thick to 2" diameter high energy resolution PMT's which are selected for low background. The PMT signals are read out, amplified and shaped using electronics built into the PMT bases 30. To reduce the flux of background photons from the bases to the scintillators the bases are isolated from the PMT's with 5 mm of lead and 1 mm of copper plating with holes for the PMT pins.

Shields and holders: The detector assemblies are placed in graded lead+tin+copper shields (2" lead, 1 mm tin, 1 mm copper). The detectors are placed face-to-face half an inch from one another and a sample holder/crosstalk eliminator is placed between them. This is a 1 mm thick copper sheet mounted in a lead frame. Openings are left in the copper sheet for the samples. The shape of the opening is determined by the format of the samples to be used. A delrin guide with copper outer jacket ensures that all samples are centered in the detector system. When the sample format and sample holder are changed, the system can be automatically recalibrated using the Eldridge formula.

Figure 8:
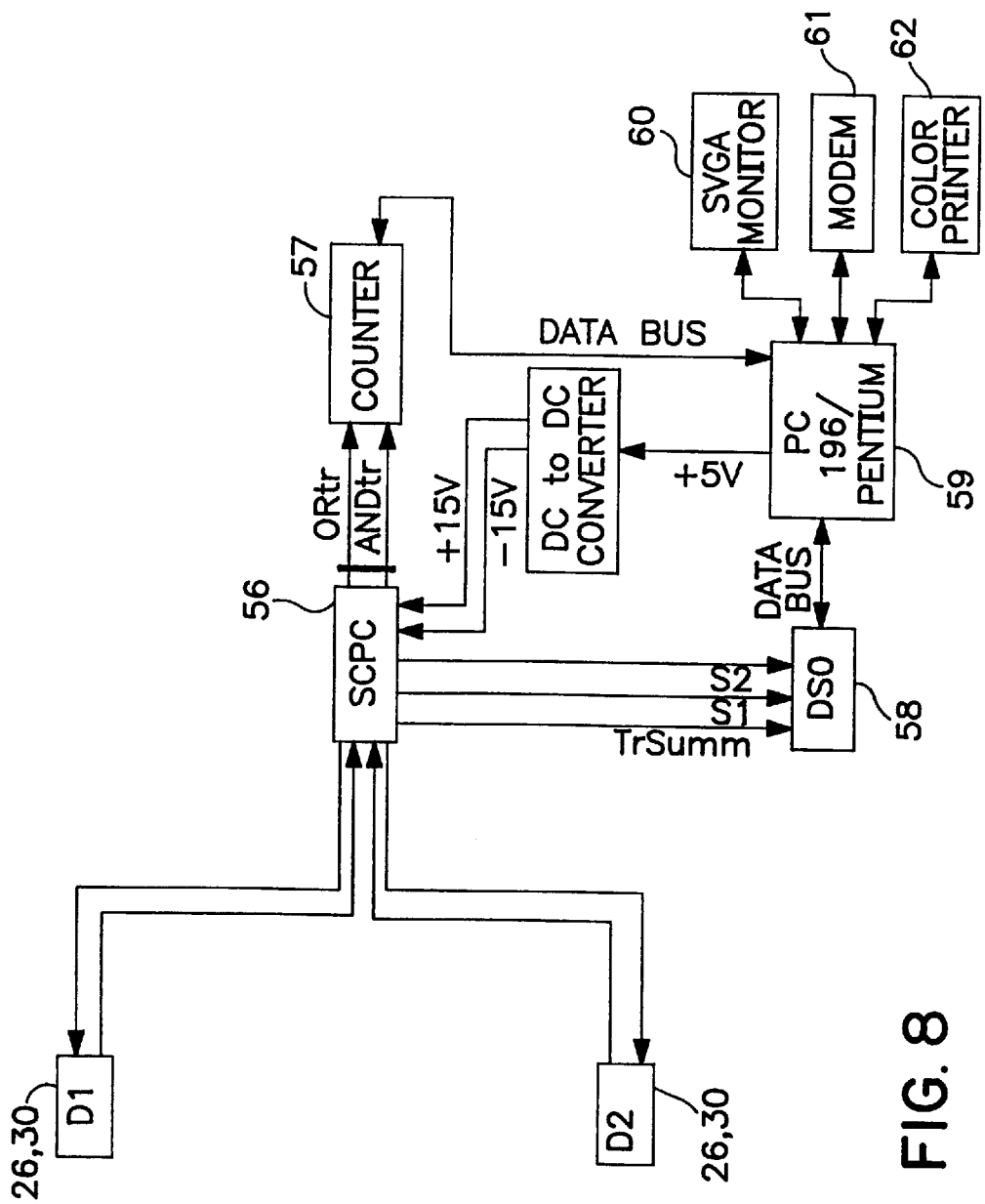
FIG. 8 is a block diagram of an MPD embodiment acording to the invention.

Data acquisition—hardware: The data acquisition hardware is preferably mounted inside the dedicated PC controlling the MPD. With reference to FIG. 8, the data acquisition electronics in an exemplary embodiment include triggering circuit 56, amplification/attenuation modules for each detector, digital timer/counters 57, and a dual channel 20 MHz digital storage oscilloscope (DSO) 58 which is used both as a 2-input multichannel analyzer and a pulse shape analyzer.

The triggering circuit 56 produces a rectangular trigger pulse whenever a pulse exceeding a preset threshold amplitude is registered in either detector 26. If pulses are registered simultaneously in both detectors a higher amplitude trigger pulse is produced. It is thus possible to count separately coincident and non-coincident events. The trigger pulse is sent to the external trigger input of the DSO. The triggering circuit may be an integral card as described below.

The amplification/attenuation modules adjust the amplitudes of the pulses so that the energy region of interest is within the 0–1 Volt window of the DSO and particles of the same energy produce pulses of the same amplitude in both channels.

The first of the timer/counters 57 is used as a precise acquisition time timer (counting the 2.5 kHz reference pulses). The second timer/counter counts all trigger pulses produced by the triggering circuit, while the third counts only triggers associated with coincident events. The data acquired from these counters are used to directly evaluate losses due to acquisition system dead time and thus enable the system to correctly count high activity sources.

The DSO 58 (preferably a commercial CSLite PC add-on card manufactured by Gage Inc.) is capable of simultaneous sampling of two input channels with 8-bit accuracy and up to 20 MHz sampling rate and has an additional external trigger input. The data are stored in on-board memory and can be transferred to the host PC RAM by standard memory-to-memory transfer via the PC bus. The dead time is strictly non-extendable and by means of the counters described above the count rates can be corrected for dead time losses. The DSO 58 is rearmed and initialized after each acquired and processed event.

The pulse traces are transferred from the DSO 58 to the host PC 59 memory and are analyzed for amplitude and shape by software.

Initially the DSO 58 is set up to continuously chart the input voltages in the two channels and wait for a triggering pulse in the trigger input. When a trigger pulse is registered, the DSO 58 is allowed to capture a predetermined number of post-trigger points and is then stopped. The relevant portion of the traces (typically 20 pre-trigger and 108 post-trigger points at 20 Mhz sampling) is transferred to the host PC 59 memory for analysis. The transfer procedure takes less than 200 microseconds per trace for a 486 DX66 computer for example.

Signal Conditioning/Processing Card (SCPC) 56: To enable the MPD detector software to process signals from two detectors, the trigger circuitry is used to:

1) generate a trigger signal whenever a pulse is produced by either PMT;

2) match the analog gains in the two channels, and 3) adjust delays between the signals and the trigger pulse.

This hardware (see FIG. 8) is preferably implemented as a signal conditioning/processing card (SCPC) 56 placed inside the computer. The SCPC card 56 features adjustable gain and trigger levels for each channel and produces a TTL trigger pulse. The SCPC card receives as inputs the signals directly from the PMT bases 30. The conditioned signals and the trigger pulse are passed directly to the inputs of the DSO card 58.

The two-channel SCPC 56 is designed for:

Production of an analog trigger which starts the DSO 58 both in coincidence mode and the mode of summation of input signals.

Production of a TTL trigger which starts the counter 57 in both modes.

Blocking the trigger if any input signal has an amplitude greater than some fixed level.

Analog delay of the input signal.
Adjustment of the DSO input signal level.
The SCPC 56 has the following parameters:
Input signal (positive pulses): 0.1–8 V amplitude; 0.1–100 ms pulse duration
Lower level adjustment: 0.2–5 V continuous.
Upper level adjustment: 0.2–5 V continuous.
Output attenuation range: −3 to −60 db.
Digital delay range: 0.1–10 ms.
Analog delay duration: (1±0.01) ms.
Output signal (positive pulses)
    analog signal: 0.1–1 V amplitude; 0.1–10 ms pulse duration
    TTL level: amplitude ≧4.5 V; duration 4–5 ms.
    analog trigger: amplitude 0.5 V for "OR" mode, 1 V for "AND" mode duration 4–5 ms.
Temperature stability
    threshold level <0.05%/° C.,
    transitioncoefficient <0.01%/° C.

Figure 9A:
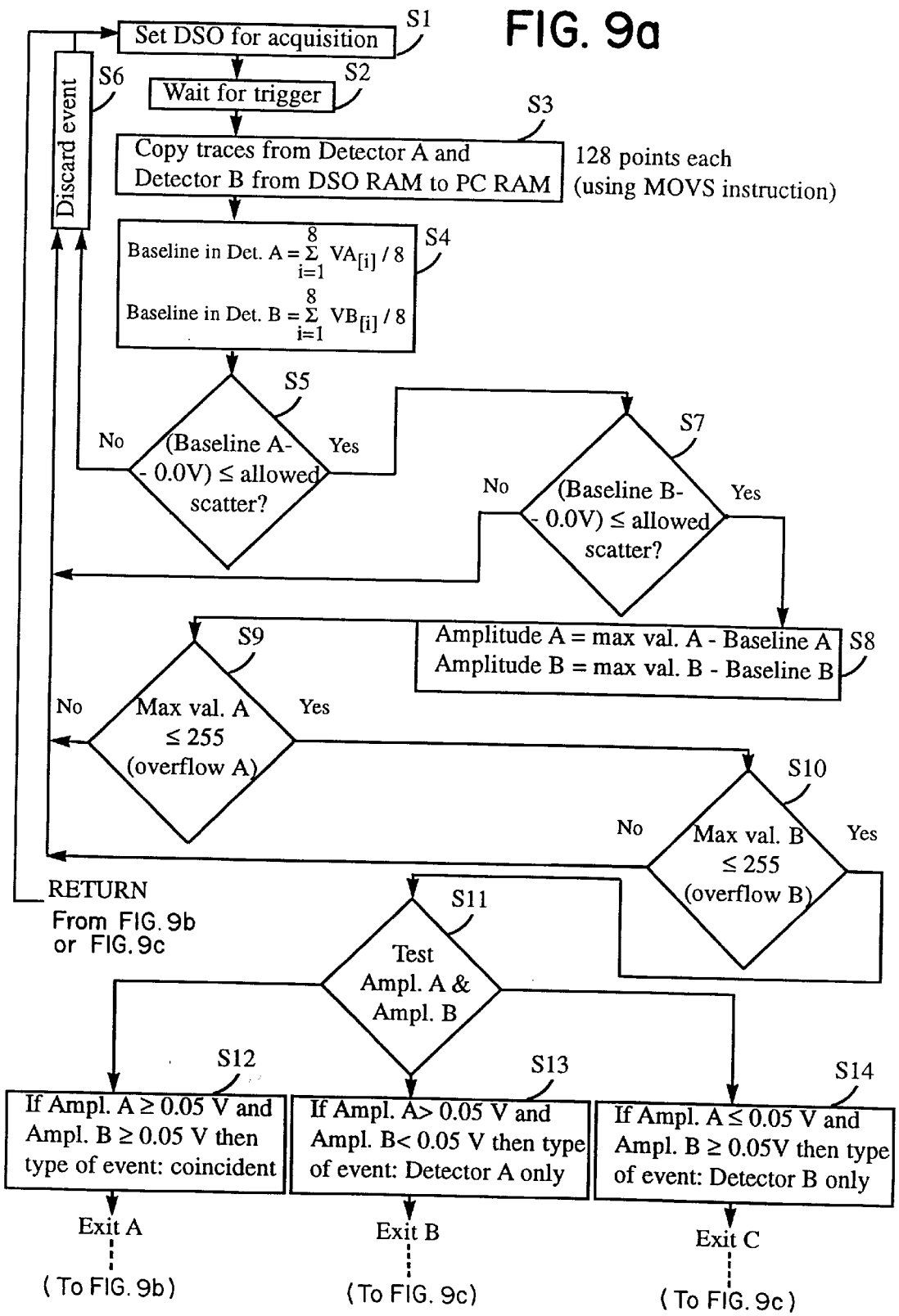
FIGS. 9a, 9b and 9c are a flow chart of a method according to an embodiment of the invention.
Figure 9B:
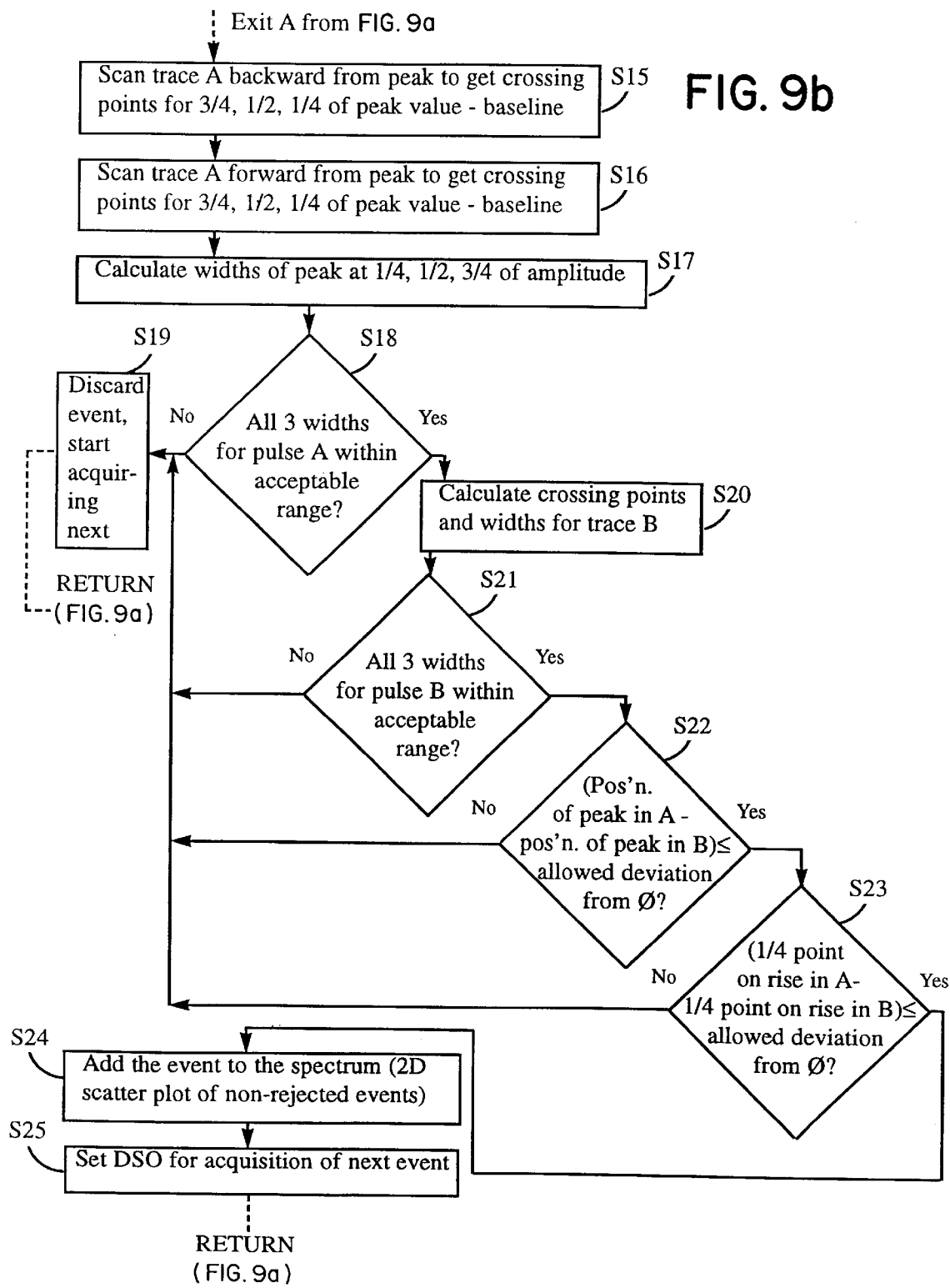

A method in accordance with the present invention will now be described with reference to the exemplary flow chart contained in FIGS. 9a to 9c. It would be apparent from the following description of this exemplary method, that the method could be implemented in a variety of processing environments with a variety of software platforms, and such are considered to be within the scope of the invention.

The on-line pulse rejection software rejects pulses whose shape is not compatible with pulses produced by particles stopped in the scintillation detector. Most of the rejected background is due to noise in the PMT, electromagnetic interference and vibrational noise.

For a given detector, the shape of the pulses caused by radioactive events does not change with time and does not depend on the amplitude of the pulse within the linear range of amplification. Thus, one approach to pulse shape rejection is to normalize the registered pulses to a common amplitude and to compare the shape of the normalized pulse to a "standard" shape using, e.g., a chi-square test. This however, involves massive floating-point computations which are much too time consuming for effective implementation on currently available low-cost microprocessors.

Alternatively, the pulse shape rejection can be performed by determining a number of parameters related to the pulse shape which can be computed using predominantly or solely interger arithmetic.

Data processing: After initial steps of setting the DSO for aquisition and waiting for a trigger, (steps S1–S2) analysis begins with computation of the baseline and the pulse amplitudes in each detector (Steps S3 to S14). From this it is known whether the event occurred in detector A, detector B or both. The pulse amplitudes are adjusted for the current baselines, and if the latter are unacceptably distorted the event is rejected. Then, a number of pulse shape parameters are evaluated and compared with the ranges of acceptable values established by the software at system set-up. These include, for example, pulse widths at ¼, ½ and ¾ of peak pulse height (FIGS. 9b and 9c). The parameters may include:
    pulse amplitude;
    rise time
    fall time
    total pulse width;
    shape of the rising part of the pulse;
    the shape of the falling part of the pulse;
    the delay between the pulses from the two detectors;
    pulse multiplicity;
    the pre-pulse trace; and
    comparator of the pulse shape with a standard high energy photon pulse shape using a least squares technique.

Fast integer-based routines for these computations run very efficiently on Intel processors. For coincident events (FIG. 9b), an additional rise-time alignment check is performed. After pulse-shape, pulse-height and coincidence/anticoincidence analysis, an unrejected event is added to the appropriate spectrum (spectrum of detector A, spectrum of detector B, or 2D spectrum of coincident events).

The DSO 58 acquires 128 points with 8-bit resolution for each input channel for each pulse. The time window spans the whole width of the shaped pulse (5 microseconds) and approximately 1 microsecond before the rise of the pulse. Digital processing of the pulse begins with calculating the average of the first 8 points S4, which gives the current baseline. If the computed baseline differs significantly from 0, the event is rejected (steps S5 to S7) as distorted by pile-up. Next 120 points of the trace are scanned (using the fast LODS instruction of the 80×86 processors) for the maximum value. If overflow is detected, the event is rejected (steps S5 to S7). Otherwise, the amplitude is computed as the difference between the peak value and the current baseline (steps S8 to S10). The program also stores the time offset of the peak. A fast (LODS-based) scan is then done forward and backwards from the peak to determine the time offsets of the crossing-points for the levels, for example, of ¼, ½ and ¾ of the amplitude (steps S15 to S20, and S26 to S28). These data are sufficient for performing pulse shape rejection tests.

Figure 9C:
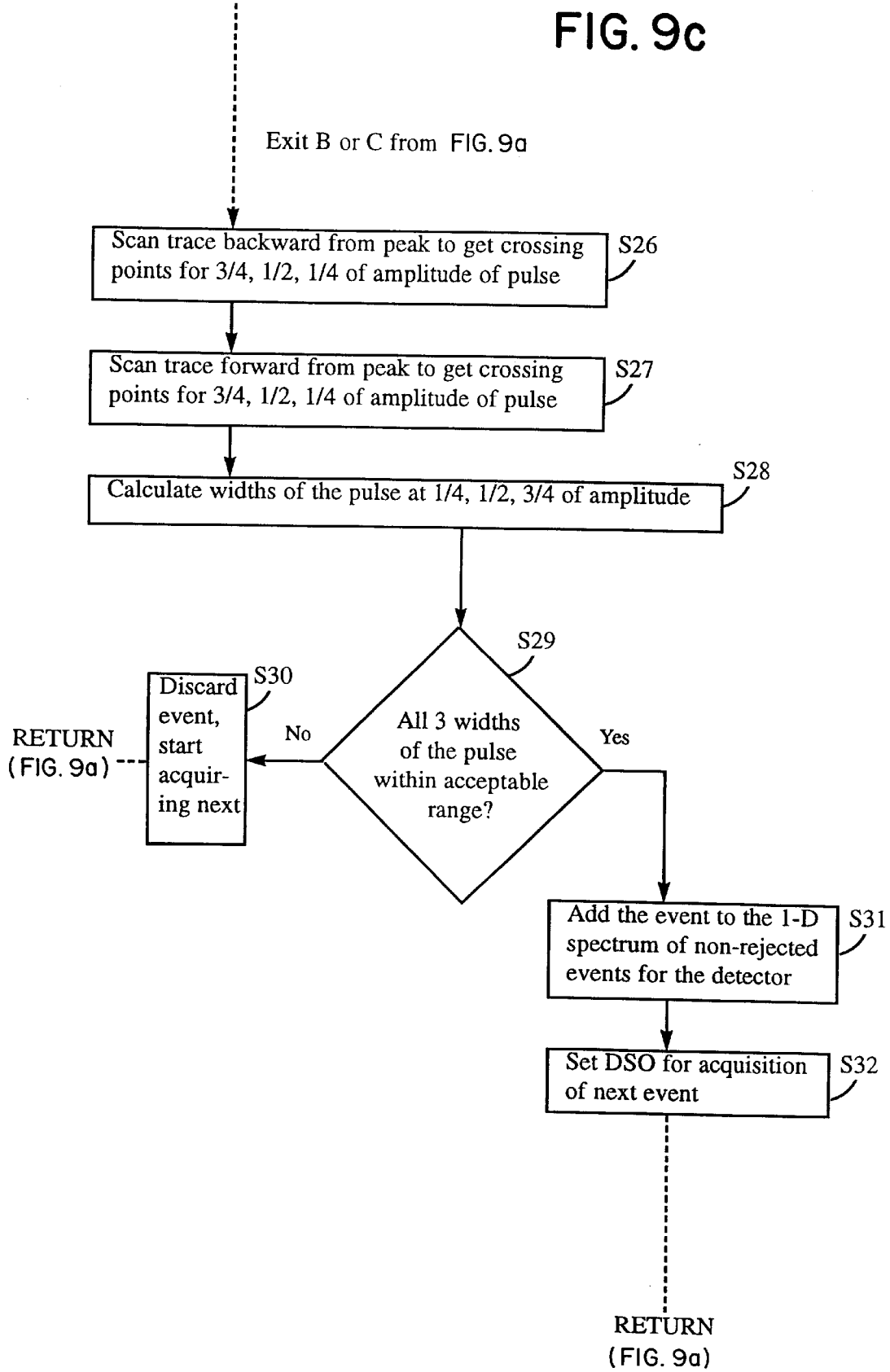

FIG. 9c details the steps of pulse shape analysis for non-coincident OR events detected in either detector A or B. Traces from detector A or B (Step S3) are scanned forward and backwards from the peak to determine the widths of the pulses for example, at ¼, ½ and ¾ of the amplitude (steps S26 to S28). If the widths are within acceptable ranges, the event is added to the spectrum of non-rejected events, and the DSO is reset (S29–S31). Otherwise the event is discarded (S30).

After an event has been processed, the DSO 58 is reset for acquisition of the next event. Any events occurring during the processing time are lost (dead time). When the spectral data are processed the computed count rates are adjusted for these losses.

The acquisition can be preset to collect data either for a given interval of time or until a certain number of counts within a selected ROI have been acquired. The acquisition can also be terminated by the user at any time.

Calibration routine: The automatic device calibration/ROI setting routine is as follows. The user can request the software to perform this procedure at any time. No calibrated sample is needed, but a reasonably high activity (optimally 50,000 to 200,000 dpm) $I^{125}$ sample is required. After placing such a source into the detector the program acquires 100,000 events with all pulse-height and pulse-shape rejections enabled. Once the acquisition is finished the spectrum is analyzed to determine the region of interest (ROI) for a single photon (27–35 keV) peak. The count rate (cpm) within this ROI is determined. If the actual activity (dpm) in the sample is known, the detection efficiency could be established from the ratio of cpm/dpm. To estimate the absolute activity of the calibration sample, the program now starts a second round of data acquisition with pulse-shape rejection disabled (as the calibration sample activity is high, there is no need to reject the background, and no real events are discarded). Spectra for both detectors (A and B) are built until 200,000 events are acquired.

Subsequently the spectrum of each detector is analyzed to estimate the count rates in the 1-photon and 2-photon peaks (the coincident spectrum is also used to enhance separation of these peaks). Then the Eldridge formula is used to estimate the detection efficiencies of the detectors and the decay rate for the calibration sample. The data are checked for consistency by comparing the estimates from detector A and detector B, and the average of the two is accepted as the absolute activity, from which the detection efficiency is estimated. The DE is normally in the range of 50–60% for 2" systems. Only the 1-photon peak is used for counting, which in the case of a sandwich detector with electronic noise rejection decreases the detection efficiency only by about 15% while diminishing the background about 2 to 3-fold.

After the autocalibration/ROI setting is complete, the system is ready to count samples of the same geometry as the last calibration sample used. Acquisition is performed either for a preset time or until a preset number of counts (determining the statistical uncertainty of counting) have been acquired in the ROI. The program then estimates the actual decay rate in the sample using the previously computed DE. The sample counting data are then typically stored to disk in an ASCII data file which can be transferred to a database or spreadsheet program for analysis.

The software sets the acquisition/rejection parameters for each newly assembled detector system. This determines the optimal trigger levels and pulse shape rejection parameters for the system and creates internal data files to store these parameters. These parameters generally do not have to be redetermined during the lifetime of the system unless a major component (e.g., a PMT/base or DSO card) is replaced.

Data presentation: The system program can be pre-set by the user to count more than one sample or to count the same sample repeatedly a requested number of times. If a batch of samples is counted, the program prompts the user to change the sample after each measurement, and all data are stored in the same ASCII file. The file contains a header with a date/time stamp and system settings, as well as an extended description of the sample(s) entered by the user using a GUI edit window before the counting begins, for example.

The program may also be provided with a simple data file browser which allows viewing and analysis of data from single samples and batches of samples. The user can select a data file to be viewed through a system of menus, see the counting uncertainty for each sample, plot the count and decay rates vs. sample number and print out the data with statistical uncertainties. A more extensive analysis and merging of data can be performed using a commercial spreadsheet program, for example.

The software is preferably coded in Borland Pascal and Assembly language to speed up the pulse processing and operates under DOS using a Windows-like GUI shell. Alternatively, software under MS-Windows can use the recently released Delphi software development system (Borland International), which uses the extended Borland Pascal language. Those skilled in the art could use other programing languages and stay within the spirit of the invention.

Self-calibration and self-diagnostics: MPD devices according to the invention include self-diagnostics and self-calibration using the redundancy in spectral information characteristic for EC sources, i.e., the one- and two-photon peaks in single-detector spectra and the 2D spectrum of coincident events (the scatter plot of energy in detector A vs. energy in detector B). Additional benefits stem from the MPD using two separate pulse counting subsystems, namely the DSO 58 and the pulse counters 57, which allows monitoring of discrepancies in the count rates between the two detector subsystems and to detect possible hardware failures. The MPD software uses data acquired from a source of known isotope to check the operation of the detectors, PMT's, HVPS and the readout electronics. Possible contamination of the MPD is detected by measuring and analyzing background spectra. The software automatically computes the detection efficiency in both the coincident and non-coincident modes for a given EC isotope using a calibration sample of that isotope. Diagnostic routines track any drift in the gains and thresholds in the device and calculate any required adjustments.

After tuning, the MPD has excellent long term stability; short time (less than 1 week) drifts are less than 1% in the $I^{125}$ peak. 1,200 independent measurements performed with MPD show reproducability is much better than the statistical uncertainty of these measurements. MPD devices permit better than 1% measurement precision for sources in the 0.1–1,000 picoCurie range. Over six months of operation the drifts were smaller than 3%.

For measurements at the zeptomole level the MPD device often runs overnight, so that diurnal variability is important. A 5° C. temperature change leads to a noticeable, about 1–2% drift in scintillator/PMT assembly performance. To compensate for this effect the temperature of the crystal can be measured and used by the software to correct pulse amplitude.

Asymmetric detector geometry will now be discussed. Examples are shown in FIGS. 10 to 14. The single sample preferred implementation discloses a fully symmetric sandwich configuration of the MPD. This geometry is appropriate for the symmetry of decay of CGX isotopes; there is no correlation in the emission direction between the coincident photons. For $I^{125}$ the two photons are nearly the same energy, which allows optimal performance using symmetric detectors. The use of any other geometry for symmetric decay is therefore inefficient. There are, however, applications which justify the use of asymmetric configurations of the geometry for best performance. The various types of assymetry which can be used according to this aspect of the invention advantageously include but may not be limited to the following:

the two detectors are made from different materials, e.g., two different types of scintillator can be used, or one scintillator and one semiconducting detector may be used;

the two detectors are of different size, typically one very small to diminish background and one large to increase the detection efficiency;

the two detectors serve different functions, e.g., one is spatially resolving and other is a non spatially resolving detector which serves as a triggering device.

Typically, the spatially resolved detector is partially obscured by an appropriate pattern of coded apertures while the second detector is fully exposed to the source.

Optimal configurations use a combination of elements. In one implementation according to the invention one detector includes a NaI(Tl) crystal coupled to spatially resolving PMT. However, the triggering detector is a $CaF_2(Eu)$ scintillator coupled to a different type of PMT from another producer.

Figure 10:
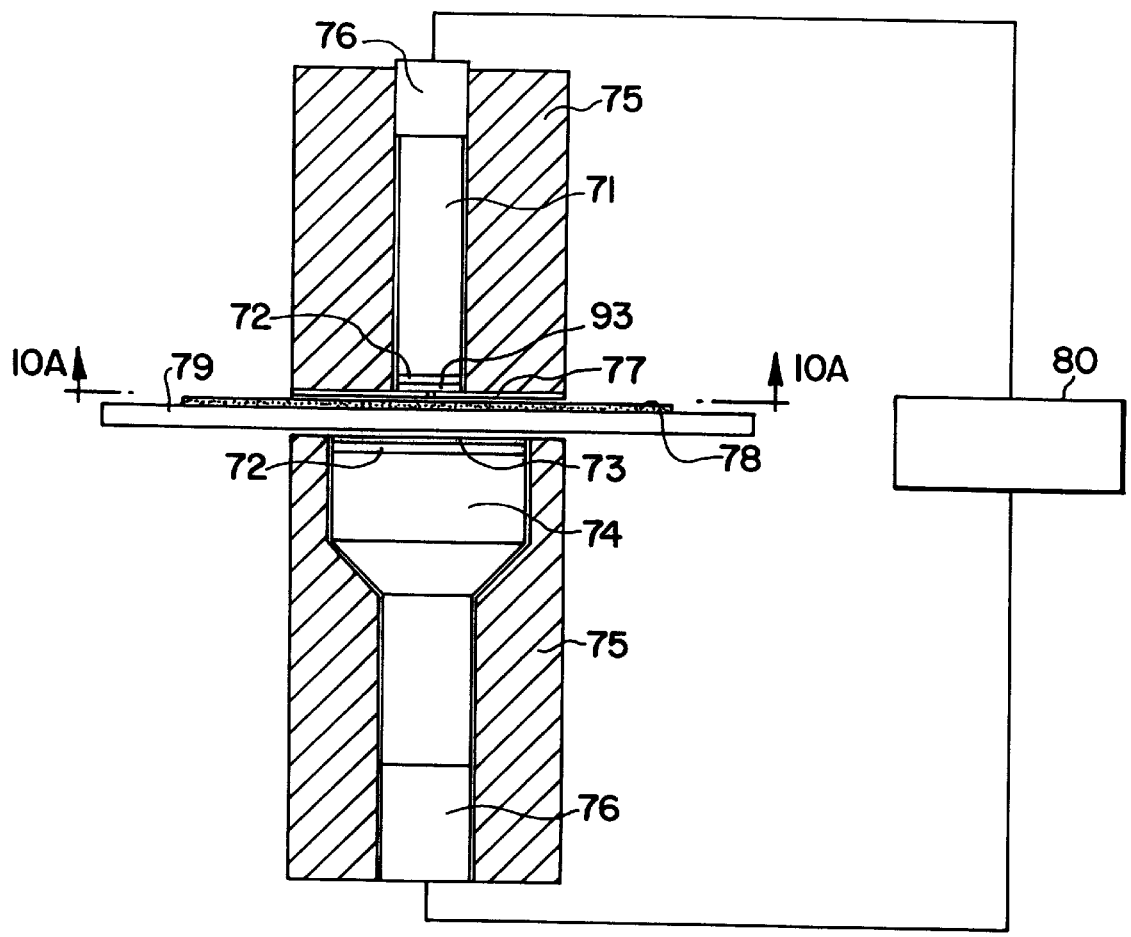
FIG. 10 shows a scanning apparatus.
Figure 11:
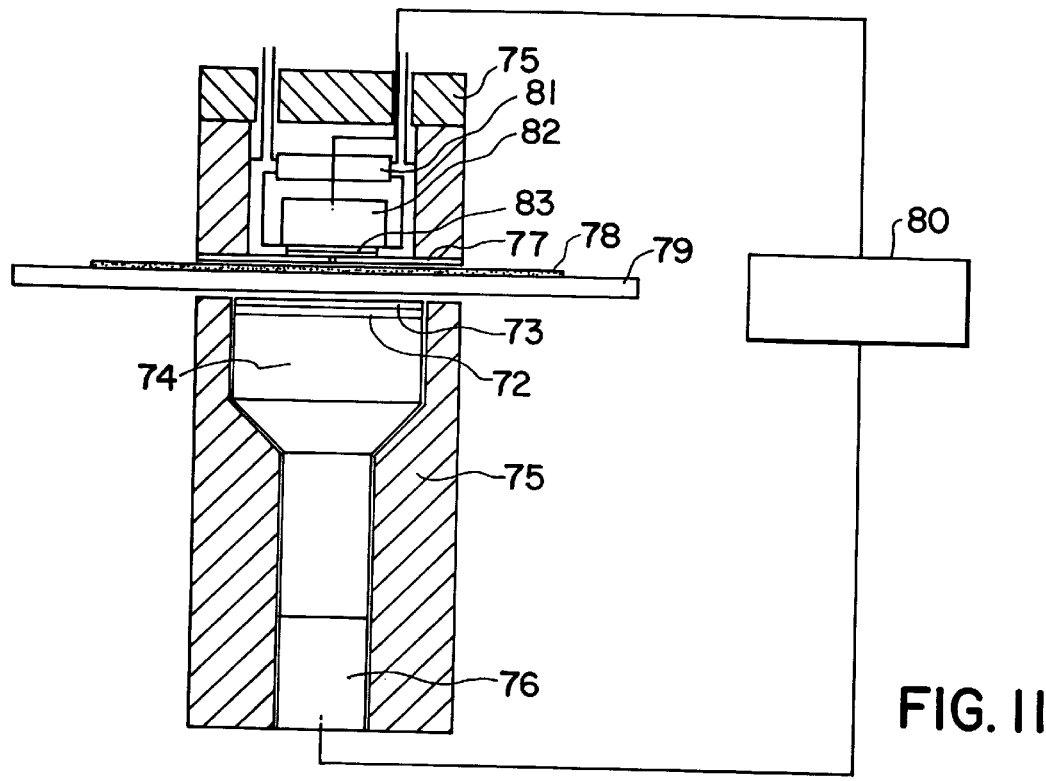
FIG. 11 shows an apparatus using a semiconductor detector.

FIG. 11 illustrates an asymmetric configuration in which the upper detector is a Ge-semiconductor detector 82 placed inside a cryostat 81 having beryllium or aluminum windows 83. In the embodiment shown, the sample holder and lower detector are as with FIG. 10, discussed below.

For a spatially resolving MPD detector (herein referred to as SR-MPD), the system performance depends on optimizing all parts of the system, e.g., the type of scintillator, scintillator diameter, scintillator thickness, thickness of the optical window, and the type and geometry of the coded aperture mask.

A high resolution, spatially resolving MPD is now described. The single sample MPD permits considerable background reduction when using a single sample labeled with CGX isotopes, especially $I^{125}$. However, for many applications, one needs good spatial resolution, e.g., when measuring radiolabeled distributions obtained in separation processes (electrophoretic gels, dot blots, thin layer and paper chromatography), and in anatomic studies of tissue preparates.

Very popular 2D radiolabeled distributions include products of separation by electrophoresis, thin layer chromatography (TLC) or high performance liquid chromatography (HPLC) which can be subsequently filtered upon an appropriate medium. These may be referred to as chromatograms. They are usually self-supporting, i.e., the separation product is deposited or trapped upon the surface of a thin, mechanically stiff plate. The most popular class of 2D radiolabeled distributions are electrophoretic separation products trapped inside gels. Typically, the gels can be cured or dried to improve their mechanical properties. In this and many other many cases, however, it is more practical to sandwich the biomedical sample between two thin films of material. Finally, electrophoretic separation products are often transferred or blotted upon elastic membranes, either nitrocellulose or plastic. These products are called blots.

For all these applications, MPD detectors can be implemented to replace classical autoradiography and phosphor imagers. In all these applications the biomedical sample is essentially a 2D object, thickness being much smaller than the two other dimensions. Often, it is supported on one side by an appropriate thin membrane. In the majority of applications, the thin support may be produced from a material with low atomic number, e. g., plastic. Such a thin mechanical support can be implemented so that it has relatively small absorption of X-rays, say less than 5%.

Figure 13A:
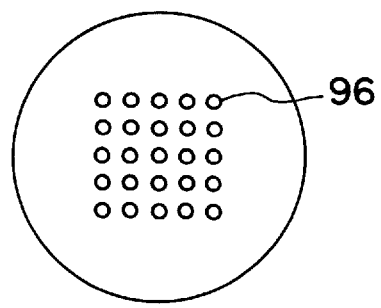
FIG. 13A shows a mask with aperture pattern.
Figure 13:
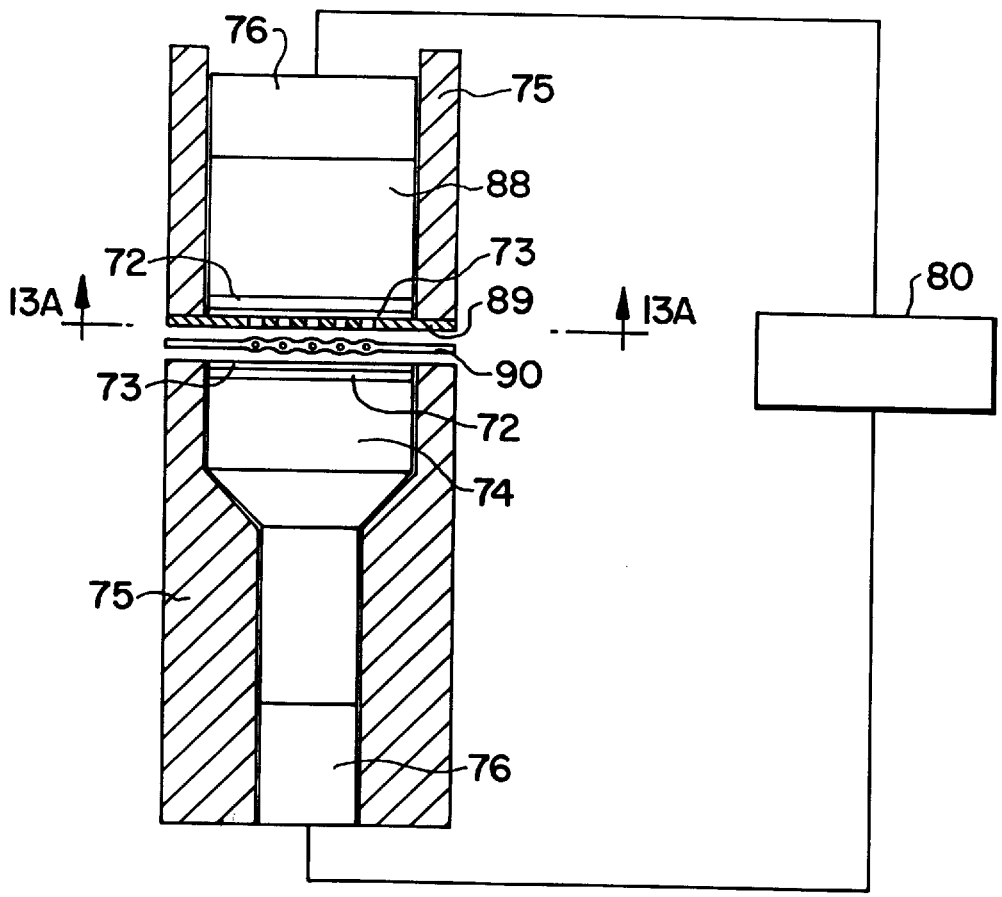
FIG. 13 shows a sample holder comprising an encapsulated spot.
Figure 14A:
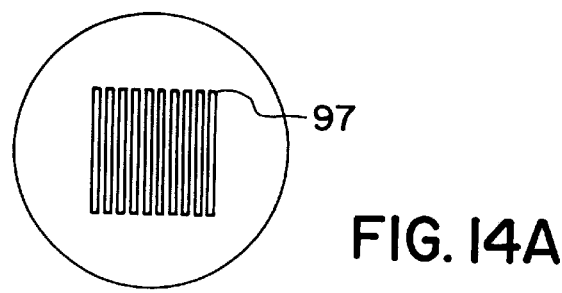
FIG. 14A shows a mask with multiaperture slit pattern.
Figure 14:
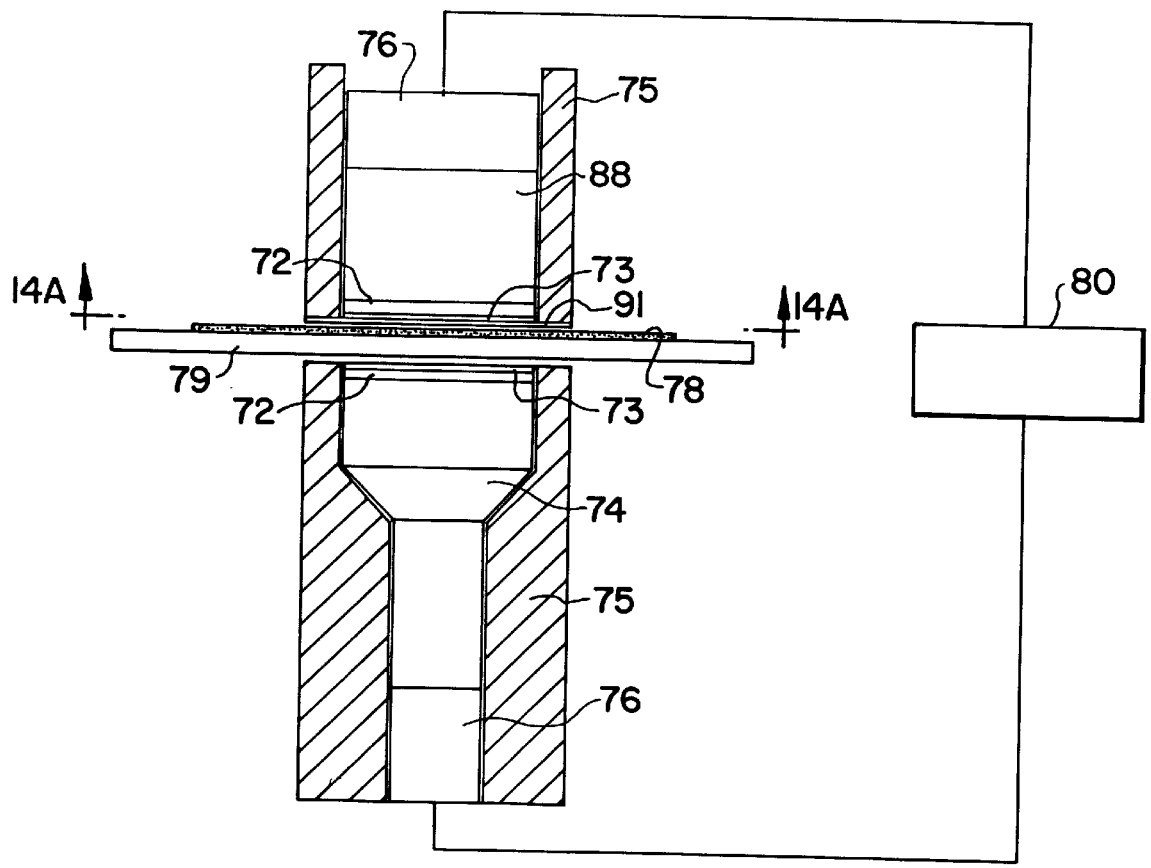
FIG. 14 shows a spatially resolving imaging apparatus.

FIGS. 13 and 13A, and FIG. 14, illustrate spatially resolving imaging devices. In particular, FIGS. 13 and 13A show casette 90 with laminated samples interposed between film 89 with coded hole pattern 96, scintillator 73, quartz window 72, and spatially resolving photomultiplier 88.

Three competing requirements on the physical presentation of radiolabeled 2D distributions are:

1) samples should be flat and easy to handle mechanically;
2) samples should be hermetically sealed to eliminate detector contamination by direct contact or by degassing of aerosols;
3) the X-ray absorption in the confining material should be minimized. These three requirements are due to the unprecedented technical performance, especially sensitivity, of SR-MPD detectors. First, the sample should be as flat as possible, because a change of distance from the sample to the detector surface leads to artifacts in the measured activity. Conventional detectors are typically calibrated to within ±5% whereas the MPD achieves ±1% calibration and reproducibility. Also, when samples are not flat there is considerable loss of spatial resolution. The unprecedented sensitivity of the MPD means that even the smallest contamination is fatal for measurement integrity. Often, not only the biomaterial but also the supporting material is contaminated. This is the case for blots because the blotting is performed using a special buffer liquid, and a small fraction of radiolabeled electrophoretic product is transported by diffusion to the reverse side of the membrane. Similarly, the reverse side of TLC plates is often slightly contaminated. Finally, when operating with sub-picoCurie samples, any additional absorption is a problem. Confinement methods using very thin layers of low atomic number materials are therefore preferred.

Three preferred methods of encapsulating 2D radiolabeled blots are as follows. For self-supporting samples, e.g., chromatographic plates or blots, the easiest and most practical method is to spray them with a liquid lacquer. Acrylic sprays, silicon sprays and electrical varnish have been used successfully. It is important to check the spray material for radioactive contamination; and to use only sprays which have coincident activity lower than 0.1 picoCurie/cm$^3$. Another practical method is to use thin adhesive tape made of either plastic or very thin (<0.1 mm) aluminum tape. Thin pouches may be used, preferably pouches made of thin films of beryllium. However, for most applications pouches or bags made of plastic or very thin aluminum are adequate. For non self-supporting samples, lamination is a very practical method of providing them mechanical properties and radiochemical purity required by the SR-MPD instrumentation. As lamination is typically achieved by rolling the foil-sample-foil-sandwich between two hot surfaces, care should be taken that the lamination machine itself is not contaminated. Also, care should be taken that the lamination foils are not contaminated.

A scanning MPD device is now described. In most symmetric MPD systems, spatial resolution is comparable to the crystal diameter. For low energy X-ray emitters, e.g., $I^{125}$, the spatial resolution can be drastically improved by inclusion of a "pin hole" or "slit" aperture. Then, 2D isotopic distributions can be mechanically displaced between two detectors, one of which has the above said aperture. This implementation is referred to as the MPD-Scanner.

Figure 10A:
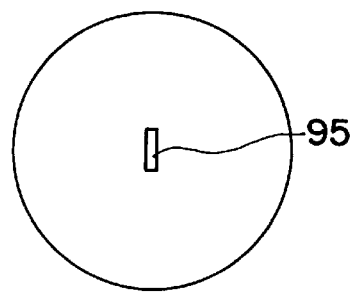
FIG. 10A shows a heavy metal mask with slit.

A scanning apparatus is shown in FIGS. 10 and 10A. The upper detector is substantially smaller than the lower one and is shown as including smaller scintillator crystal 73, quartz window 72, PMT 71, and base electronics 76 surrounded by lead shield 75. The lower detector consists of a larger scintillator crystal 93, quartz window 72, PMT 71, and base electronics 76, surrounded by lead shield 75. A thin film 77 of high density/high atomic number heavy metal having a small aperture 95 is placed in front of the small detector. The scanning apparatus may be run with the pulse shape analyzer in readout electronics unit 80 having two modes, an OR mode accepting both non-coincident and coincident pulses for counting, and an AND mode accepting only coincident pulses for counting. Sample mover 79, a moving table adapted for holding and moving the sample holder with sample 78 in two dimensions (left to right in FIG. 10, and in and out of the figure plane) has spatial resolution adequate to present essentially flat samples to the aperture in front of the small scintillation crystal; and is operated by a controller (not shown) that identifies the position of the sample mover and permits correlation with the count rate for each position; and optimizes the time of data acquisition for each sample position such that data acquisition can be stopped when the accumulated data reaches a predetermined signal to background ratio or signal to statistical uncertainty ratio; and the pulse shape analyzer and controller present the acquired data as a two dimensional image.

It is difficult to obtain sub-millimeter resolution without losing the sensitivity required for interpreting 2D radiolabeled biomolecula distribution, e.g., DNA distributions at sub-attomole levels. In conventional imagers for these applications, the principle of proximity imaging is implemented. For example, in spatially resolving detectors, for beta emitters "system resolution" depends upon the energy of the used emitter; it is considerably worse for higher energy sources due to an increase in the range of the beta particles. For example, $S^{35}$-labeled DNA bands are sharper than $P^{32}$-labeled DNA bands when imaged with film or a phosphor imager, even though they are interrogating the same DNA band. Thus the "system resolution" of static systems depends not only on the intrinsic resolution, but is considerably broadened by the emission penumbra.

The MPD-Scanner according to the present invention permits dynamic data acquisition with excellent S/B. It allows the system resolution to be directly proportional to the precision of the aperture movement upon the surface of the blot or other 2D sample format. Typically the collimator (slit) width is of the same order of magnitude as the characteristic physical band width of the sample. A stationary collimator measures the total signal coming into the entire slit area, e.g., the signal from 4 $mm^2$ of the sample for a 1 mm×4 mm slit. The situation is different when time resolving detectors are used. As the collimator moves to a new position across the blot, one measures a relative increase or decrease of activity in the area of the blot that is opened to detector by the movement of the leading edge of the slit. On the other hand, some part of the blot is no longer exposed because it is now covered by the trailing edge of the slit. Thus, knowledge of the time of signal arrival permits differential deconvolution of the blot activity and sub-millimetric spatial resolution when imaging the blots. The "system" spatial resolution is directly proportional to the accuracy of the movement of the scanner; the MPD-Scanner can provide about 100-micron accuracy.

When using a moving slit with width x, the spatial resolution dx is of the order of (x/A) where A=min{S/B; sqrt(N)}, where S/B is the signal to background ratio and Sqrt(N) is the statistical uncertainty of the measurement when N photons are detected for a given slit position. Typically, S/B>>sqrt(N)>>10 and dx is approximately 0.1 mm. For 30 keV photons, typical for $I^{125}$, about 200 micrometers thick tungsten foil stops over 90% of the photons. Thus the "edge effect" will limit resolution to about 100 micrometers. This limit can be as low as 20 micrometers for lower energy EC isotopes. There is an analogy between the improved resolution of the MPD-Scanner and the confocal microscope; the spatial resolution is better than but proportional to the aperture dimension.

There is an apparent limitation to such a system; the count-rate is drastically reduced. The optimum dimensions and material of the aperture are dependent on the application and the activity of the 2D distribution. Preferred are lead films with thickness from 0.2 to 1 mm. Typically, for scanning TLC plates and agarose gels, an aperture in the form of a slit with an opening width of 2 mm and length of 2 cm is preferred. For higher resolution acrylamide gels and sequencing blots in general, one can use slits with 1 mm width and a few mm length.

Using the MPD-Scanner, the spatial resolution is much better than the aperture dimensions; typically 0.2 mm resolution. However, this case involves reconstruction software in which for each step of the mechanical mover, the optimal count-rate is calculated. This optimal count rate depends on the signal-background ratio at the given place of the 2D distribution.

Thus, the preferred scan routine is iterative. First, a low precision, constant step statistically limited map of the 2D isotopic distribution is obtained. Afterwards, an optimized scan is performed in which the acquisition time at each spot is calculated to optimize the total scan time under the constraint of minimal spatial resolution and statistical uncertainty. The operator may choose some part of the 2D sample to be scanned with higher precision.

The counting rate in the MPD-Scanner depends on the dimensions of the crystal. An optimal configuration is one in which two crystals have different diameter. The detector on which the aperture is placed is smaller, typically 0.75 or 1 inch in diameter. The second crystal is much larger, typically 3 or 4 inches in diameter. The MPD-Scanner should be asymmetric not only in dimensions but in the use of different scintillators. For example, signal/background can be improved by about a factor of two when the smaller crystal is NaI(Tl) and larger is $CaF_2(Eu)$.

Software for the MPD-Scanner: The two detectors used in the MPD-Scanner according to the invention are the small diameter (0.5–1 inch) primary detector which determines the spatial resolution, and the secondary detector used for coincidence/anticoincidence analysis. The surface of the primary detector is covered with an absorbing mask (of Pb or Cu) with an aperture (usually in the shape of a rectangular slit). When scanning is performed, the computer-controlled mover moves the sample in front of the slit with a step which can be equal to or smaller than the slit width. At each step a measurement is performed, and subsequently the profile is reconstructed.

The acquisition logic is as follows. The triggering is performed from the signal in the primary detector. Each pulse from the primary detector is analyzed for the shape (for background rejection) and amplitude. The trace recorded simultaneously from the secondary detector is also analyzed, and coincidence/anticoincidence analysis is performed. The energy spectra of all non-rejected events in the primary detector and of coincident events are built during the measurement. Before the sample is moved to the next position, the counts in ROIs set for different isotopes are integrated and the data appended to the scan data disk file.

The user interface for the MPD-Scanner includes the scan definition and the data analysis modules. The scan definition module permits the user to preset the geometrical parameters for multiple scans: the starting points, the scan lengths and steps, as well as the measurement times per step (which can be different for different scans), and the user descriptions for each scan. The data analysis module permits viewing the scan profiles in different modes (a profile graph or a simulated autoradiogram). This module also permits analysis of profiles, as well as sending the data to a spreadsheet for customized analysis.

Very high spatial resolution scanning MPD is now discussed. In many applications, a few microns spatial resolution is required. An MPD with such spatial resolution permits considerable improvement in a plurality of biomedical studies, e.g., anatomical and cellular studies. The spatial resolution of MPD-Scanners is generally about 100 microns. The spatial resolution of all detectors is limited by the following effects:

1) thickness of the 2D distribution of the radioisotope.
2) the limited stopping power of the detectors, leading to parallax errors in the crystal;
3) limited stopping power in the aperture, leading to a non-delta transfer function;
4) positioning errors in the mechanical displacement system.

The first error source can be eliminated using devices analogous to those used in conventional optical and electron microscopy. The second source of error is a fundamental limitation leading to positioning uncertainty in all detectors using proximity imaging. This is the main limitation upon the spatial resolution of autoradiography or phosphor imagers. As mentioned above, in the case of beta sources, the range of the particle limits the resolution of classical detectors for all sources but tritium. Obviously, there is a trivial solution, which is to make the scintillator as thin as the required spatial resolution, but this leads to very low detection efficiency.

Use of imaging with apertures partially removes the problem of the range of particles. This solution is especially attractive in the case of soft X-rays wherein the stopping power of gold or platinum film is about 30 times higher than of NaI(Tl) and up to 100 higher than for $CaF_2(Eu)$. However, even in the case of heavy metal films, e.g., gold, platinum, tungsten or lead, a large fraction of the 27 keV photons pass through a 100 microns thick foil. Software which permits creation of images for partially transparent films improves the spatial resolution of MPD-scanner only down to about 50 microns for $I^{125}$.

For further enhancement, a preferred solution is to diminish the energy of the photons used in the image creation. These are found in EC emitters with lower atomic number, e.g., $Fe^{56}$ or $Cr^{51}$. In this case, about 6 keV photons are present, which using gold film can be imaged with a precision of better than 10 microns. Another alternative is the use of $I^{125}$ and $I^{123}$. In this case, not only the L-edge characteristic photons (27 and 31 keV) are present, but also 4 keV K-edge X-rays. Finally, one can use Auger electrons emitted by higher energy CGX sources.

In the case of very soft X-rays, say <15 keV, scintillators are not the best detectors. One can use a hybrid MPD-Scanner where a small silicon detector is covered by a high density film with aperture. The second detector detects only higher energy photons, e.g., 27 and 31 keV photons in the case of $I^{125}$. Thus, it can be a relatively large, say 2–3 inch diameter, scintillator, e.g., $CaF_2(Eu)$.

Alternatively, a gas detector can be used for detection of very low energy X-rays. A windowless gas detector can be used using pressurized gas flowing through the film aperture. This film itself is used as an electrode of the gas detector amplifying system.

A fourth source of errors in the MPD-Scanner is the precision of the mechanical displacement system. Piezoelectric mechanical displacement generators exist with submicron resolution. Additionally, the problem of the precision of mechanical parts of the MPD-Scanner is facilitated in those applications where only relative, rather than absolute indexing, is required.

An exemplary Spatially Resolving MPD (SR-MPD) is now described. The Scintillator-based Spatially Resolving SR-MPD detectors feature low cost, excellent sensitivity and good spatial resolution. The SR-MPD concurrently quantitates up to 50 samples of biological material labeled with CGX isotopes, e.g., $I^{125}$, with reasonable detection efficiency and minimal cross-talk (below 1%). The background is about 0.3 count per sample per day. The spatial resolution of the SR-MPD is about 2–3 mm. The SR-MPD can be successfully applied to analysis of biologicals presented in the form of dot blots or contained in standard 8×12 well microtiter plates.

A preferred SR-MPD according to the invention includes three parts: an auxiliary detector, a spatially resolving detector and data acquisition electronics. The auxiliary detector uses a 3" $CaF_2$ (Eu) scintillator coupled to a low background non spatially resolving PMT. The performance of the auxiliary detector is optimized by selection of a crystal diameter and thickness which provides the best trade-off between detection efficiency and low background. The methods disclosed for the single sample MPD (selection of low background PMT's, use of thin quartz window, special packaging, temperature stabilization of read-out electronics, special design of PMT high Voltage base) are used here. They permit a factor of five decreased background as compared with the commercially available assemblies. The spatially resolving detector includes a thin 2–3" diameter NaI(Tl) crystal coupled to a spatially resolving PMT (SR-PMT). Preferred SR-MPD devices are implemented using a 3" diameter SR-PMT manufactured by Hamamatsu.

To count multiple samples with minimal crosstalk, a lead mask about 1 mm thick is placed on the surface of the SR detector. Coded aperture masks made of tungsten, gold or platinides permit further improvement of spatial resolution. For example, samples arranged as a dot blot are placed next to the apertures in the mask. This configuration allows up to half of the single-sample MPD detection efficiency for each of about 50 samples. One of the problems is non-linear SR-PMT response. To maximize the number of samples measured concurrently the samples can be arranged so that the sample spacing increases towards the outer edge of the SR-PMT. The SR-MPD permits up to 20 times higher throughput than the SS-MPD at about three times the cost.

For $I^{125}$, the X-rays are very soft. This permits imaging when using a parallel hole collimator. The use of SR-PMT's in conjunction with scanning devices permits excellent spatial resolution, down to 0.2 mm. This is adequate for nearly all molecular biology applications. SR-PMT techniques can be adapted to the exacting standards of ultralow-radioactive background applications. SR-PMT's have previously been developed for high counting rate applications, typically 100 cpm, whereas according to the invention they are used at count rates lower than 0.1 cpm. Thus, the radioactive background of the PMT's, vibrational and electromagnetic noise must be rejected and spatial resolution inhomogeneities and artifacts accounted for. The Hamamatsu 3" SR-PMT, model R2486, is preferred. The electronic readout system of the Hamamatsu SR-PMT provides the user with four inputs, from which the coordinates of the detected events can be calculated.

The SR-PMT is physically a 3" device which has however, only an approximately 2.5" diameter active area, i.e., an area in which good spatial resolution can be achieved. The signal drops drastically at about 1.1" from the PMT center which for X-rays leads to drastic artifacts in the measured position of the optical photon cascade in the scintillator. Thus, 2"–2.5" diameter scintillators are optimal for the SR-MPD, and good spatial resolution can be obtained by appropriate hardware and by using iterative position calculation software, described below. For $I^{125}$ this means that 49 samples can be well resolved, as compared with the 32 samples which can be resolved using the manufacturer's electronics and the manufacturer's suggested position calculation software. From the point of view of background, it is very important that the crystal is significantly smaller than the SR-PMT diameter; use of a 2" diameter scintillator leads to three-fold lower background than when using a 3" crystal. Furthermore, the use of a very thin, say 0.5–2 mm thick quartz coupler between the SR-PMT and the scintillator crystal helps diminish background due to beta particles emanating from the PMT glass about five-fold.

An alternative SR-MPD instrument is based on the 5" diameter Hamamatsu SR-PMT's. Spatial resolution is only slightly worse than with the Hamamatsu 3" SR-PMT. It permits considerably more resolved pixels per detector surface than the 3" SR-PMT. The 5" SR-PMT's are not preferred for a low background device. To support the tube against implosion due to atmospheric pressure, the 5" SR-PMT utilizes an approximately 6 mm thick front glass window that is highly contaminated with $K^{40}$, leading to about a factor of four higher radioactive background than with non-spatially resolving 3" PMT's. A larger SR-MPD is preferably based on a 5" SR-PMT made of quartz.

Software for the SR-MPD: The SR-MPD data acquisition software has to process more than two traces for each event. The Hamamatsu SR-PMT has four outputs which in the following are referred to as the signal left (SL), signal right (SR), signal top (ST) and signal bottom (SB). These signals are combined in the SR-MPD detector hardware to obtain the total signal, TS=SL+SR+ST+SB. Thus, the signal acquisition and processing software analyzes six signals, SL, SR, ST, SB, TS and the signal from the non-spatially resolving trigger electronics (TR). The signals from the spatially resolved detector can have very different shape than the signals from the auxiliary detector. The signals from NaI(Tl) are much faster than from $CaF_2(Eu)$. The software uses this dichotomy to better reject the background.

Sum pulse TS and pulse TR from the secondary detector are analyzed for amplitude and shape to reject electronic and other artifacts, while the four original signals from the SR-PMT are analyzed for amplitude only. The amplitude of the sum pulse is roughly proportional to the particle energy and is analyzed in dedicated hardware for compatibility with the source used. However, there is a dependence of the signal on the photon impact position on the crystal. Thus, after the position of the event is established, the amplitude of the total signal is software analyzed and all events with energies outside of the pre-set energy ROI are rejected.

Overall, the different modes of hardware and software event analysis permit rejection of over 95% of the background events. In the case of the non-spatially resolving MPD the main source of background are upsets due to cosmic rays, whereas in the case of the SR-MPD, the main source of background is a combination of electromagnetic interferance and dark currents in the PMT.

The location of the event on the surface of the detector is calculated from the four outputs of the SR-PMT. The first approximation is given by $x_0=(SL-SR)/TS$ and $y_0=(ST-SB)/TS$. However, this approximation is valid only for events with an impact close to the center of crystal, whereas on the edges, there are important position artifacts. Thus, an iterrative position search routine is preferred, wherein the real position is established from:

$$x_i=(a[x_{i-1}]*SL-b[x_{i-1}]*SR)/TS$$

and $$y_i=(c[y_{i-1}]*St-d[x_{i-1}]*SB)/TS.$$

The calibration functions a(x), b(x), c(y) and d(y) have to be established empirically for each SR-PMT. Unfortunately, this function depends also on the source energy. During data acquisition, a 2D image corresponding to the surface of the detector is built. Following the acquisition, the counts in the areas associated with apertures in the mask are integrated to obtain the count rate for each sample, which is then converted to dpm using the calibration data.

The parts of the image corresponding to the apertures and the detection efficiency and background values for each aperture are determined during the calibration of the device by placing samples of known activity into the apertures, acquiring the image, and analyzing it. The software mask construction is performed automatically by the software using a straightforward peak detection routine.

The MPD Imager is now described. Scintillator-based MPD-Imagers feature low cost, excellent sensitivity, high throughput and sub-millimetric spatial resolution. The MPD-Imagers can be used for quantitation of fractionated biological materials, e.g., chromatographic outputs and DNA sequencing gels and blots. The spatial resolution of the MPD-Imager can reach or exceed 0.2 mm.

The MPD-Imager permits sub-millimeter resolution and is appropriate for quantitation of fractionation outputs, e.g., sequencing gels or chromatographic plates. In this device, the SR-MPD is coupled to a high precision 2D mover. High resolution is obtained by using a multi-aperture pattern; each event is assigned to a spatial ROI and reconstructed from the knowledge of the position of the mover. The MPD-Imager is much more sensitive and faster than phosphor imagers, which are increasingly used in molecular biology. DNA sequencing blots were quantified using the MPD-Imager and dot/bar patterns were spatially resolved at few zeptomole level.

A preferred MPD-Imager includes the following subsystems: as shown in FIGS. 13, 13A, 14, and 14A 2.5" NaI(Tl) scintillator 73 with 3" spatially resolving PMT.; 88, optionally with quartz window 72

3" $CaF_2(Eu)$ scintillator with low radioactive background PMT read-out;

a coded aperture/separator/shield subsystem comprising heavy metal film 89 with coded aperture 96 as illustrated in FIGS. 13 and 13A or film 91 with multiaperture slit array 97 as illustrated in FIGS. 14 and 14A;

a 2D mover system with about 100 microns relative movement precision optional, shown in FIG. 14 as 2D moving table 79 with 2D sample 78;

read-out electronics, 80 including 3 DSO 58 cards;

a data acquisition/analysis subsystem (e.g., PENTIUM processor).

The MPD-Imager permits dynamic acquisition of information with excellent S/B. It allows system resolution to be directly proportional to the precision of the aperture movement upon the surface of the blot. Typically the collimator (slit) width is of the same order of magnitude as the physical width of the DNA band. A stationary collimator measures the total signal coming into the entire slit area, e.g., the signal from 4 $mm^2$ of the blot for a 1 mm×4 mm slit. The situation is different when time resolving detectors are used. As the collimator moves to a new position across the blot, one measures a relative increase or decrease of activity in the area of the blot that is opened to the detector by the movement of the leading edge of the slit. On the other hand, some part of the blot is no longer exposed because it is now shielded by the trailing edge of the slit. Thus, knowledge of the time of signal arrival permits differential de-convolution of the blot activity and sub-millimetric spatial resolution when imaging blots. The "system" spatial resolution is directly proportional to the accuracy of the movement of the scanner; the MPD-Imager has about 100-micron accuracy.

The intrinsic resolution of the MPD-Imager is now discussed. This parameter can be measured using "radioactive" ink in an HP Inkjet printer to generate a series of well defined patterns enabling comparison of the MPD-Imager and phosphor imager. A relatively low surface activity of 10 picoCurie per $cm^2$ was used. The test pattern consisted of equally spaced horizontal bars of 3 mm, 2 mm and 1 mm, with the bar spacing equal to the bar width. The pattern and its image were obtained with the MPD Imager and a Molecular Dynamics brand phosphor imager. After a 48 hour exposure, the phosphor imager detected the 3 mm pattern well, although the background is quite high. It only partially resolves the 2 mm pattern, and the 1 mm pattern is unmeasurable. In contrast, the MPD-Imager clearly resolved even the 1 mm pattern with S/B of about 10. The 0.5 mm pattern is also resolved, but requires a longer scanning time.

Software of the MPD-Imager: The MPD-Imager combines the functionality of the SR-MPD and that of the MPD scanner. The mask on the primary (SR) detector has an array of apertures, defining the spatial resolution of the imager. The 2D sample is placed on a computer-controlled mover which sequentially places the sample in the measurement positions. In each position, the counting is performed for a pre-set time (using the same acquisition logic as that for the SR-MPD). The count rates for all apertures are obtained and stored in a disk file.

Following the scan, the image is reconstructed from the counting data. The resolution-defining aperture pattern is such that, to obtain a continuous image, the pixels have to be interleaved in both X and Y dimensions. The pattern should allow such interleaving, although it does not necessarily have to be rectangular. For each available resolution mask, the system has a separate calibration file containing the software mask defining the mapping of the apertures to the image surface. The mask is constructed automatically by the software during calibration.

The user interface allows selecting a rectangular area to be scanned and pre-setting the counting time for each pixel. The data analysis module reconstructs the image from the counting data, permits visualization of the image in false colors, shades of grey, a contour map, or as a 3D surface, as well as storing the image in a number of standard formats for analysis by other image processing programs.

A Large MPD-Imager is now discussed. For a large MPD-Imager, the spatially resolving part of the system is engineered to enable higher throughput for large 2D fractionation outputs. Commercial value of MPD-Imagers depends on providing throughput sufficient to perform overnight analyses of 2D gels and blots at the 10–19 mole level. To achieve this, one may use a large area, say 12 inch×8 inch, MPD-Imager.

Three types of large spatially resolving gamma detectors which can be used in a large MPD-Imager are: detectors using one or several SR-PMT's; detectors using a few tens of small diameter PMT's in an Auger camera configuration; and detectors using microchannel plates and CCD imagers. Use of a preferred new scintillator, Yttrium Aluminum Perovskite doped with Cerium (YAP(Ce)), permits a large MPD-Imager with very good spatial resolution and exceptionally low background.

The beneficial characteristics of a large MPD-Imager are:
1) lowest possible radioactive background, permitting zeptomole sensitivity in a plurality of biological tasks;
2) instrumentation permitting high throughput even for the samples with very low levels of radioactivity;
4) low cost, user friendly devices with software facilitating biological tasks.

In one implementation of a large MPD-Imager according to the invention, a single computer controls the concurrent and coordinated operation of four spatially resolving sub-units. This is made possible by the relatively low count rates in targeted applications at count rates of between a few tens per second to a few counts per minute per pixel. Pulse shape analysis takes only about 100 microseconds and can be diminished to about 10 microseconds. Losses due to pile-up of events in different detectors can be fully accounted for.

The number of detectors in the multi-detector instrument is limited by the DSO 58 bus throughput, pulse shape analysis time including speed of the controlling microprocessor, the number of available bus slots, and cost considerations. A four detector MPD may be interfaced on a PENTIUM processor 120 MHz in full-tower configuration and motherboard with 12 bus slots, for example. Four SR-PMT's can be multiplexed on a single computer.

Large MPD-Imager based on several SR-PMT's: This exemplary embodiment has four modules:
 auxiliary detector
 spatially resolving detector built of four sub-assemblies;
 mechanical mover assembly;
 data acquisition and processing unit.

The auxiliary detector is based on $CaF_2(Eu)$ scintillators coupled to a plurality of selected, low background PMT's. Preferred auxiliary detector modules are as follows. First, a large, say 8"×8" crystal is coupled by means of appropriate light guide to a 6" PMT. This is the simplest and lowest cost implementation, but it leads to a rather large device. Second, a single $CaF_2(Eu)$ scintillator is coupled to an array of PMT's. For example, a 9"×9" scintillator can be coupled to an array of nine matched 3" PMT's. Third, a 8"×8" crystal is coupled to the array of 16 matched 2" PMT's. The outputs of all PMT's are summed and pulse height and pulse shape are analyzed by low noise electronics, including DSO 58. Pulses of appropriate amplitude can be used as the trigger for acquisition and analysis of data from the spatially resolved detector.

It is preferred to use "matched" PMT's with serving electronics. When stimulated by a particle of a given energy, the amplitude and shape of the pulses should be essentially the same. For example, temporal delays should be the same to within 100 nsec, the amplitude the same to within 10% and shape of pulses almost identical. To overcome the requirement for matched PMT's, the trigger detector can consist of four sub-assemblies, each consisting of 4"×4" $CaF_2(Eu)$ crystals coupled to a single, 4" PMT.

Preferably, the PMT is square or hexagonal, but cylindrical PMT's can be used with optical coupling using an appropriate acrylic waveguide. In the case of a mosaic of four 4"×4" detectors, instead of laborious matching of PMT's, much simpler computer calibration can be used. However, inhomogeneities of scintillation detectors are always largest close to the borders of the scintillator, i.e., the mosaic trigger detector may have somewhat lower detection efficiency and lower energy resolution, which negatively influences the background.

NaI(Tl) can be used for its good stopping power and the best energy resolution among scintillators. An exemplary large area spatially resolving detector module uses a 8"×6" active area to permit imaging of the full surface of a typical sequencing gel. An exemplary mosaic SR-detector uses four smaller SR-PMT's. The detector assembly includes four spatially resolving detector modules, each consisting of a 4"×3" NaI(Tl) crystal read out by a Hamamatsu square SR-PMT. The square SR-PMT has an active area of 60×55 mm, wherein a spatial resolution of 2–3 mm is expected. Square rather than round 3" SR-PMT's are preferred because they permit better coverage of the surface. Both the electronics and the imaging properties of square and round SR-PMT's are almost identical, and can use basically the same electronics and software.

To economize the slots available in the control computer, all of the electronics for a single SR-PMT is preferably placed on a single card. The large MPD-Imager uses multiplexing to diminish the number of electronics cards to economize space, facilitates handling of heat-load problem and diminish the cost of the device.

Use of a single PENTIUM processor 120 Mhz assumes that a single full length card contains the signal conditioning and coincidence circuitry for two detectors, i.e., four channels. Even a 12 slot motherboard lacks enough ISA slots because the DSO 58 features two channels per card. A preferred DSO card 58 has 4 channels, each 50 MHZ. It is based on CMOS elements to considerably diminish heat dissipation. Four channels of DSO can then fit on a single full length card with the PCI bus.

Multiplexing electronics is preferred with eight thresholds providing flags for software. For each detector, there is separate delay and coincidence circuitry, permitting both non-coincident and coincident counting. A set of 40 flags (outputs from 8 thresholds for each SR-PMT, four coincidence signals and four thresholds for sum signals) are then transferred to the computer permitting on-line event reconstruction. The signals from all SR-PMT's are summed and the outputs are input into the 3 DSO's. This permits pulse shape analysis using the present software. With the availability of a four channel DSO, only three cards are necessary to process the information from four SRPMT's. By using polarity encoding to process the data from two SR-PMT's, only two 4-channel DSO cards are necessary to process the information about the pulse amplitude in the SR-PMT's (sum of all 4 outputs) and non-spatially resolving PMT.

To manage thermal load, a few fan cards may be placed between the DSO and SCPC cards. The challenge of electromagnetic interference from the fan cards (2 AC motors per card) is quite difficult in the case of a device which shows one count per day background, but electromagnetic shielding is appropriate. Cooling elements based on Peltier effect (no AC currents) offer a less difficult solution.

Software preferably permits "seamless" image reconstruction, taking into account the non-active area between detector units, and is consistent with use of computers based on the Intel P6 processor.

Multiplexing several SR-PMT based detectors and building a large-area detector requires faster pulse shape analysis. In single detector systems, DSO's with long transfer times (200 microseconds/pulse) are adequate. The large MPD-Imager uses DSO's with a faster computer interface. To fully utilize this advantage requires fast drivers and accelerated pulse processing. The logic of the pulse shape rejection is therefore optimized for the multiplexed systems by taking into consideration the additional information from all PMT's and changing the order of the tests. Further optimization of the pulse shape analysis code is achieved by utilizing the highly efficient native PENTIUM and P6 processor instructions.

Because the MPD is targeted for quantitation/imaging of very small amounts of radiolabel, statistical analysis of data from sources with poor signal-to-background ratio (S/B) and significant uncertainty is important for correct data interpretation. It is thus preferred that the MPD-Imager includes software statistical analysis functions and routines for image enhancement and recognition. The latter are preferably based on such AI techniques as simulated neural networks and/or iterative use of memory matrices.

Large MPD-Imager based upon time delay techniques: Some limitations of the large MPD-Imager relate to the SR-PMT's used—high radioactive background due to contamination of Hamamatsu tubes with $K^{40}$ and difficulty of calibration due a large dead zone between the four separate SR-PMT's.

Anger cameras are a popular class of large gamma detectors wherein the surface of a single large NaI(Tl) crystal is populated with many photomultipliers. When a photon is absorbed in the crystal, the light is shared between several PMT'S. The center of gravity of the light pulse is established by finding the four PMT's with the largest signal and reconstructing the event from the ratio of their signal amplitudes. Spatial resolution is limited by crystal thickness, light yield and the number of PMT's used. Typical Anger camera parameters are: NaI(Tl) crystal thickness=0.5 inch, number of PMT's=36–64; intrinsic spatial resolution=2–3 mm. For $I^{125}$, the crystal thickness can be reduced to 1.5 mm, which improves spatial resolution down to 1 mm. In the simplest implementation, the number of ADC's is the same as the number of PMT's, say twenty-four 2" PMT's. More complicated schemes are envisioned according to this aspect of the invention, in which a large number of thresholds are used but only eight ADC channels are necessary. An Anger camera based MPD-Imager is preferred, but the required electronics are complex and due to the large number of channels, pulse shape analysis is difficult to implement.

An alternative embodiment is a high performance spatially resolving gamma detector using a pulse delay technique and DSO to reconstruct the photon position, and the new scintillator material, yttrium aluminum perovskite activated with Ce (YAP(Ce)). It provides a high light yield (about 50% of NaI(Tl)) and is about five times faster than NaI(Tl). Also, multichannel, high speed and large memory DSO cards compatible with Intel PENTIUN processor or P6, e.g., two channel, 150 MHz/channel with 32 kb of memory from Gage Inc., may be used.

Low attenuation analog delay elements are readily available with delay times from a few tens of nanoseconds to a few microseconds. With a triangularly shaped YAP pulse (rise time of 10 ns and fall time of 50 ns), the outputs of up to 10 PMT's can be digitized with a single channel of DSO. Thus, two DSO cards encode the output of up to 40 PMT's and permit highly reliable, nominally 8 bit quantitation. One can use modulo four encoding, where the four neighboring PMT's are each encoded upon different DSO channels. Thus, a compact, relatively low cost implementation of Anger camera is possible.

Using a YAP scintillator crystal for the MPD-Imager, signal pulses have about a 50 nsec duration. This allows multiplexing signals from several PMT's onto a single DSO input through the use of constant delays. Summing is preferred for the 6 outputs from each of the 4 rows of PMT's delayed by 0, 100, 200, 300, 400 and 500 nsec, respectively. This pulse train is then sent to a DSO input channel and to the trigger card (SCPC) which produces triggers for all DSO's in the system. For the second (coincidence) detector a NaI (Tl) crystal of the same size (12"×8") is read out by four 3" PMT's. The outputs of these PMT's are summed and the sum signal used to establish whether the event is coincident. Additionally, this pulse is pulse shape analyzed to reject background. All thresholds, digital delays, and gains are under software control through the SCPC. The computer decodes the multiplexed signals acquired by the DSO's and finds the coordinates of each detected event through analysis of the pulse amplitudes in all 24 PMT's.

To avoid the problem of radioactive background, the large MPD-Imager uses carefully selected PMT's based on radioactive background, detection efficiency, energy resolution, homogeneity over the photocathode surface, dark current, and long term stability. Preferred photomultipliers include either 1" or hexagonal 2" PMT's from EMI. For an MPD-Imager of 12 inches×8 inches, the preferred configuration is a grid of 2" hexagonal PMT's with 2" center to center spacing, leading to a 6×4 array of PMT's. Alternatively, for 1" PMT's spaced 1.5" center to center, an array of 8×5 PMT's is preferred. Cost is much lower for 2" PMT's because the electronics are much simpler and only two DSO cards are needed. On the other hand, the 1" PMT provides slightly better spatial resolution and about a factor of 2 lower radioactive background.

The large MPD-Imager preferably uses dedicated data acquisition and processing software. The signals from several PMT's are encoded using delay lines and multiplexed onto one DSO channel. The acquisition software processes a succession of pulses using appropriate pulse-shape rejection and baseline restoration procedures. Although this task is simplified by the constant delay times between signals, additional consistency analysis of whether the pulses in the "train" are due to a single event, and even some deconvolution may be required. A reliable and highly efficient process is preferred for computing the coordinates of each event based on the data from multiple PMT'S. Special provision is made for storing and processing much larger volumes of data, as well as for compensating for the inevitable non-uniformities in the large-area detector. These routines can be optimized by replacing most computations by look-up tables, and coding them as much as possible, within the limits of integer arithmetic, in assembly language to diminish the dead time. Pulse processing, spectrum analysis and image reconstruction are otherwise as for the single-detector SR-MPD system.

Thus it can be seen that a multiphoton detector of the invention provides numerous advantages. These include low background and high sensitivity, high detection efficiency, high energy resolution, excellent reproducibility and stability, low cost, and small size.

While this description contains many specific details, these should not be construed as limitations on the scope of the invention, but rather as examples of preferred embodiments. Many other variations are possible. The scope of the invention should be determined not by the embodiments described and illustrated, but by the claims as broadly construed together with their equivalents.

We claim:

1. An apparatus for detecting a radioisotope in a sample, comprising:
   (a) a detector assembly including two opposed detectors for detecting emissions from the radioisotope in the sample when the sample is placed in a sample holder between the detectors, and for converting the emissions into electric output pulses, and
   (b) a pulse shape analyzer, operatively connected to the detectors, for analyzing the output pulses from each detector and comparing them to predetermined acceptance criteria for the two detectors, rejecting pulses that do not satisfy the predetermined acceptance criteria, and counting output pulses that satisfy the predetermined acceptance criteria.

2. An apparatus for detecting a radioisotope in a sample according to claim 1, wherein the counting is done separately for pulses corresponding to coincident and non-coincident emissions.

3. An apparatus according to claim 2, wherein counted coincident pulses are used to build a three dimensional scatter plot matrix.

4. An apparatus according to claim 1, wherein at least one of the detectors comprises a thin inorganic scintillator crystal that produces a signal when impacted with an emission from the radioisotope.

5. An apparatus according to claim 4, wherein the scintillator is selected from the group consisting of NaI(Tl), CsI(Tl), CaF$_2$(Eu), and YAP.

6. An apparatus according to claim 4, further comprising a photosensor, wherein a low radioactive background optically transparent window is placed between the scintillator and the photosensor.

7. An apparatus according to claim 6, wherein the window comprises quartz or a high density (>4 g/cc) and high atomic number (greater than about 50) optically transparent material.

8. An apparatus according to claim 6, wherein the window is made of material selected from the group consisting of high-purity GeO$_2$ or germanium-based glass, high density glasses based on lead, PbF$_2$, and undoped bismuth germanite (BGO), and wherein the windows are optically connected to the scintillator and the photosensor with an optical grease that matches the optical properties of the photo sensor.

9. The apparatus according to claim 6, wherein the scintillator and photosensor are covered by at least three subsequent layers of nontransparent plastic tape followed by thin metal tape.

10. The apparatus according to claim 9, wherein the metal tapes include a special metal tape with high magnetic permeability, and the assembly is covered by a few layers of copper tape.

11. The apparatus according to claim 4, wherein the surfaces of the scintillator are covered with a thin low radioactive background housing of density less than about 0.1 g/cm$^2$ and made of elements having molecular weight below about 13.

12. The apparatus of claim 11, in which the housing comprises an element selected from the group consisting of beryllium, aluminum, and plastic.

13. An apparatus according to claim 1, wherein at least one detector further comprises a photosensor.

14. An apparatus according to claim 13, wherein the photosensor is a photomultiplier, a large surface photodiode, or an avalanche photodiode.

15. An apparatus according to claim 14, wherein the spatially resolving photosensor is a photomultiplier having four outputs, and the position of impact of an X-ray is calculated from the iterative algorithm, the first approximation given by $x_0=(SL-SR)/TS$ and $y_0=(ST-SB)/TS$ and following approximations obtained from:

$$x_i=(a[x_{i-1}]*SL-b[x_{i-1}]*SR)/TS$$

and $$y_i=(c[y_{i-1}]*ST-d[x_{i-1}]*SB)/TS$$

wherein SL=signal left, SR=signal right, ST=signal top and SB=signal bottom (SB) and TS=SL+SR+ST+SB and where a(x), b(x), c(y) and d(y) are the calibration functions established empirically for the spatially resolving photomultiplier.

16. An apparatus according to claim 15, wherein the true energy of an X-ray is calculated from the impact position of the X-ray using the look up calibration tables established empirically for the spatially resolving photomultiplier.

17. An apparatus according to claim 13, wherein the photosensor is a photomultiplier tube made of low radioactive material selected to have radioactivity lower than about 10 pCi.

18. An apparatus according to claim 17, wherein the diameter of the photomultiplier is about 2" to about 3".

19. An apparatus according to claim 17, wherein the diameter of the scintillation crystal is about 7% to about 25% smaller than the diameter of the photomultiplier tube.

20. An apparatus according to claim 1, wherein the detector assembly comprises a separator placed between the detectors; and a shield array isolating the detectors from external radiation.

21. An apparatus according to claim 20, wherein the detectors are identical $CaF_2(Eu)$ crystals with a thickness less than about 0.5 inch.

22. The apparatus according to claim 1, wherein the detector assembly is placed within a shield of which at least one of the components is a metal having an atomic number greater than about 61, or a compound thereof having a density greater than about 5 g/cc, and the shield materials are selected to have a radioactive background less than about 10 pCi/g.

23. The apparatus according to claim 22, whereip the shield comprises subsequent layers of materials with low atomic number (Z<20), medium atomic number (21<Z<60) and high atomic number (Z>61), and where the high atomic number layer is the most external.

24. The apparatus according to claim 23, wherein the material with low atomic number comprises copper and the material with medium atomic number comprises tin.

25. An apparatus according to claim 1, wherein a separator absorbing the majority of X-rays is sandwiched between the detectors.

26. The apparatus according to claim 25, wherein the separator comprises a layer of a high atomic number material (Z>61) with a thickness larger than about 2 mm.

27. The apparatus according to claim 26, wherein the separator is cladded on both surfaces with thin layers of materials with medium and low atomic number.

28. The apparatus according to claim 27, wherein the low and medium atomic number materials are copper and tin, respectively.

29. The apparatus according to claim 25, wherein the sample holder is a hole in the separator.

30. The apparatus according to claim 25, wherein the separator has two parts configured to receive the sample holder.

31. The apparatus according to claim 30, wherein the sample holder is made of materials having atomic number below about 13, and low radioactive background.

32. The apparatus according to claim 30, wherein the sample holder is a plastic tray with dimensions of between about 12×13 mm and about 75×100 mm.

33. The apparatus according to claim 25, wherein the sample holder is a narrow microcapillary with a receptacle tip sized to contain up to about 0.1 cm$^3$ of liquid.

34. The apparatus according to claim 1, wherein at least one of the detectors is a phoswich module comprising two optically coupled scintillators with different characteristic response times.

35. The apparatus according to claim 34, wherein the scintillator closer to the sample is a very thin scintillator with high energy resolution, the second scintillator is a thick, high stopping power scintillator, and the two scintillators are separated by a few millimeters of optically transparent material with low radioactive background.

36. An apparatus according to claim 35, wherein the scintillator closer to the sample is NaI(Tl) or $CaF_2(Eu)$, the second scintillator is CsI or BGO, and the optically transparent material is acrylic plastic or quartz.

37. An apparatus according to claim 35, further comprising a fast, low noise shaping amplifier that amplifies the signal from the phoswich, and the pulse shape analyzer localizes the scintillator element inside the phoswich within which the photon is absorbed.

38. An apparatus according to claim 1, wherein at least one of the detectors comprises a semiconducting detector.

39. An apparatus according to claim 1, wherein at least one of the detectors comprises a gas detector.

40. An apparatus according to claim 1, wherein each detector further comprises a low noise preamplifier that shapes signals into characteristic triangular output pulses with rise times shorter than about 200 nsec and fall time between about 0.5 and about 5 microseconds, and matches the pulse shapes and amplitudes in both detectors to better than about 10%.

41. An apparatus according to claim 40, wherein the pulse shape analyzer comprises single channel analyzers (SCAs) that analyze the triangular output pulses for amplitude, and a coincidence circuit with a well defined time window that analyzes the output pulses and provides a trigger pulse when it receives coincident output pulses.

42. An apparatus according to claim 41, wherein the pulse shape analyzer further comprises a spectrum analyzer having a speed of at least about 10 MHz per channel that stores in memory and analyzes the shape of the triangular output pulses when it receives a trigger pulse from the coincidence circuit.

43. An apparatus according to claim 42, wherein the spectrum analyzer is an analog-to-digital converter or digital storage oscilloscope.

44. An apparatus according to claim 42, wherein the pulse shape analyzer further comprises a computer having a fast memory into which data from the spectrum analyzer is transferred.

45. An apparatus according to claim 1, wherein the pulse shape analyzer analyzes output pulse shape criteria from the group consisting of pulse amplitude, total pulse width, shape of the rising part of the pulse, shape of the falling part of the pulse, delay between the pulses from the two detectors, pulse multiplicity, and pre-pulse trace; and compares the output pulse criteria with predetermined acceptance criteria, accepts the output pulse for counting if the acceptance criteria are satisfied, and rejects the output pulse if the acceptance criteria are not satisfied.

46. An apparatus according to claim 45, wherein the acceptance criteria are obtained from a high energy photon pulse shape, and comparison of the signal pulse to the acceptance criteria uses a least squares technique.

47. An apparatus according to claim 1, wherein the sample holder comprises an encapsulated sample spot and is thin enough and made of low enough density/low enough atomic number material that the sample holder absorbs negligible amounts of X-rays and does not contaminate the detectors.

48. An apparatus according to claim 47, wherein the sample spot is encapsulated with a thin layer of material with very low radiactive background less than about 0.1 pCi/cm$^2$ and low atomic number.

49. An apparatus according to claim 48, wherein the encapsulating material is selected from the group consisting of spray, lacquer, acrylic paint, silicon paint, and varnish.

50. An apparatus according to claim 48, wherein the sample is affixed to a solid, flat sheet within an encapsulating pouch made from a thin film selected from the group consisting of berylium films thinner than about 1 mm, plastic films thinner than about 0.5 mm, and aluminum films thinner than about 0.2 mm.

51. An apparatus according to claim 1, wherein one of the detectors comprises a scintillator crystal and is substantially smaller than the other detector, and further comprising a thin film of high density/high atomic number heavy metal having a small aperture placed in front of the small detector for scaning the sample.

52. An apparatus according to claim 51, wherein both detectors comprise scintillator crystals of $CaF_2(Eu)$ with thickness less than about 3 mm, and diameters between about 0.5 and about 1 inch for the smaller crystal, and between about 2 and about 3 inches for the bigger crystal.

53. A scanning apparatus according to claim 52, wherein the small scintillator is thinner than about 0.1 mm, is sensitive to Auger electrons or very low energy X-rays (E<10 keV), and has a diameter between about 0.1 and about 0.5 inch.

54. A scanning apparatus according to claim 51, wherein the pulse shape analyzer has two modes, an OR mode accepting both non-coincident and coincident pulses for counting, and an AND mode accepting only coincident pulses for counting; and further comprising a sample mover adapted for holding and moving the sample holder in two dimensions with spatial resolution adequate to present essentially flat samples to the aperture in front of the small scintillation crystal; and a controller that identifies the position of the sample mover and permits correlation with the count rate for each position; and optimizes the time of data acquisition for each sample position such that data acquisition can be stopped when the accumulated data reaches a predetermined signal to background ratio or signal to statistical uncertainty ratio; and the pulse shape analyzer and controller present the acquired data as a two dimensional image.

55. A scanning apparatus according to claim 54, wherein the sample mover and the controller cooperate to permit two scans of the samples to be performed, first with low spatial resolution, and second with higher spatial resolution in selected areas in which the count rate is above a predetermined value.

56. An apparatus according to claim 1, wherein the detector assembly comprises a silicon scintillator or spatially resolving CCD detector thinner than 0.1 mm, sensitive to Auger electrons or very low energy X-rays (E<10 keV).

57. An apparatus according to claim 56, wherein the CCD detector is located between the sample holder and one of the opposed detectors.

58. A spatially resolving apparatus according to claim 1, adapted for a plurality of samples arrayed in a two dimensional pattern, wherein at least one of the detectors comprises a scintillator with a high density/heavy metal mask affixed to it, the mask having a coded aperture pattern corresponding to the pattern of the samples, and wherein the scintillator is coupled with a spatially resolving photomultiplier tube having a plurality of outputs each operatively connected to a matched low noise amplifier, the outputs of which are summated electronically into a sum output, and the individual and sum outputs are input to multichannel spectrum analyzers.

59. An apparatus according to claim 58, wherein the spectrum analyzers are analog-to-digital converters or digital storage oscilloscopes.

60. An apparatus according to claim 58, wherein the amplified output pulses from the spatially resolving PMT are compared with "standard shape" pulses according to pulse shape acceptance criteria, and only events satisfying the "standard shape" condition in both the spatially resolved and non-spatially resolved PMTs are accepted and used to build a two dimensional sample image.

61. An apparatus according to claim 60, wherein the amplified pulses from the spatially resolving PMT outputs are digitized by an appropriate spectrum analyzer and are stored in computer memory and subsequently used to build a two dimensional sample image.

62. An apparatus according to claim 58, wherein the diameter of the scintillator is at least 0.5 inch smaller than the size of the spatially resolving photomultiplier.

63. An imaging apparatus according to claim 58, wherein the scintillator has affixed to it a coded aperture mask made of high density/high atomic number film with a regular pattern of up to about 50 holes or slits; the sample holder is a flat two dimensional array of samples; and further comprising a computer-controlled mover which sequentially places samples in measurement positions in front of the aperture mask for a pre-set time.

64. An imaging apparatus according to claim 63, further comprising an imaging analyzer wherein the image is reconstructed from the counting data; the resolution-defining aperture pattern is such that to obtain a continuous image the pixels have to be interleaved in both X and Y dimensions and the pattern allows interleaving; for each available resolution mask the system has a separate calibration file containing the software mask defining the mapping of the apertures to the image surface; a user interface allows selecting a rectangular area to be scanned and pre-setting the counting time for each pixel; and a data presentation system permits visualization of the image in false colors, shades of grey, a contour map or as a 3D surface, and stores the image in a number of standard formats for analysis by other image processing programs.

65. An apparatus according to claim 1, wherein one of the detectors is a Ge-semiconducting detector optimized for detection of X-rays.

66. An apparatus according to claim 65, wherein the Ge-semiconducting detector is less than about 0.5 inch thick and uses a cryostat with thin beryllium or aluminum windows.

67. An apparatus according to claim 1, wherein one of the detectors is a silicon detector.

68. An apparatus according to claim 1, wherein one of the detectors is a spatially resolving gas detector.

69. An apparatus according to claim 68, wherein the spatially resolving detector is a thin self-limiting streamer chamber, wherein the spatial resolution is obtained by imaging, using a CCD.

70. An apparatus according to claim 1 wherein the detector assembly comprises means for holding samples sandwiched between means for converting the emissions from the isotope to electrical output pulses, and the pulse shape analyzer comprises means for counting and timing the output pulses, means for normalizing output pulse amplitude to fall within a predetermined range over a baseline and to correlate with the energy of the emissions, means for generating a first trigger pulse when there is an output pulse having an amplitude which exceeds a predetermined threshold value, and generating a second trigger pulse when there are two substantially simultaneous output pulses having respective amplitudes which exceed the predetermined threshold value, and rejecting output pulses that do not exceed the predetermined threshold value, means responsive to a trigger pulse for capturing a predetermined number of subsequent normalized output pulses, and means for analyzing the captured output pulses based on predetermined isotope and system-dependant acceptance criteria selected from the group consisting of pulse shape, height, coordinates, and coincidence, means for counting pulses that satisfy the predetermined isotope and system-dependant acceptance criteria and rejecting pulses that do not satisfy the acceptance criteria.

71. An apparatus according to claim 70, further comprising means for shielding the detectors from radioactive background.

72. An apparatus according to claim 70, further comprising means for absorbing the majority of external X-rays.

73. An apparatus according to claim 1, wherein the sample holder has a plurality of holes ordered into an easily distinguished pattern, such that samples to be studied can be placed adjacent to the holes.

74. An apparatus according to claim 73, further comprising a separator absorbing the majority of X-rays, between the opposed detectors, and having a hole pattern corresponding to the pattern in the sample holder, wherein the sample holder aligns samples blotted upon an appropriate thin film with a pattern corresponding to the pattern in the sample holder such that the sample pattern is aligned with the holes in the sample holder and the separator.

75. An apparatus according to claim 74, wherein the sample holder has two parts, each with identical hole patterns, and the blotted film is placed between these two parts.

76. An apparatus according to claim 1, wherein the detector assembly comprises for each detector a preamplifier, amplifier and shaping amplifier.

77. An apparatus according to claim 1, wherein the pulse shape analyzer comprises means for analysing each pulse shape record by at least one software module having acceptance criteria, rejecting a pulse on-line if it does not satisfy the acceptance criteria of all the software modules utilized, and counting the pulse if it satisfies the acceptance criteria of all the software modules utilized.

78. An apparatus according to claim 77, wherein the at least one software module is selected from the group consisting of:
   a) analyzer of pulse amplitude;
   b) analyzer of the total pulse width;
   c) analyzer of the shape of the rising part of the pulse;
   d) analyzer of the shape of the falling part of the pulse;
   e) analyzer of the delay between the pulses from the two detectors;
   f) analyzer of pulse multiplicity;
   g) analyzer of the pre-pulse trace; and
   h) comparator of the pulse shape with a standard high energy photon pulse shape using a least squares technique;
individually or in combination.

79. An apparatus according to claim 1 for selective quantitation of a coincident gamma/X-ray (CGX) emitter in a sample, wherein the detector assembly comprises
   (a) means for detecting coincident gamma and x-ray emissions from the CGX emitter as output pulses in separate radiation detectors, and the pulse shape analyzer comprises
   (b) means for analyzing the shape and height of the output pulses from the detectors,
   (c) means for discriminating and rejecting non-coincident output pulses,
   (d) means for discriminating and rejecting spurious coincident output pulses, and
   (e) means for using the remaining output pulses to quantify the presence of the CGX emitter in the sample.

80. An apparatus according to claim 1, wherein the radioisotope is selected from the group consisting of the lighter electron capture (EC) isotopes $Be^7$ (53.6 d), $Na^{22}$ (2.58 y), $Ar^{37}$ (34.3 d), $V^{49}$ (330.0 d), $Cr^{48}$ (23.0 h), $Cr^{51}$ (27.8 d), $Mn^{52}$ (5.6 d), $Mn^{54}$ (291.0 d), $Fe^{52}$ (8.0 h), $Fe^{55}$ (2.7 y), $Co^{55}$ (18.0 h), $Co^{56}$ (77.3 d), $Co^{57}$ (270.0 d), $Co^{58}$ (71.0 d), $Ni^{56}$ (6.4 d), $Ni^{57}$ (1.5 d), $Cu^{64}$ (12.8 h), $Zn^{62}$ (9.3 h), $Zn^{65}$ (245.0 d), $Ga^{66}$ (9.5 h), $Ga^{67}$ (78.0 h), $As^{71}$ (62.0 h), $As^{72}$ (26.0 h), $As^{73}$ (76.0 d), $As^{74}$ (18.0 d), $Se^{72}$ (8.4 d), $Se^{75}$ (120.0 d), $Br^{76}$ (16.5 h), $Br^{77}$ (2.6 d), $Kr^{76}$ (10.0 h), $Kr^{79}$ (1.6 d), $Rb^{82m}$ (6.3 h), $Rb^{83}$ (83.0 d), $Rb^{84}$ (33.0 d), $Sr^{82}$ (25.5 d), $Sr^{83}$ (1.6 d), $Sr^{85}$ (64.0 d), $Y^{83}$ (108.0 d), $Y^{46}$ (14.6 h), $Y^{87}$ (3.33 d), $Zr^{88}$ (85.0 d), $Zr^{89}$ (3.29 d), $Nb^{92}$ (10.1 d), $Tc^{93m}$ (60. d), $Tc^{96}$ (4.3 d), $Tc^{99m}$ (6.0 h), $Ru^{97}$ (2.9 d), $Rh^{99}$ (16. d), $Rh^{100}$ (21. h), $Rh^{102}$ (206 d), $Pd^{100}$ (4.0 d), $Pd^{101}$ (8.5 h), $Pd^{103}$ (17 d), $Ag^{105}$ (40 d), $Ag^{106m}$ (8.3 d), $Ag^{108m}$ (>5 y), $Cd^{107}$ (6.7 h), $Cd^{109}$ (470 d), $In^{111}$ (2.81 d), $In^{113}$ (118 d), $Sn^{113}$ (118 d), $Sb^{119}$ (158 d), $Sb^{122}$ (2.8 d), $Te^{118}$ (60 d), $Te^{119}$ (45 d), $Te^{121}$ (17 d), $I^{123}$ (4.2 d), $I^{125}$ (60 d), $I^{126}$ (13.2 d), $Cs^{132}$ (6.5 d), $Ba^{128}$ (2.4 d), $Ba^{131}$ (11.6 d); the EC isotopes of lanthanides $La^{135}$ (19.8 h), $Ce^{133}$ (6.3 h), $Ce^{134}$ (3.0 d), $Ce^{135}$ (22.0 h), $Ce^{137}$ (9.0 h), $Ce^{139}$ (140 d), $Nd^{140}$ (3.3 d), $Pm^{143}$ (265 d), $Pm^{144}$ (440 d), $Pm^{145}$ (18 y), $Pm^{146}$ (710 d), $Pm^{158m}$ (40.6 d), $Sm^{145}$ (340 d), $Eu^{145}$ (5.6 d), $Eu^{146m}$ (1.58 d), $Eu^{146}$ (4.6 d), $Eu^{147}$ (24 d), $Eu^{148}$ (54 d), $Eu^{149}$ (120 d), $Eu^{150m}$ (14 h), $Eu^{150}$ (5 y), $Eu^{152}$ (13 y), $Gd^{146}$ (48 d), $Gd^{147}$ (35 h), $Gd^{149}$ (9 d), $Gd^{151}$ (120 d), $Gd^{153}$ (200 d), $Tb^{151}$ (19 h), $Tb^{152}$ (18 h), $Tb^{153}$ (2.58 d), $Tb^{154m}$ (8 h), $Tb^{154}$ (21 h), $Tb^{165}$ (5.4 d), $Tb^{160}$ (73 d), $Dy^{155}$ (10 h), $Dy^{157}$ (8.2 h), $Tm^{165}$ (1.21d), $Tm^{167}$ (9.6 d), $Tm^{168}$ (85 d), $Yb^{169}$ (32 d), $Lu^{169}$ (1.5 d), $Lu^{170}$ (2.0 d), $Lu^{171}$ (8.3 d), $Lu^{172}$ (6.7 d), $Lu^{173}$ (1.3 y), $Lu^{174m}$ (165 d), $Hf^{173}$ (24 h), $Hf^{175}$ (70 d), $Ta^{175}$ (11 h), $Ta^{176}$ (8.0 h), $Ta^{177}$ (2.21 d), $Ta^{179}$ (1.6 y), $Ta^{180m}$ (8.1 h); the EC isotopes of very heavy metals $W^{181}$ (130 d), $Re^{181}$ (20 h), $Re^{182m}$ (13 h), $Re^{182}$ (64 h), $Re^{183}$ (71 d), $Re^{184m}$ (2.2 d), $Re^{184}$ (50 d), $Re^{186}$ (90 h), $Os^{183m}$ (10 h), $Os^{183}$ (12 h), $Os^{185}$ (94 d), $Ir^{185}$ (15 h), $Ir^{187}$ (12 h), $Ir^{188}$ (1.71 d), $Ir^{189}$ (11 d), $Ir^{190}$ (11 d), $Ir^{192}$ (74 d), $Pt^{191}$ (3.0 d), $Au^{193}$ (15.8 h), $Au^{194}$ (39 h), $Au^{195}$ (200 d), $Au^{196}$ (5.55 d), $Hg^{193m}$ (1.1 d), $Hg^{193}$ (6 h), $Hg^{194}$ (130 d), $Hg^{195}$ (1.66 d), $Hg^{195}$ (9.5 h), $Hg^{197m}$ (24 h), $Hg^{197}$ (2.71 d), $Tl^{200}$ (1.08 d), $Tl^{201}$ (3.04 d), $Tl^{202}$ (12 d), $Tl^{204}$ (3.9 y), $Pb^{200}$ (21 h), $Pb^{201}$ (9.4 h), $Pb^{202}$ (2.17 d), $Bi^{203}$ (12.3 h), $Bi^{204}$ (11.6 h), $Bi^{206m}$ (15.3 d), $Bi^{206}$ (6.3 d), $Bi^{207}$ (30 y); and the EC isotopes of actinides $Po^{206}$ (8.8 d), $At^{210}$ (8.3 h), $At^{211}$ (7.2 h), $Rn^{211}$ (16 h), $Ac^{226}$ (29 h), $Pa^{228}$ (22 h), $Pa^{229}$ (1.5 d), $U^{231}$ (4.2 d), $Np^{234}$ (4.4 d), $Pu^{234}$ (9 h), $Pu^{237}$ (45.6 d), $Am^{239}$ (12 h), $Cm^{241}$ (35 d), $Bk^{245}$ (4.95 d), $Bk^{246}$ (1.8 d).

81. An apparatus according to claim 80, wherein the radioisotope is adducted to an organic compound.

82. An apparatus according to claim 1, wherein the isotope is $I^{123}$, $I^{125}$, $I^{126}$, $Br^{76}$, or $Br^{77}$.

83. An apparatus according to claim 1, wherein the pulse shape analyzer comprises an article of manufacture comprising a computer readable storage medium having a substrate physically configured to represent a computer program, the computer program comprising means for analysing each pulse shape record by at least one software module having acceptance criteria, rejecting a pulse on-line if it does not satisfy the acceptance criteria of all the software modules utilized, and counting the pulse if it satisfies the acceptance criteria of all the software modules utilized.

84. An apparatus according to claim 1, wherein the detector assembly comprises:
   a scintillator crystal,
   a photomultiplier optically connected to the scintillator crystal, an integral photomultiplier base electronics module connected to the photomultiplier, comprising a high voltage power supply, voltage divider, and amplifier, shields between the base module and the photomultiplier, between the photomultiplier and the scintillator crystal, around the photomultiplier, and around the scintillator-photomultiplier-base module assembly.

85. An apparatus according to claim 1, further comprising an imaging processor that receives counting data from the pulse shape analyzer for a two dimensional array of multiple samples, and reconstructs an image of the array showing the presence of radioisotope.

86. A method for detecting a radioisotope in a sample, comprising:

placing the sample in a sample holder between two opposed detectors;

detecting emissions from the sample using the two opposed detectors to obtain electrical output pulses;

comparing the output pulses to predetermined acceptance criteria for the two detectors;

rejecting output pulses that do not satisfy the predetermined acceptance criteria; and accepting output pulses that satisfy the predetermined acceptance criteria.

87. A method for detecting a radioisotope in a sample as in claim 86, further comprising:

normalizing the output pulse amplitude to fall within a predetermined range over a baseline and to correlate with the energy of the emissions;

generating a first trigger pulse when there is a triggering output pulse for which the amplitude of the output pulse exceeds a predetermined threshold value, and generating a second trigger pulse when there are two simultaneous triggering output pulses for which the amplitude of the output pulses exceeds the predetermined threshold value, and rejecting pulses that do not exceed the predetermined threshold value;

responsive to a trigger pulse, capturing a predetermined number of subsequent normalized output pulses;

analyzing the captured output pulses as to predetermined isotope and system-dependent acceptance criteria; and counting pulses that satisfy the acceptance criteria and rejecting pulses that do not satisfy the acceptance criteria.

88. A method according to claim 86, wherein the radioisotope is a coincident gamma/x-ray emitter and the method can detect an amount of the CGX emitter in the sample of about 100 picoCurie.

89. A method according to claim 86, wherein the radioisotope is a coincident gamma/x-ray emitter and the method can detect an amount of the CGX emitter in the sample of about 1 picoCurie.

90. A method according to claim 86, further comprising the step of selecting the radioisotope from the lighter electron capture (EC) isotopes, the EC isotopes of lanthanides, the EC isotopes of heavy metals, and the EC isotopes of actinides.

91. A method according to claim 86, wherein the radioisotope is an isotope of an element that forms covalent bonds.

92. A method according to claim 86, wherein the radioisotope is $I^{123}$, $I^{125}$, $I^{126}$, $Br^{76}$, or $Br^{77}$.

93. A method according to claim 86, wherein the radioisotope is $I^{125}$.

94. A method according to claim 86, wherein the radioisotope is bound to a chelator conjugated to an organic compound.

95. A method according to claim 86, wherein the radioisotope is an isotope of the family of CGX lanthanide isotopes.

96. A method according to claim 86, wherein the radioisotope is adducted to an organic molecule.

97. A method according to claim 96, wherein the organic molecule is a monoclonal or polyclonal antibody or an antigen.

98. A method according to claim 97, wherein an antibody is used to detect cancerous cells in a physiological sample.

99. A method according to claim 96, wherein the organic molecule is used in a competitive assay.

100. A method according to claim 99, wherein the competitive assay is used to detect contamination of human physiological fluids.

101. A method according to claim 100, wherein the physiological fluid is blood, urine, sputum, tear drops, sweat, amniotic fluid or cerebro-spinal fluid.

102. A method according to claim 99, wherein the competitive assay is used to detect contamination of animal physiological fluids.

103. A method according to claim 99, wherein the competitive assay is used to detect contamination of food and agricultural products.

104. A method according to claim 103, wherein the contamination is the presence of microorganisms and their toxic byproducts.

105. A method according to claim 104, wherein the contamination comprises aflatoxins or mycotoxins.

106. A method according to claim 99, wherein the competitive assay is used to detect contamination of samples of water, soil or air from the environment.

107. A method according to claim 106, wherein the competitive assay is used to detect chemical contamination.

108. A method according to claim 99, wherein the competitive assay is performed upon airborne substances in a clean room environment, and data are used to estimate the number and size distribution of particulates in the air.

109. A method according to claim 86, wherein the method permits detection of one attomole of labeled molecule.

110. A method according to claim 86, wherein the radioisotope is adducted to an organic precursor for the synthesis of a macromolecule.

111. A method according to claim 86, wherein the radioisotope is adducted to a steroid compound.

112. A method according to claim 86, wherein the radioisotope is adducted to estrogen.

113. A method according to claim 112, wherein the level of estrogen and other steroids in physiological fluids is used to diagnose breast cancer.

114. A method according to claim 86, wherein the radioisotope is adducted to a protein.

115. A method according to claim 86, wherein the radioisotope is coupled to a precursor of nucleic acids.

116. A method according to claim 86, wherein the radioisotope is incorporated in a primer for nucleic chain elongation.

117. A method according to claim 116, further comprising using the primer in an in vitro nucleic acid amplification protocol.

118. A method according to claim 116, further comprising using the primer in the polymerase chain reaction (PCR) process.

119. A method according to claim 118, wherein the polynierase chain reaction is stopped while the amplification is still exponential.

120. A method according to claim 116, wherein the primer is used in a linear polymerase reaction.

121. A method according to claim 86, wherein the radio-isotope is coupled to a virus, a bacterial cell, an algae cell, a fungal cell, other cell or a protozoa.

122. A method according to claim 121, wherein the virus is an agent of sexually or blood transfusion transmitted disease, and the bacteria is tubercular bacillus or bacteria which are precursors of sexually transmitted diseases.

123. The method of claim 86, further comprising:
performing a setup of the apparatus by:
determining and storing detector dependent permitted ranges for a plurality of pulse shape rejection parameters for at least one detector, the parameters being associated with a desired characteristic emission to be detected;
operating the, apparatus to detect the desired characteristic emission by:
determining pulse shape parameters of an output signal from the at least one detector; and
comparing the pulse shape parameters of an output signal from the at least one detector with the stored detector dependent permitted ranges;
wherein, if the pulse shape parameters of the output signal from the at least one detector do not compare closely with the stored detector dependent permitted ranges, the output signal from the at least one detector is rejected as a detection of the desired characteristic emission.

124. The method according to claim 123, wherein the setup comprises:
providing to the at least one detector a sample of a source of the desired characteristic emission;
acquiring a plurality of pulses from the at least one detector;
building and storing histograms of the plurality of pulses, including current baseline, and pulse widths at ¼, ½ and ¾ of the pulse amplitude;
determining the detector dependent permitted ranges for a plurality of pulse shape rejection parameters for the at least one detector as those accepting 99%, for each histogram, of the contiguous dominant peak area of the histogram;
storing the determined detector dependent permitted ranges for the plurality of pulse shape rejection parameters for the at least one detector.

125. The method according to claim 123, wherein the at least one detector comprises a first and a second detector, and wherein the setup is performed for the first detector and repeated for the second detector.

126. The method according to claim 125, wherein the setup further comprises:
acquiring a plurality of coincident events, a coincident event being substantial coincidence of output from the first and second detectors;
determining and storing permitted ranges of pulse displacement parameters by building histograms and using the 99% accepting contiguous dominant peak area of the histogram approach; and
storing the permitted ranges of pulse displacement parameters.

127. The method according to claim 126, wherein the setup further comprises:
building three separate energy spectra associated with the desired characteristic emission, including a spectrum for the first detector, a spectrum for the second detector, and a two-dimensional spectrum of coincident events.

128. The method according to claim 123, wherein, in the operating of the apparatus to detect the desired characteristic emission, the determining pulse shape parameters of an output signal from the at least one detector comprises:
acquiring a plurality of data points for a received pulse over a time window spanning the whole width of the pulse and a short time prior to the rise of the pulse;
calculating an average of the first few data points to determine a current baseline;
if the calculated current baseline differs significantly from 0, rejecting the pulse as distorted by pile-up;
if the pulse was not rejected in the preceding step, scanning a plurality of next data points to find a maximum value;
if the maximum value found exceeds an overflow amount, rejecting the pulse;
if the pulse was not rejected in any of the preceding steps, calculating a peak amplitude of the pulse as the difference between the maximum value and the current baseline;
scanning forward and backward from the peak of the pulse to determine time offsets for amplitude levels at a plurality of fractions of the peak amplitude; and
using at least the determined time offsets as the pulse shape parameters of the output signal from the at least one detector.

129. The method according to claim 128, wherein, in operating the apparatus to detect the desired characteristic emission, the comparing of the pulse shape parameters of the output signal with the stored detector dependent permitted ranges comprises:
determining if the time offsets for amplitude levels of ½, ¼ and ¾, of the peak amplitude of the pulse are within the stored detector dependent permitted ranges.

130. The method according to claim 128, wherein the at least one detector comprises a first and a second detector,
wherein the setup further comprises:
acquiring a plurality of coincident events, a coincident event being substantial coincidence of output from the first and second detectors;
determining and storing permitted ranges of pulse displacement parameters by building histograms and using a 99% accepting contiguous dominant peak area of the histogram approach; and
storing the permitted ranges of pulse displacement parameters; and
wherein operating the apparatus to detect the desired characteristic emission further comprises testing for the occurrence of coincidence during operation, including:
determining the distance between the respective time offsets for the ¼ amplitude levels on the rising front of the respective pulses from the first and second detectors; and
comparing the determined distance with the stored permitted ranges of pulse displacement parameters.

131. The method according to claim 123, further comprising calibrating the apparatus for a particular isotope.

132. The method of claim 87, wherein the sample comprises a biomolecule to which is adducted a radioisotope selected from the group consisting of the lighter EC isotopes Be$^7$ (53.6 d), Na$^{22}$ (2.58 y), Ar$^{37}$ (34.3 d), V$^{49}$ (330.0 d), Cr$^{48}$ (23.0 h), Cr$^{51}$ (27.8 d), Mn$^{52}$ (5.6 d), Mn$^{54}$ (291.0 d), Fe$^{52}$ (8.0 h), Fe$^{55}$ (2.7 y), Co$^{55}$ (18.0 h), Co$^{56}$ (77.3 d), Co$^{57}$ (270.0 d), Co$^{58}$ (71.0 d), Ni$^{56}$ (6.4 d), Ni$^{57}$ (1.5 d), Cu$^{64}$ (12.8 h), $Zn^{62}$ (9.3 h), $Zn^{65}$ (245.0 d), $Ga^{66}$ (9.5 h), $Ga^{67}$ (78.0 h), $As^{71}$ (62.0 h), $As^{72}$ (26.0 h), $As^{73}$ (76.0 d), $As^{74}$ (18.0 d), $Se^{72}$ (8.4 d), $Se^{75}$ (120.0 d), $Br^{76}$ (16.5 h), $Br^{77}$ (2.6 d), $Kr^{76}$ (10.0 h), $Kr^{79}$ (1.6 d), $Rb^{82m}$ (6.3 h), $Rb^{83}$ (83.0 d), $Rb^{84}$ (33.0 d), $Sr^{82}$ (25.5 d), $Sr^{83}$ (1.6 d), $Sr^{85}$ (64.0 d), $Y^{83}$ (108.0 d), $Y^{86}$ (14.6 h), $Y^{87}$ (3.33 d), $Zr^{88}$ (85.0 d), $Zr^{89}$ (3.29 d), $Nb^{92}$ (10.1 d), $Tc^{93m}$ (60. d), $Tc^{96}$ (4.3 d), $Tc^{99m}$ (6.0 h), $Ru^{97}$ (2.9 d), $Rh^{99}$ (16. d), $Rh^{100}$ (21. h), $Rh^{102}$ (206 d), $Pd^{100}$ (4.0 d), $Pd^{101}$ (8.5 h), $Pd^{103}$ (17 d), $Ag^{105}$ (40 d), $Ag^{106m}$ (8.3 d), $Ag^{108m}$ (>5 y), $Cd^{107}$ (6.7 h), $Cd^{109}$ (470 d), $In^{111}$ (2.81 d), $In^{113}$ (118 d), $Sn^{113}$ (118 d), $Sb^{119}$ (158 d), $Sb^{122}$ (2.8 d), $Te^{118}$ (60 d), $Te^{119}$ (45 d), $Te^{121}$ (17 d), $I^{123}$ (4.2 d), $I^{126}$ (13.2 d), $Cs^{132}$ (6.5 d), $Ba^{128}$ (2.4 d), $Ba^{131}$ (11.6 d); the EC isotopes of lanthanides $La^{135}$ (19.8 h), $Ce^{133}$ (6.3 h), $Ce^{134}$ (3.0 d), $Ce^{135}$ (22.0 h), $Ce^{137}$ (9.0 h), $Ce^{139}$ (140 d), $Nd^{140}$ (3.3 d), $Pm^{143}$ (265 d), $Pm^{144}$ (440 d), $Pm^{145}$ (18 y), $Pm^{146}$ (710 d), $Pm^{158m}$ (40.6 d), $Sm^{145}$ (340 d), $Eu^{145}$ (5.6 d), $Eu^{146m}$ (1.58 d), $Eu^{146}$ (4.6 d), $Eu^{147}$ (24 d), $Eu^{148}$ (54 d), $Eu^{149}$ (120 d), $EU^{150m}$ (14 h), $Eu^{150}$ (5 y), $Eu^{152}$ (13 y), $Gd^{146}$ (48 d), $Gd^{147}$ (35 h), $Gd^{149}$ (9 d), $Gd^{151}$ (120 d), $Gd^{153}$ (200 d), $Tb^{151}$ (19 h), $Tb^{152}$ (18 h), $Tb^{153}$ (2.58 d), $Tb^{154m}$ (8 h), $Tb^{154}$ (21 h), $Tb^{165}$ (5.4 d), $Tb^{160}$ (73 d), $Dy^{155}$ (10 h), $Dy^{157}$ (8.2 h), $Tm^{165}$ (1.21d), $Tm^{167}$ (9.6 d), $Tm^{168}$ (85 d), $Yb^{169}$ (32 d), $Lu^{169}$ (1.5 d), $Lu^{170}$ (2.0 d), $Lu^{171}$ (8.3 d), $Lu^{172}$ (6.7 d), $Lu^{173}$ (1.3 y), $Lu^{174m}$ (165 d), $Hf^{173}$ (24 h), $Hf^{175}$ (70 d), $Ta^{175}$ (11 h), $Ta^{176}$ (8.0 h), $Ta^{177}$ (2.21 d), $Ta^{179}$ (1.6 y), $Ta^{180m}$ (8.1 h); the EC isotopes of very heavy metals $W^{181}$ (130 d), $Re^{181}$ (20 h), $Re^{182m}$ (13 h), $Re^{182}$ (64 h), $Re^{183}$ (71 d), $Re^{184m}$ (2.2 d), $Re^{184}$ (50 d), $Re^{186}$ (90 h), $Os^{183m}$ (10 h), $Os^{183}$ (12 h), $Os^{185}$ (94 d), $Ir^{185}$ (15 h), $Ir^{187}$ (12 h), $Ir^{188}$ (1.71 d), $Ir^{189}$ (11 d), $Ir^{190}$ (11 d), $Ir^{192}$ (74 d), $Pt^{191}$ (3.0 d), $Au^{193}$ (15.8 h), $Au^{194}$ (39 h), $Au^{195}$ (200 d), $Au^{196}$ (5.55 d), $Hg^{193m}$ (1.1 d), $Hg^{193}$ (6 h), $Hg^{194}$ (130 d), $Hg^{195}$ (1.66 d), $Hg^{195}$ (9.5 h), $Hg^{197m}$ (24 h), $Hg^{197}$ (2.71 d), $Tl^{200}$ (1.08 d), $Tl^{201}$ (3.04 d), $Tl^{202}$ (12 d), $Tl^{204}$ (3.9 y), $Pb^{200}$ (21 h), $Pb^{201}$ (9.4 h), $Pb^{202}$ (2.17 d), $Bi^{203}$ (12.3 h), $Bi^{204}$ (11.6 h), $Bi^{206}$ (15.3 d), $Bi^{206}$ (6.3 d), $Bi^{207}$ (30 y); and the EC isotopes of actinides $Po^{206}$ (8.8 d), $At^{210}$ (8.3 h), $At^{211}$ (7.2 h), $Rn^{211}$ (16 h), $Ac^{226}$ (29 h), $Pa^{228}$ (22 h), $Pa^{229}$ (1.5 d), $U^{231}$ (4.2 d), $Np^{234}$ (4.4 d), $Pu^{234}$ (9 h), $Pu^{237}$ (45.6 d), $Am^{239}$ (12 h), $Cm^{241}$ (35 d), $Kb^{245}$ (4.95 d), $Kb^{246}$ (1.8 d).

* * * * *